United States Patent
Ando

(10) Patent No.: US 10,295,841 B2
(45) Date of Patent: May 21, 2019

(54) METHOD FOR MANUFACTURING DIFFRACTIVE MULTI-FOCAL OPHTHALMIC LENS AND DIFFRACTIVE MULTI-FOCAL OPHTHALMIC LENS

(71) Applicant: MENICON CO., LTD., Nagoya-shi, Aichi (JP)

(72) Inventor: Ichiro Ando, Kasugai (JP)

(73) Assignee: MENICON CO., LTD., Nagoya-shi (JP)

( * ) Notice: Subject to any disclaimer, the term of this patent is extended or adjusted under 35 U.S.C. 154(b) by 185 days.

(21) Appl. No.: 15/500,589

(22) PCT Filed: Aug. 5, 2015

(86) PCT No.: PCT/JP2015/072205
§ 371 (c)(1),
(2) Date: Jan. 31, 2017

(87) PCT Pub. No.: WO2016/021627
PCT Pub. Date: Feb. 11, 2016

(65) Prior Publication Data
US 2017/0219846 A1    Aug. 3, 2017

(30) Foreign Application Priority Data

Aug. 8, 2014  (JP) ................. 2014-163159

(51) Int. Cl.
*G02C 7/02* (2006.01)
*G02C 7/04* (2006.01)
(Continued)

(52) U.S. Cl.
CPC ............ *G02C 7/028* (2013.01); *A61F 2/1616* (2013.01); *A61F 2/1654* (2013.01); *G02B 5/18* (2013.01);
(Continued)

(58) Field of Classification Search
CPC ....... A61F 2/1616; A61F 2/1654; G02C 7/02; G02C 7/024; G02C 7/028; G02C 7/041;
(Continued)

(56) References Cited

U.S. PATENT DOCUMENTS 6,829,093 B1   12/2004 Nakai
8,500,805 B2    8/2013 Kobayashi et al.
(Continued)

FOREIGN PATENT DOCUMENTS

EP    2378319 A1   10/2011
JP    H03-062001 A   3/1991
(Continued)

OTHER PUBLICATIONS

Oct. 27, 2015 Search Report issued in International Patent Application No. PCT/JP2015/072205.
(Continued)

*Primary Examiner* — William R Alexander
*Assistant Examiner* — Ephrem Z Mebrahtu
(74) *Attorney, Agent, or Firm* — Oliff PLC

(57) ABSTRACT

A method for manufacturing a diffractive multi-focal ophthalmic lens capable of generating at least three focal points in an optical axis direction using a diffractive structure comprising a plurality of zones in a concentric circle form. A composite profile is generated by overlapping at least two starting profiles comprising a plurality of zones in a concentric circle form, and an adjusted profile is generated in which at least one of phase and amplitude is adjusted by employing a zone of the composite profile as a subject in order to set an intensity distribution in the optical axis direction and determine optical characteristics, to manufacture the diffractive multi-focal ophthalmic lens for which the adjusted profile is provided in at least a portion of the diffractive structure.

29 Claims, 27 Drawing Sheets

(51) Int. Cl.
*A61F 2/16* (2006.01)
*G02B 5/18* (2006.01)

(52) U.S. Cl.
CPC ............... *G02C 7/04* (2013.01); *G02C 7/044* (2013.01); *G02C 7/06* (2013.01); *G02C 2202/08* (2013.01); *G02C 2202/20* (2013.01)

(58) Field of Classification Search
CPC ...... G02C 7/044; G02C 7/06; G02C 2202/08; G02C 2202/20
See application file for complete search history.

(56) References Cited

U.S. PATENT DOCUMENTS

| | | | |
|---|---|---|---|
| 8,636,796 B2 | 1/2014 | Houbrechts et al. | |
| 2011/0267693 A1* | 11/2011 | Kobayashi | A61F 2/1602 359/569 |
| 2012/0140166 A1* | 6/2012 | Zhao | A61F 2/1618 351/159.15 |

FOREIGN PATENT DOCUMENTS

| | | |
|---|---|---|
| JP | 2001-042112 A | 2/2001 |
| JP | 2010-158315 A | 7/2010 |
| JP | 2013-517822 A | 5/2013 |
| JP | 5525114 B1 | 6/2014 |
| WO | 2009/130610 A2 | 10/2009 |
| WO | 2010/079528 A1 | 7/2010 |
| WO | 2013/118176 A1 | 8/2013 |
| WO | 2013/118499 A1 | 8/2013 |

OTHER PUBLICATIONS

Mar. 15, 2018 Extended Search Report issued in European Patent Application No. 15829915.6.
Feb. 14, 2017 Preliminary Report on Patentability issued in International Patent Application No. PCT/JP2015/072205.
Apr. 2, 2019 Office Action issued in Japanese Application No. 2016-508893.

* cited by examiner

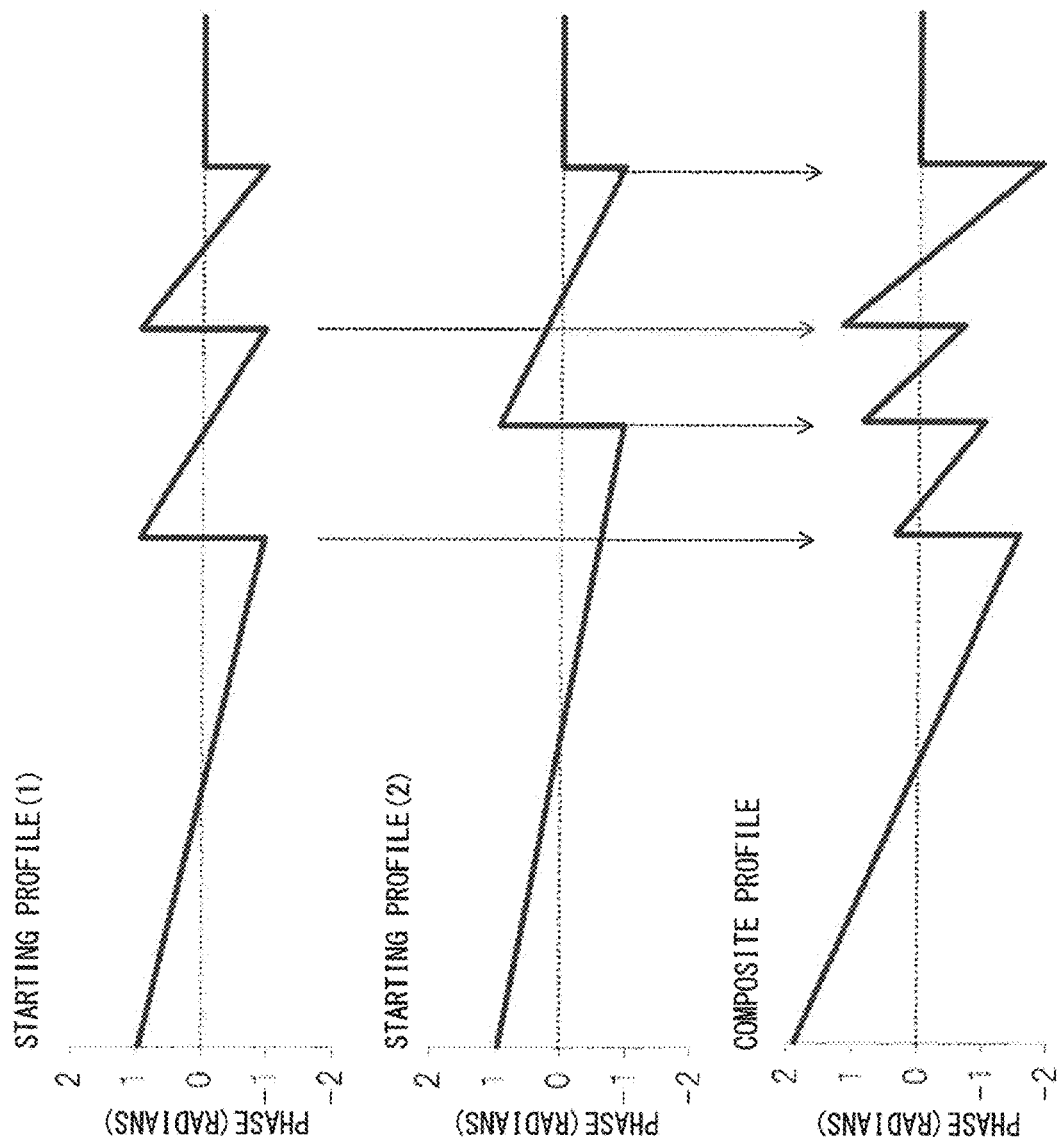

[EXAMPLE 1]
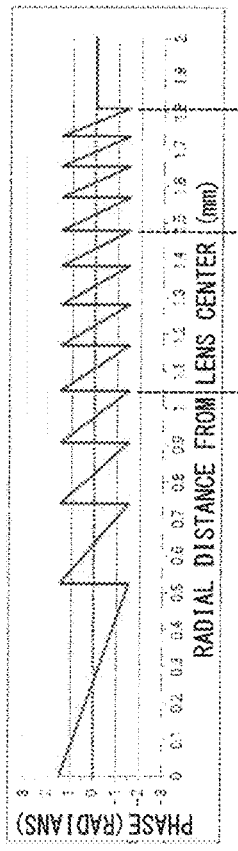
FIG.5A
STARTING PROFILE (1)
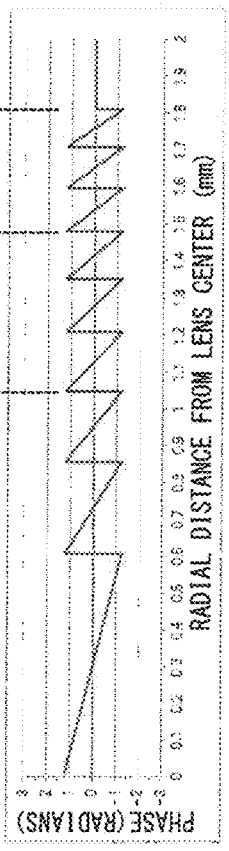
FIG.5B
STARTING PROFILE (2)
FIG.5C
COMPOSITE PROFILE
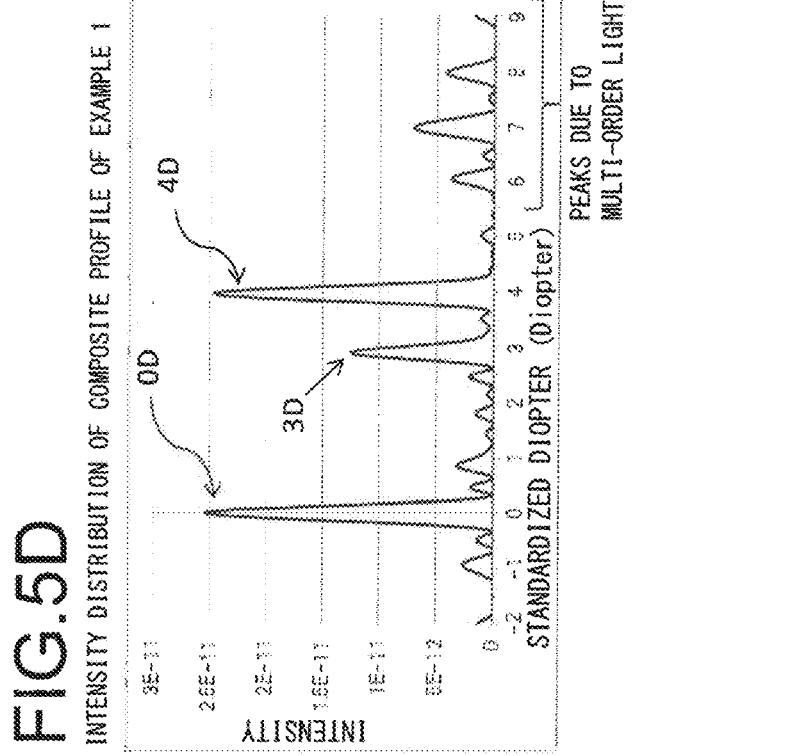
FIG.5D
INTENSITY DISTRIBUTION OF COMPOSITE PROFILE OF EXAMPLE 1

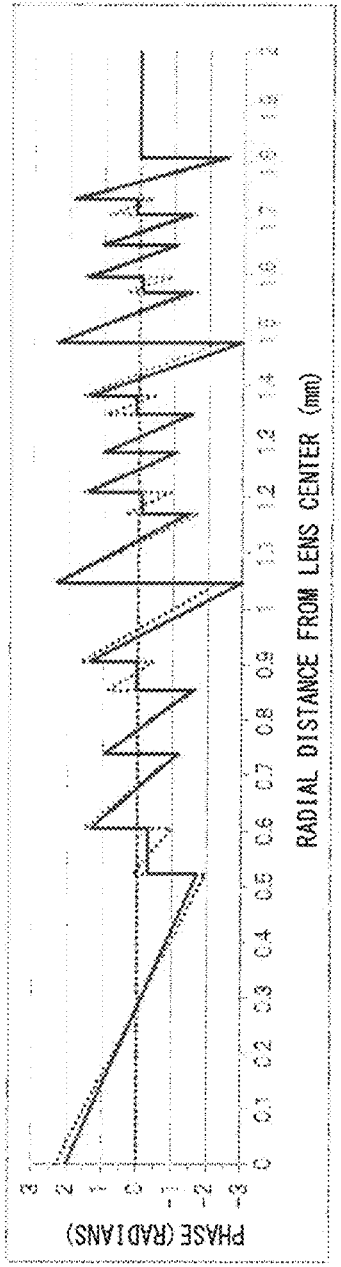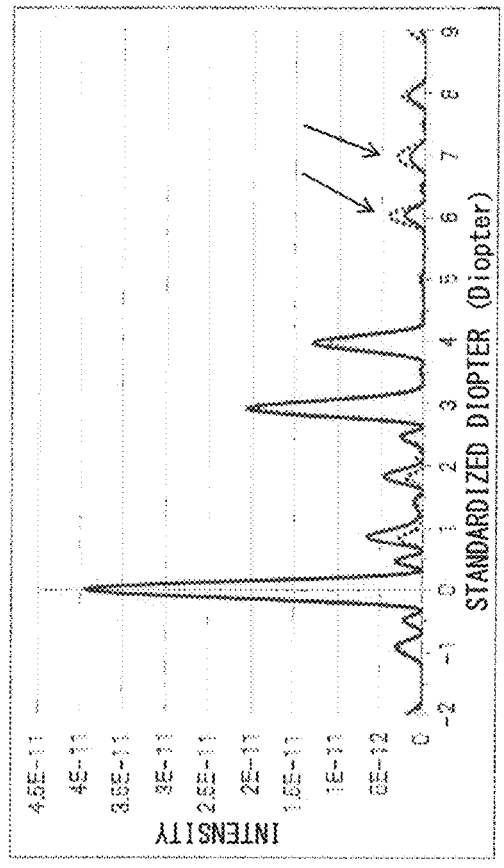

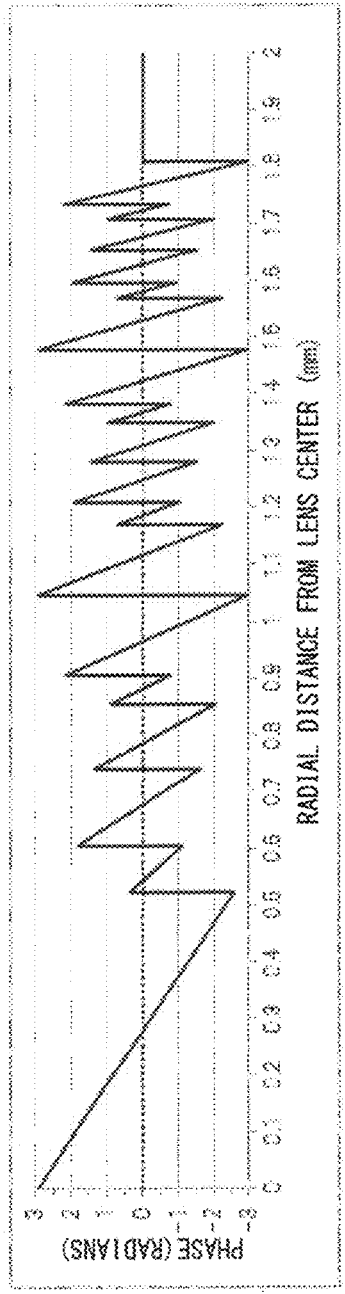
FIG.9A COMPOSITE PROFILE OF EXAMPLE 3
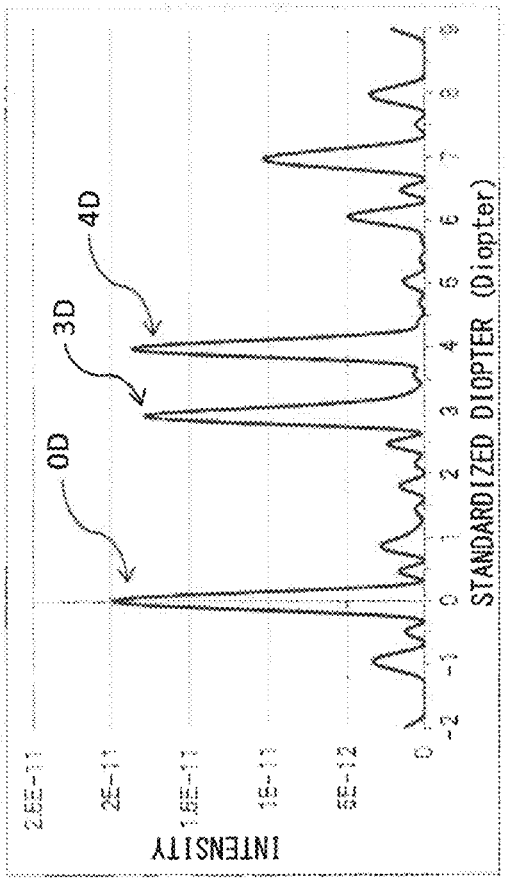
FIG.9B INTENSITY DISTRIBUTION OF COMPOSITE PROFILE OF EXAMPLE 3

[EXAMPLE 4]

ADJUSTED PROFILE OF EXAMPLE 4    TRANSMITTANCE: 50%

SOLID LINE; ADJUSTED PROFILE    DASHED LINE; ADJUSTED PROFILE

INTENSITY DISTRIBUTION OF ADJUSTED PROFILE OF EXAMPLE 4

SOLID LINE; ADJUSTED PROFILE    DASHED LINE; ADJUSTED PROFILE

[EXAMPLE 5] FIG. 12A
ADJUSTED PROFILE OF EXAMPLE 5                    TRANSMITTANCE: 0 %
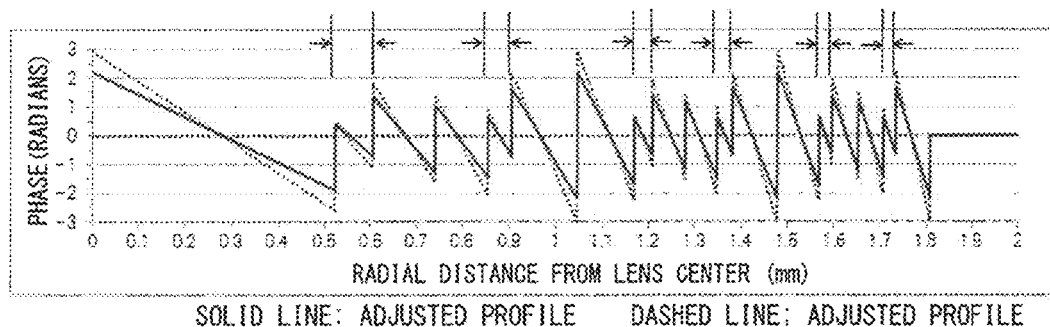
SOLID LINE: ADJUSTED PROFILE    DASHED LINE: ADJUSTED PROFILE
FIG. 12B
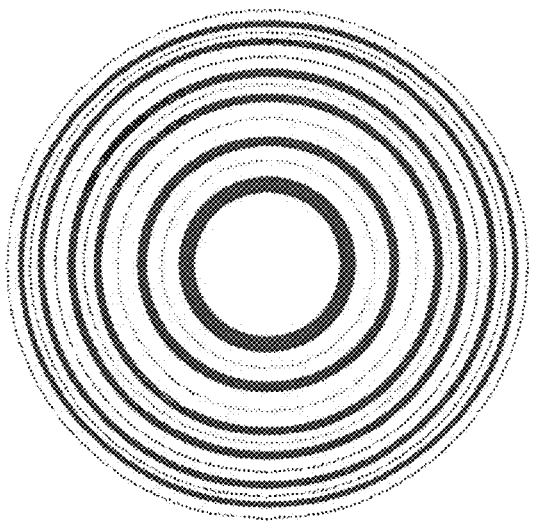
FIG. 12C
INTENSITY DISTRIBUTION OF ADJUSTED PROFILE OF EXAMPLE 5
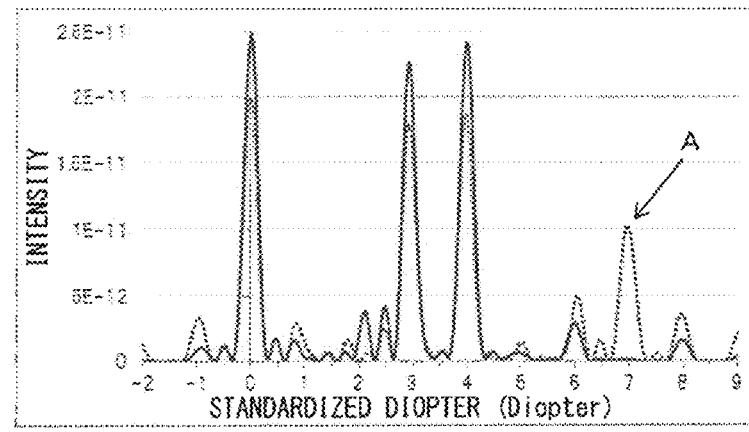
SOLID LINE: ADJUSTED PROFILE    DASHED LINE: ADJUSTED PROFILE

[EXAMPLE 6]

STARTING PROFILE (1)

STARTING PROFILE (2)

COMPOSITE PROFILE

INTENSITY DISTRIBUTION OF COMPOSITE PROFILE OF EXAMPLE 6

ADJUSTED PROFILE OF EXAMPLE 6

SOLID LINE: ADJUSTED PROFILE   DASHED LINE: COMPOSITE PROFILE

INTENSITY DISTRIBUTION OF ADJUSTED PROFILE OF EXAMPLE 6

SOLID LINE: ADJUSTED PROFILE   DASHED LINE: COMPOSITE PROFILE

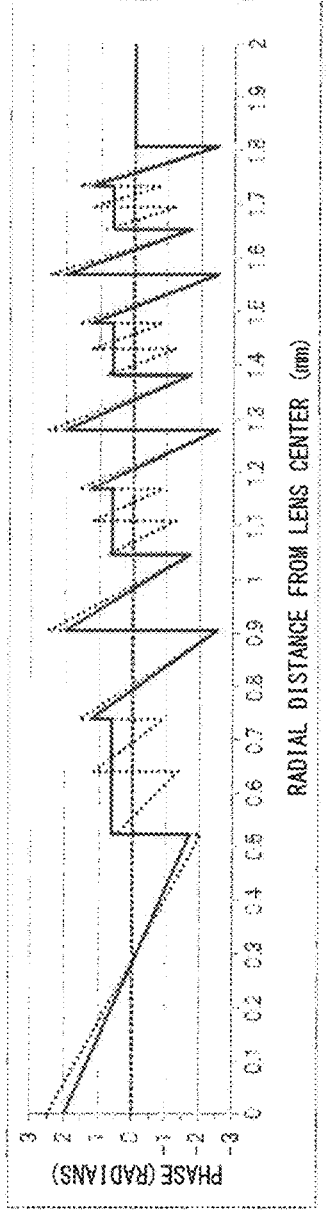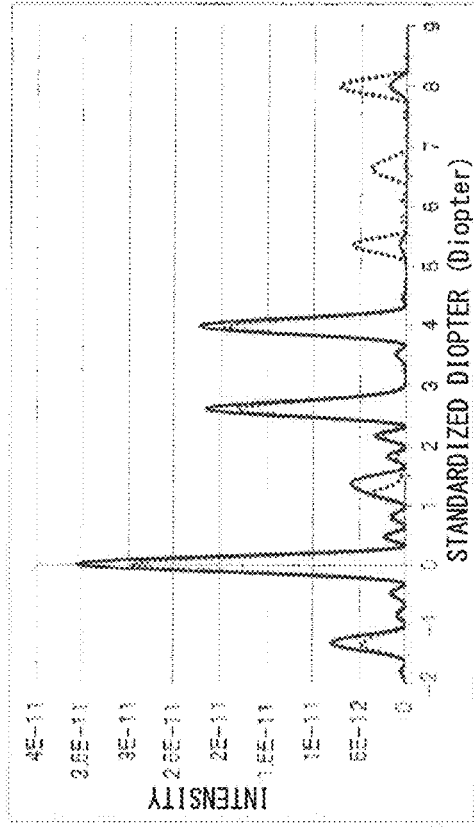
FIG. 15A ADJUSTED PROFILE OF EXAMPLE 7
FIG. 15B INTENSITY DISTRIBUTION OF ADJUSTED PROFILE OF EXAMPLE 7

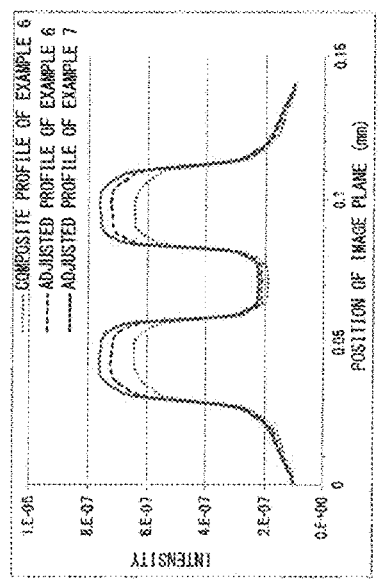
FIG.18E
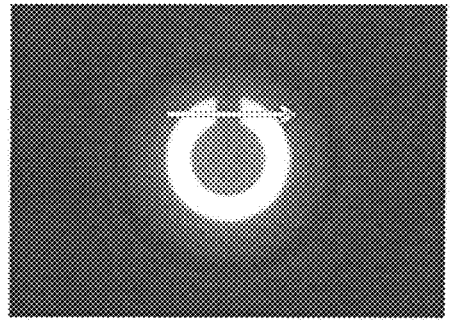
FIG.18C
FIG.18D
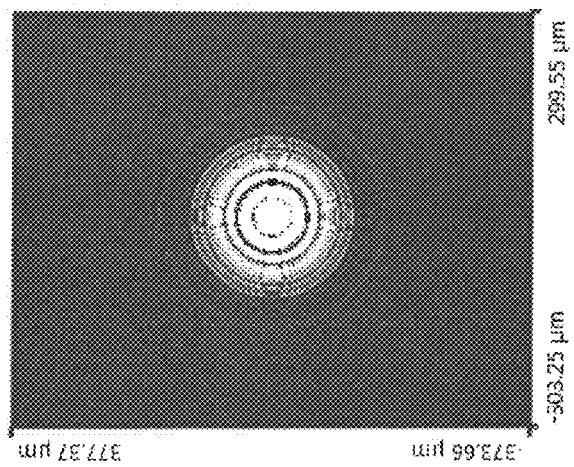
FIG.18A
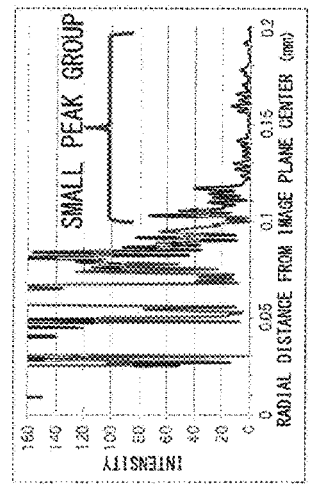
FIG.18B

[EXAMPLE 8]

STARTING PROFILE (1)

STARTING PROFILE (2)

STARTING PROFILE (3)

COMPOSITE PROFILE

INTENSITY DISTRIBUTION OF COMPOSITE PROFILE OF EXAMPLE 8

ADJUSTED PROFILE OF EXAMPLE 8

STANDARD FRESNEL ZONE FOR WHICH ADDITION POWER IS 4D

ADJUSTED PROFILE OF EXAMPLE 7

[EXAMPLE 9]
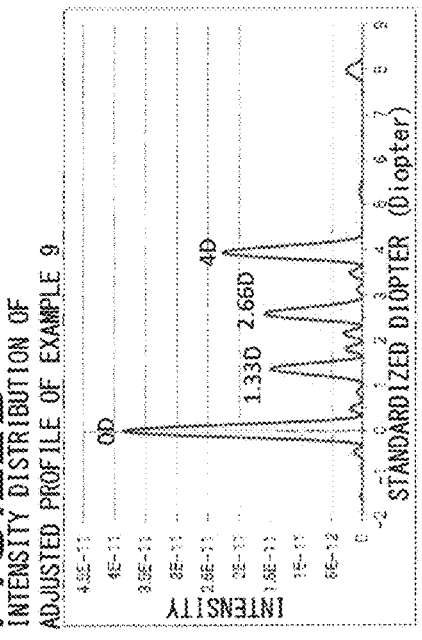
FIG.22A
ADJUSTED PROFILE OF EXAMPLE 9
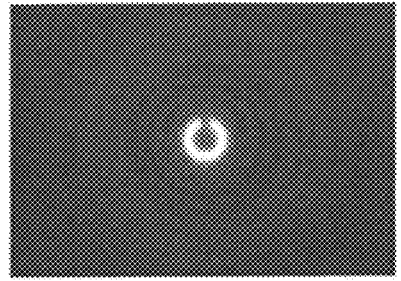
FIG.22B
INTENSITY DISTRIBUTION OF ADJUSTED PROFILE OF EXAMPLE 9
SIMULATION RESULTS OF VISUAL PERFORMANCE WHEN ADJUSTED PROFILE OF EXAMPLE 9 IS ARRANGED IN EYE AS INTRAOCULAR LENS
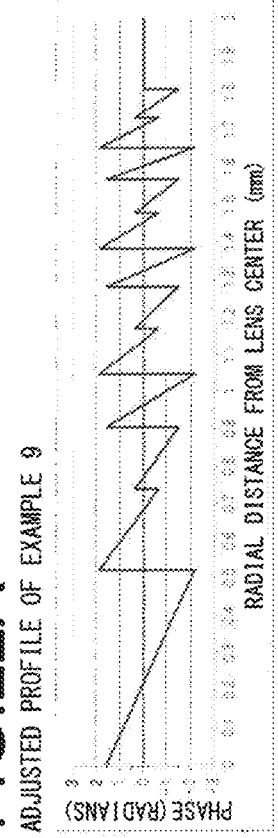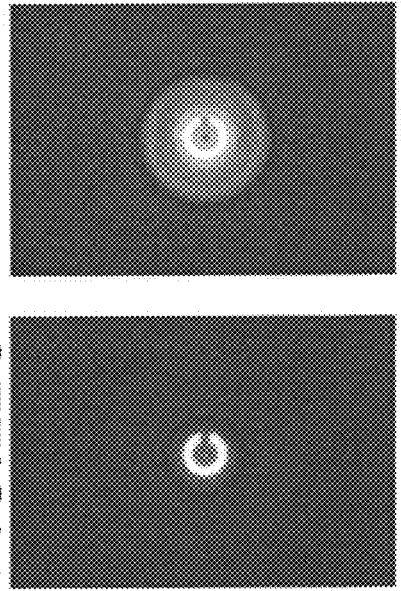
FIG.22C ∞
FIG.22D 90 cm
FIG.22E 50 cm
FIG.22F 35 cm
IN FRONT

[EXAMPLE 11]

STARTING PROFILE(1) (SOLID LINE) AND
STARTING PROFILE(2) (DASHED LINE)

COMPOSITE PROFILE

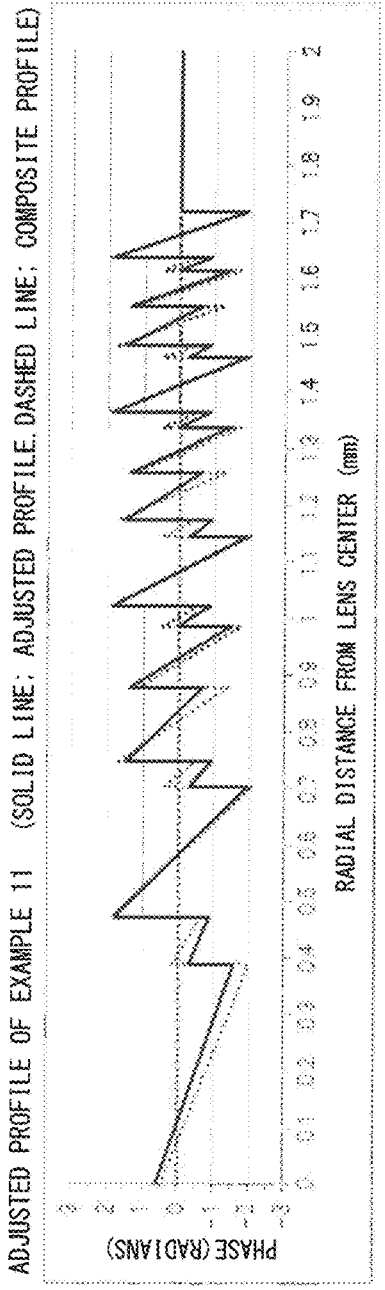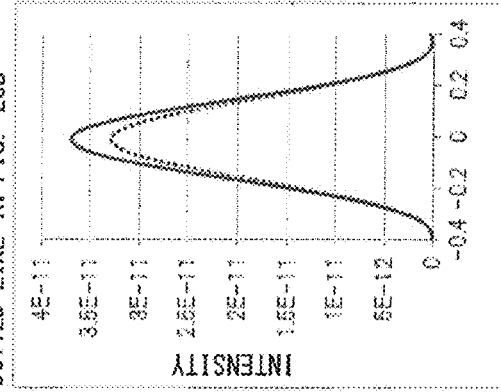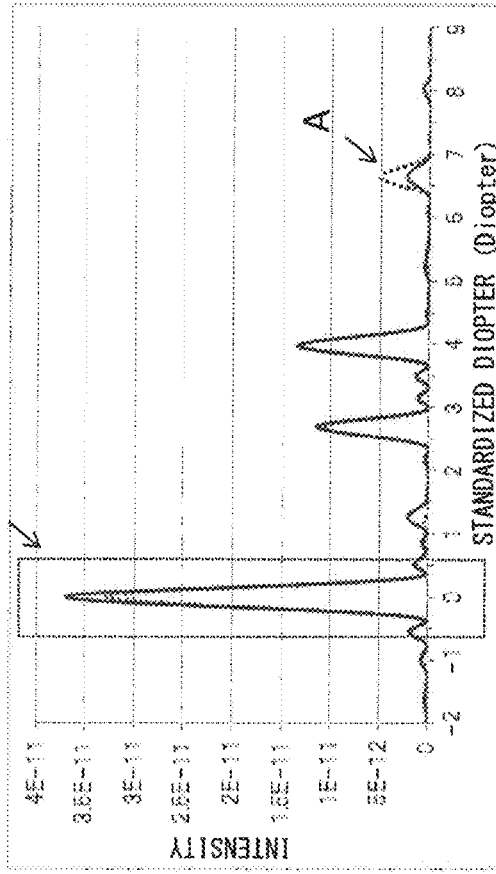
FIG.25A ADJUSTED PROFILE OF EXAMPLE 11 (SOLID LINE: ADJUSTED PROFILE, DASHED LINE: COMPOSITE PROFILE)
FIG.25B INTENSITY DISTRIBUTION OF ADJUSTED PROFILE OF EXAMPLE 11
FIG.25C ENLARGED VIEW OF REGION ENCLOSED BY DOTTED LINE IN FIG. 25B

[EXAMPLE 12]

STARTING PROFILE(1) (SOLID LINE) AND
STARTING PROFILE(2) (DASHED LINE)

COMPOSITE PROFILE

INTENSITY DISTRIBUTION OF COMPOSITE PROFILE OF EXAMPLE 12

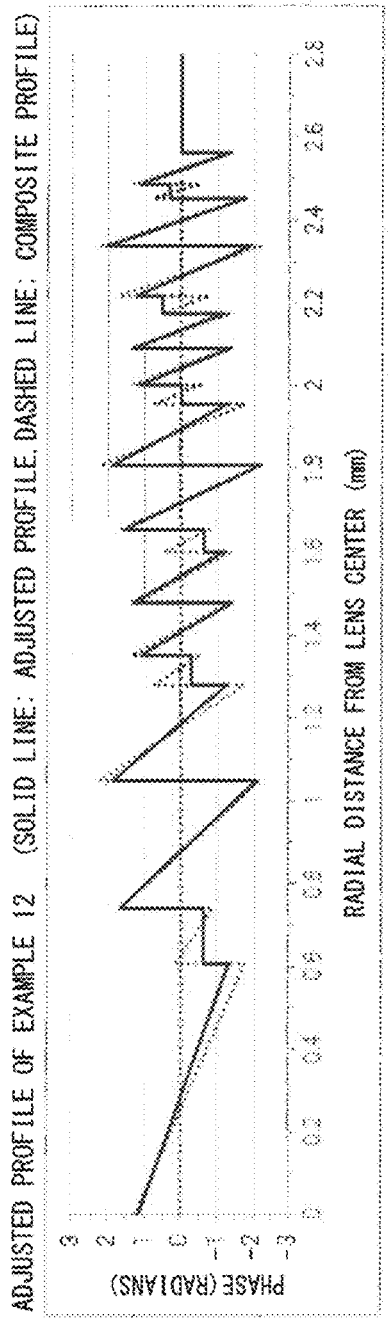
FIG.27A
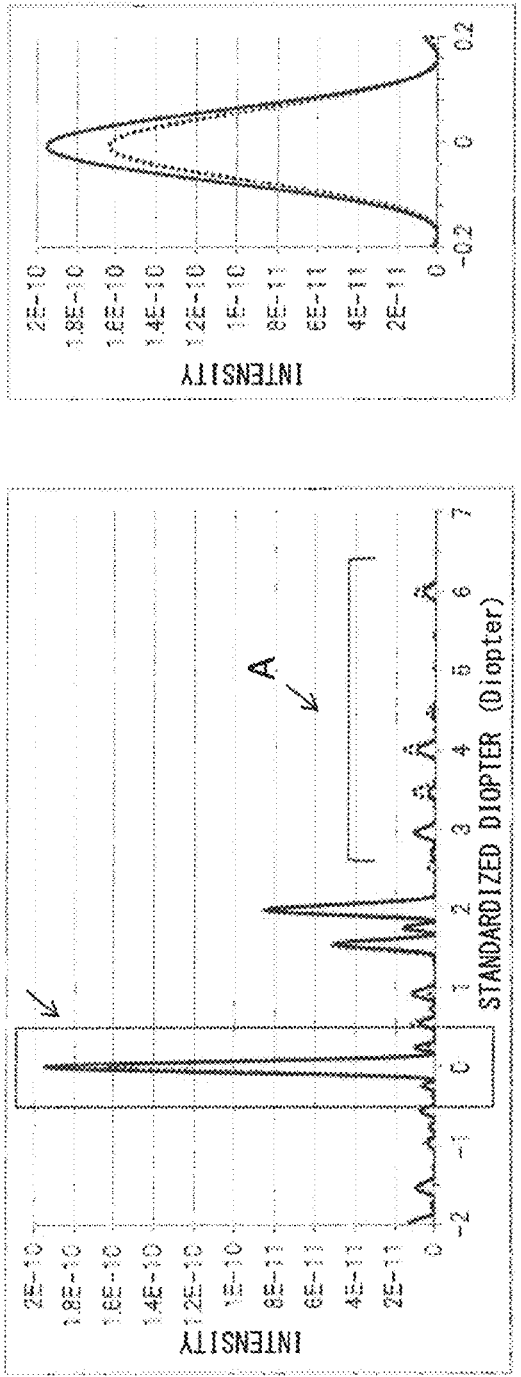
FIG.27B
FIG.27C

METHOD FOR MANUFACTURING DIFFRACTIVE MULTI-FOCAL OPHTHALMIC LENS AND DIFFRACTIVE MULTI-FOCAL OPHTHALMIC LENS

TECHNICAL FIELD

The present invention relates to a diffractive multi-focal ophthalmic lens that generates a plurality of focal points using diffracted light, and specifically provides a novel method for manufacturing a diffractive multi-focal ophthalmic lens and a novel diffractive multi-focal ophthalmic lens.

BACKGROUND ART

Multi-focal type optical lenses having a plurality of focal points are known from the past, as one type of ophthalmic lenses used for a human eye optical system. For example, with contact lenses used as corrective optical elements for refractive error, alternative optical elements after lens extraction or the like with the optical system of the human eye, or with intraocular lenses used for insertion in the human eye, by applying multi-focal lenses, it is possible to compensate for the decrease or loss of accommodation function of eye in the human body.

Particularly in recent years, there is an increase in people continuing to use contact lenses even when they reach the age of having presbyopia. People with presbyopia have a decrease in focus accommodation function, so a symptom appears of having difficulty focusing on nearby items. Thus, multi-focal contact lenses which can also focus on nearby objects become necessary for presbyopia patients. Also, for patients who have undergone cataract surgery, the lens which is in charge of the adjustment function is removed, so even if an intraocular lens is inserted as a replacement, the symptom of difficulty seeing close up remains. A multi-focal function that offers a plurality of focal points is necessary for that intraocular lens as well. Thus, there is a great increase in the need for multi-focal lenses reflecting the aging society of recent years.

However, as a method for realizing this multi-focal lens, examples are known of a refraction type multi-focal lens for which a plurality of focal points are formed based on the principle of refraction, and of a diffractive type multi-focal lens for which a plurality of focal points are formed based on the principle of diffraction. With the latter diffractive type multi-focal lens (diffractive multi-focal lens), equipped are a plurality of diffractive structures formed in concentric circle formed on the optical part of the lens, and a plurality of focal points are given by the mutual interference effect of light waves that passed through the plurality of diffractive structures (zones). Thus, compared to the refraction type lens with which a focal point is given by the refraction effect of light waves at a refracting surface comprising boundary surfaces with different refractive indexes, with the diffractive type multi-focal lens, there are advantages such as being able to set a high lens power while inhibiting an increase in lens thickness.

Typically, the diffractive multi-focal lens has a diffractive structure by which the diffractive zone pitch gradually becomes smaller as it goes from the lens center toward the periphery according to a rule called the Fresnel zone, and this has multiple focal points by using different orders of diffracted light generated from that structure. In particular, when using a diffractive multi-focal lens as a contact lens or an intraocular lens, normally, 0th order diffracted light is the focal point for far vision, and +1 order diffracted light is the focal point for near vision. By distribution of this diffracted light, it is possible to make a bifocal lens having focal points for far and near vision. The general Fresnel zone constitution is basically the zone pitches having the zone radius determined by Equation 1 below. This Equation 1 is hereafter called a Fresnel zone setting equation. Besides, the zone radius and the zone diameter refer to the radius of the zone outer diameter.

$$r_n = \sqrt{\frac{nK}{P}} \qquad \text{[Equation 1]}$$

$r_n$ is the outer diameter radius of the nth zone obtained from Equation 1. K is a constant. P is addition power for setting the focus point of first order diffracted light with the focus point of 0th order diffracted light as a reference, and by varying this, it is possible to change the focal point position of the first order diffracted light.

For example when the focal point by 0th order diffracted light is a focal point for far vision, and first order diffracted light is set as the focal point for near vision, when P (the addition power noted above) is made larger, the focal point position for near vision moves closer to the lens. Specifically, when using that lens for the human eye, objects that are closer become visible. Conversely, when P is made smaller, the focal position for near vision recedes away from the lens. In this case, when the lens is used in the human eye, the near points that are visible recede away.

For patients with advanced presbyopia, or patients who have an intraocular lens inserted, power of accommodation of the crystalline lens decreases or is lost, so it is preferable to use a lens for which the focal point is matched in the nearer direction as with the former example. In other words, an item is needed for which the addition power is set to be large. On the other hand, for patients for which the power of accommodation has not decreased that much, even if the near focal point position is not made that near, it is possible to see near objects by joint use with one's own residual power of accommodation, so there are cases when large addition power does not need to be set. Taking into consideration the status of the eyes of these patients, it is possible to obtain bifocal lenses that can be suitably used at different required powers for each patient by setting P.

Furthermore, in recent years, with the goal of improving visual performance in the intermediate region between two focal points of a focal point for far vision and a focal point for near vision, diffractive multi-focal lenses with a focal point set for intermediate vision have been proposed. This diffractive multi-focal lens with three or more focal points set has a plurality of types of reliefs for which their respective diffractive primary lights give mutually different focal point distances formed overlapping, having a synchronous structure for which the grating pitches for the reliefs overlap with each other periodically. As specific examples, for example, disclosed previously by this patent applicant, there are Japanese Unexamined Patent Publication No. JP-A-2010-158315 (Patent Document 1) and PCT Japanese Translation Patent Publication No. JP-A-2013-517822 showing the subordinate concepts thereof (Patent Document 2).

However, with the diffractive multi-focal lens with three or more focal points set using the background art constitution, there was the problem that it was difficult to sufficiently ensure the degree of freedom for tuning the optical characteristics respectively requested for the plurality of focal points. In particular, with the inventions noted in Patent Documents 1 and 2, when setting the plurality of focal points, effective tuning technology was not yet established by which while adjusting the light intensity of each focal point, there is suppression of noise form peaks due to multi-order light or the like that is generated secondarily on the optical axis other than the target focal points.

Also, with the invention noted in Patent Document 1, when setting the intermediate focal point between the far focal point and the near focal point, there was the problem that it is difficult to set the intermediate focal point to an optional target position on the optical axis.

BACKGROUND ART DOCUMENT

Patent Document

Patent Document 1: JP-A-2010-158315
Patent Document 2: JP-A-2013-517822

SUMMARY OF THE INVENTION

Problem the Invention Attempts to Solve

The present invention was created with the background of the problems described above of not yet having sufficiently established optical characteristics tuning technology with the diffractive multi-focal ophthalmic lens of the background art constitution, and the problem to address is to realize a diffractive multi-focal ophthalmic lens that can generate at least three focal points on the optical axis, being a novel manufacturing method for a diffractive multi-focal ophthalmic lens and a novel diffractive multi-focal ophthalmic lens for which the light intensity distribution on the optical axis can be adjusted and set efficiently and with good precision, and for which it is possible to provide a novel tuning method for the optical characteristics.

Also, with the invention of specific claims of the present invention (e.g. claims 14 and 15), another object is, to make it possible to set at least three focal points at any position on the optical axis with a high degree of freedom.

Furthermore, with the invention of other specific claims of the present invention (e.g. claim 9), it is possible to have a diffractive structure with which it is possible to generate at least three or more focal points even with a standard diffractive structure for which only two focal points could be generated with the background art, and it is possible to provide a diffractive multi-focal ophthalmic lens for which it is possible to simplify the design and structure by that standard structure, and to inhibit to the extent possible optical loss such as by scattering or the like.

Means for Solving the Problem

[i] Definition of Terms

Following, before describing the summary of the present invention, terminology and the like used with the present invention is defined as follows.

The wave function (distribution) is a function (distribution) for which the characteristics as a light wave are described mathematically, and in specific terms, is expressed by Equation 2.

$$\text{Wave function} = A(x)e^{i\phi(x)} \text{ or Wave function} = A(x)\cos\{\phi(x)\} \quad \text{[Equation 2]}$$

x: Variable

Phase correlates to $\phi(x)$ in Equation 2, and is one parameter showing the status of light as a wave, and in specific terms, establishes the position of the valleys or peaks of the waves, or the positions for each elapsed time segment. Also, by changing the phase, the progress of the wave is advanced or delayed. With the present invention, phase is noted by $\phi$, and the unit is radians. For example, one wavelength of light is expressed as $2\pi$ radians, and half a wavelength as $\pi$ radians. Note that the wave function in Equation 2 serves not only as a description by which the characteristics of the light wave are shown but also as an expression as a lens characteristic function that describes a physical action of a lens which can change characteristics of the incident light on the lens.

Phase function means a function $\phi(x)$ expressing phase change in the exponent part or the cos function of Equation 2. With the present invention, the phase function is defined as an item that mathematically expresses the physical effect provided on the lens such as giving changes to the phase with some method on the light made incident to the lens, and the phase function variable is used mainly as an item that has the radial direction position r from the center of the lens, and expresses the lens phase $\phi$, at the r point, and in specific terms, is expressed by the r–$\phi$ coordinate system shown in FIG. 1.

Also, an item for which the phase distribution of the entire region in which the phase function is provided is expressed with the same coordinate system is called the phase profile, or simply a profile or zone profile. Note that the r axis of $\phi=0$ is the reference line, and at the point of $\phi=0$, it means that the incident light is emitted without changing the phase. Then, when a positive value is used for $\phi$ for this reference line, the light progress is delayed by that phase amount, and when a negative value is used for $\phi$, the light progress advances by that phase amount. With an actual ophthalmic lens, a refracting surface with no diffractive structure given correlates to this reference line (surface). The light undergoes the phase changes based on that phase function, and is emitted from the lens.

Also, the amplitude function is a function expressed by A(x) of Equation 2 noted above. With the present invention, it is defined as an item expressing the light transmittance when passing through a lens. The amplitude function variable is an item expressing the lens transmittance at point r, using the position r in the radial direction from the center of the lens. Also, the amplitude function is in a range of zero or greater and 1 or less, meaning that light is not transmitted at the point of A(r)=0, and incidental light is transmitted as is with no loss at the point of A(r)=1.

The optical axis is the lens rotation symmetrical axis, and here, means an axis for which the lens center extends to the object space and image side space.

0th order focal point means the focal point position of 0th order diffracted light. Hereafter, the +1 order diffracted light focal point position is called the +1 order focal point, the +2 order diffracted light focal point position is called the +2 order focal point, and so on.

A zone is used here as the minimum unit for the diffractive structure. For example, a region for which one blaze is formed is called one zone or zone region.

A blaze is one mode of a phase function, and indicates an item for which the phase is changing in a roof form shape, for example. With the present invention, the blaze is basically an item which changes in a straight line between the peaks (ridge lines) and valleys (trough lines) of the shed roof shapes in one zone shown in FIG. 2A which shows the cross section shape, but also included in the concept of a blaze with the present invention are items which, between the peaks and valleys, change in a parabola type curved line (FIG. 2B), irregular shapes (square wave shapes) (FIG. 2C), and the like. Also included in the blaze concept of the present invention are items which, between the peaks and valleys, are connected so as to change at a portion of the sine wave function (FIG. 2D), and items which are connected so as to change within an interval with no extrema. With the present invention, while no limitation is imposed, unless specifically noted in the description hereinbelow, as shown in FIG. 2A, with the blaze of the ith zone, as a rule, with the absolute value of phase $\phi_i$ of the position of outer diameter radius $r_i$ of the zone and the absolute value of phase $\phi_{i-1}$ of the position of inner diameter radius $r_{i-1}$ set to be equal in relation to the reference surface (line), in other words, set so as to have $|\phi_i|=|\phi_{i-1}|$, when the blaze is shifted in the $\phi$ axis direction in relation to the reference line, the blaze position is determined by setting the phase shift $\tau$ as shown in FIG. 3. In other words, in the drawing, when the blaze is shifted upper than the reference line (plus direction), $\tau$ is a positive value, and when it is shifted lower than the reference line (minus direction), $\tau$ is a negative value. Based on this definition, the blaze phase function $\phi$ (r) is expressed as shown with Equation 3. The unit of the phase shift $\tau$ in Equation 3 is the radian. The notations for the peak and valley position phases when the phase shift $\tau$ is set and the blaze is shifted in the $\phi$ axis direction in relation to the reference line are respectively $\phi_i'$ and $\phi_{i-1}'$ in relation to the default setting phase $\phi_i$ and $\phi_{i-1}$ as shown in FIG. 3. Specifically, there is a relationship of $\phi_i'=\phi_i+\tau$, $\phi_{i-1}'=\phi_{i-1}+\tau$.

$$\phi(r) = \frac{\phi_i - \phi_{i-1}}{r_i - r_{i-1}} \times r + \frac{\phi_{i-1} \times r_i - \phi_i \times r_{i-1}}{r_i - r_{i-1}} + \tau \quad [\text{Equation 3}]$$

r: Radial distance from the lens center
$r_{i-1}$: Inner diameter of the ith zone (radius)
$r_i$: Outer diameter of the ith zone (radius)
$\phi_{i-1}$: Phase at the inner diameter (radius) position of the ith zone
$\phi_i$: Phase at the outer diameter (radius) position of the ith zone
$\tau$: Phase shift Phase constant means the constant h defined with Equation 4 for blaze shaped phase functions.

$$h = \frac{\phi_{i-1} - \phi_i}{2\pi} \quad [\text{Equation 4}]$$

h: Phase constant
$\phi_{i-1}-\phi_i$: Phase difference between the phase of the inner diameter position and the phase of the outer diameter position of the ith diffraction zone The uneven square wave shaped item deemed to be included in the definition of blaze noted above is understood as a blaze when $\phi_{i-1}=\phi_i$, with Equation 4, specifically, h=0.

A relief is a generic name for the micro uneven structure reflecting the optical path length correlating to the phase established by the phase profile, specifically, formed on the surface of a lens by converting to the actual shape of the lens. The specific method for converting the phase profile to the relief shape is as noted hereafter.

Specifically, when light enters into a medium with a certain refractive index, its speed is reduced according to the refractive index. The light wavelength change as much as the change in speed resulting in a phase change. Since a positive phase in the phase profile means reduced speed of light, incident light into a region of high refractive index is equivalent to bringing it to a positive phase. The terms positive and negative phases are relative expressions, and comparing the phases of $-2\pi$ and $-\pi$ for example, the latter lags behind the former even with the same sign, thus setting a region of higher refractive index than the former.

For example, when there is a blaze shaped phase function, the actual shape blaze step is expressed by Equation 5. That relief shape can be provided on the lens surface using a precision lathe for cutting processing, a mold molding method, or the like.

$$\text{Blaze step} = h \times \frac{\lambda}{n_s - n_m} \quad [\text{Equation 5}]$$

h: Phase constant
$\lambda$: Wavelength
$n_s$: Refractive index of the lens base material
$n_m$: Refractive index of the medium facing the lens Starting profiles are profiles which are the base for obtaining a composite profile to achieve the diffracted structure of the present invention, and have the phase, amplitude, and zone defined previously. When the phase of the starting profile is set as a blaze shaped function, the representative mathematical expression of that phase function is expressed by Equation 3. The distinction between the phase of each starting profile zone or with another starting profile phase is expressed using the difference in the subscripts of the symbols in Equation 3. Also, in the description hereafter, the first, second, third, and so on starting profiles as the plurality of starting profiles are abbreviated as starting profile (1), (2), (3) and so on.

The composite profile is the profile obtained by overlapping the starting profiles in the same region of the zone radial direction. The phase of the composite profile is obtained as an item for which the starting profile phases are added and synthesized in the same region. When two types of blaze shaped phase functions are synthesized, as shown in FIG. 4, the blazes of starting profiles (1) and (2) are added in the radial direction, and a blaze having new peaks and valleys is generated. The function expressing that blaze shaped phase is expressed the same as with Equation 3, and the distinction between phases for each zone of the composite profile or for phases of the starting profiles is expressed using the difference in the subscript of the symbols. With the composite profile, the newly generated blaze is often shifted in the $\phi$ direction in relation to the reference line, so the notation of the blaze peak and valley position phases with the composite profile are noted as $\phi_{i-1}'$ and $\phi_i'$, as noted previously. Also, the zone that has the new blaze as the unit is one constituent zone of the composite profile, and zone numbers will be newly given for each respective zone.

An adjusted profile means a profile after at least one of the phase and amplitude has been adjusted with a zone unit with the composite profile. With an adjusted profile having a blaze shaped phase, the notation of the blaze peak and valley phases is noted using $\phi_{i-1}'$ and $\phi_i'$, the same as with the notation of the composite profile.

Intensity distribution is the intensity of light after passing through the lens plotted over a certain region, and is expressed as a conjugate absolute value of the wave function.

[ii] Characteristic Modes of the Present Invention

The characteristic modes of the present invention created with the object of addressing the problems the present invention is to solve described previously are expressed as follows using the terminology defined as described previously.

The first mode of the present invention provides a method for manufacturing a diffractive multi-focal ophthalmic lens capable of generating at least three focal points in an optical axis direction using a diffractive structure comprising a plurality of zones in a concentric circle form, the method being characterized by: generating a composite profile by overlapping at least two starting profiles comprising a plurality of zones in a concentric circle form; generating an adjusted profile by adjusting at least one of phase and amplitude with a zone of the composite profile as a subject in order to set an intensity distribution in the optical axis direction and determine optical characteristics; and manufacturing the diffractive multi-focal ophthalmic lens for which the adjusted profile is provided in at least a portion of the diffractive structure.

According to the method for manufacturing the diffractive multi-focal ophthalmic lens of this mode, it is possible to obtain a composite profile that can generate at least three focal points at any position on the optical axis by synthesizing a plurality of starting profiles. Also, as will be clear from the examples described later, by adjusting the phase or amplitude for each zone with the composite profile, it is possible to appropriately adjust and set the intensity distribution of the diffracted light in the optical axis direction. Because of that, for example, it is possible to not only adjust light intensity of each focal point that appears on the optical axis, or adjust the light intensity of minute peaks of multi-order light or the like generated secondarily at position other than the target focal points, but also to improve the intensity level while keeping the relative ratio of the light intensity at each focal point by suppressing the multi-order light. As a result, it is possible to effectively tune the optical characteristics, for example, by adjusting the visual performance such as of the clarity or the like of each focal point by adjusting the relative light intensity between each of the plurality of set focal points, or by suppressing problems such as halo or the like by suppressing the light intensity of peaks generated secondarily outside the focal points.

Specifically, with the method for manufacturing the diffractive multi-focal ophthalmic lens of this mode, the position of each focal point on the optical axis can be set with the starting profile zone as the subject, and it is possible to adjust the phase or amplitude with the zone of the composite profile as the subject without changing the set focal point position. Because of that, after setting the position of the requested plurality of focal points by adjusting the starting profile in advance, it is possible to do suitable tuning of the optical characteristics by adjusting the composite profile zones.

With this mode, it is possible to perform adjustment of the phase or amplitude of the composite profile with any zone as the subject, and possible to adjust the phase and/or amplitude for a portion of the zones, and when doing that, it is possible to adjust the phase and/or amplitude considering the plurality of zones in relation to each other. For example, as noted in modes 5, 6, 8 and the like described later, it is also possible to set such that the pattern of the phase or amplitude of the plurality of zones changes periodically, or as noted in mode 9 or the like described later, to have essentially the phase profile be integrated between the plurality of continuous zones. Furthermore, with this mode, it is possible to use separately phase adjustment and amplitude adjustment for mutually different zones with the composite profile.

Also, with this mode, the starting profiles are not limited to items for which the same phase or amplitude has been set for all the zones, and it is possible to have the blaze shape as the phase function be different for each of the zones, and possible to have the light transmittance as the amplitude function be different. Also, the phase function is not limited to being a blaze shaped item. Furthermore, each zone position of the composite profile is typically set corresponding to each zone position of the plurality of starting profiles that are mutually overlapped, but the overlapping region of the plurality of starting profiles does not have to extend over all the zone regions of the composite profile, and is acceptable as long as it is a region for which a plurality of starting profiles overlap at least at a portion of the composite profile.

Furthermore, it is not necessary for all the zones of the composite profile to be structured with a plurality of starting profiles overlapping. Specifically, a region provided with a plurality of starting profiles overlapping is not necessary over the entire lens optical region, and it is acceptable to provide it partially in the lens radial direction.

With the diffractive multi-focal ophthalmic lens constituted according to this mode, by being thinner than the refraction type, for example when using as an ophthalmic lens such as an intraocular lens, contact lens or the like, while maintaining the excellent points of the diffractive type multi-focal lens of reducing the burden on the patient, being easy to handle by the practitioner or the like, by improving the degree of freedom of tuning the optical characteristics such as the focal point position or the like, it is possible to put into practical use an ophthalmic lens with the high quality vision commensurate with the high level demanded by patients.

The second mode of the present invention is the method for manufacturing the diffractive multi-focal ophthalmic lens according to the first mode, wherein the at least two starting profiles all have a phase expressed as a blaze shaped function in relation to a lens radial distance in at least a portion of a region overlapped, and the phase of the composite profile is also expressed as a blaze shaped function.

According to the method for manufacturing the diffractive multi-focal ophthalmic lens of this mode, the mutually overlapping starting profiles and the composite profile generated using those are all expressed using a blaze shaped phase profile, so setting and adjustment of the phase profile of each zone of the composite profile obtained by overlapping the plurality of starting profiles is easy, and it is possible to further improve the optical characteristics with excellent diffraction efficiency based on the blaze shaped phase profiles. Specifically, in accordance with this mode, it is possible to set the first order diffraction efficiency to be sufficiently high by using a blaze shape that is typically called a sawtooth shape, and it is also possible to easily and precisely design the diffractive structure using a well known arithmetic expression.

With the method for manufacturing the diffractive multi-focal ophthalmic lens of this mode, as this blaze shaped phase function $\phi(r)$, the item shown with the third mode below can be preferably used, for example. By doing this, it is possible to express reliably the blaze shaped phase information with simple parameter, and thus possible to precisely and efficiently perform design of the diffractive structure.

Specifically, the third mode of the present invention is the method for manufacturing the diffractive multi-focal ophthalmic lens according to the second mode, wherein the blaze shaped function of the composite profile is expressed by Equation 6.

$$\phi(r) = \frac{\phi_i - \phi_{i-1}}{r_i - r_{i-1}} \times r + \frac{\phi_{i-1} \times r_i - \phi_i \times r_{i-1}}{r_i - r_{i-1}} + \tau \quad \text{[Equation 6]}$$

r: Radial distance from the lens center
$r_{i-1}$: Inner diameter of the ith zone (radius)
$r_i$: Outer diameter of the ith zone (radius)
$\phi_{i-1}$: Phase at the inner diameter (radius) position of the ith zone
$\phi_i$: Phase at the outer diameter (radius) position of the ith zone
τ: Phase shift Also, the fourth mode of the present invention is the method for manufacturing the diffractive multi-focal ophthalmic lens according to the third mode, wherein adjustment of the phase with the zone of the composite profile as the subject is performed by varying at least one of a phase constant h expressed by Equation 7 using $\phi_i$ and $\phi_{i-1}$ of Equation 6, and a phase shift τ of Equation 6.

$$h = \frac{\phi_{i-1} - \phi_i}{2\pi} \quad \text{[Equation 7]}$$

According to the method for manufacturing the diffractive multi-focal ophthalmic lens of this mode, by expressing the phase of the zones with the phase constant h and the phase shift τ, it is easier for the phase profile to be understood, and it is possible to more easily and efficiently perform phase adjustment. Specifically, it is possible to vary the tilt of the phase by the phase constant h, and possible to vary the vertical direction position of the phase using the phase shift τ. Furthermore, it is possible to determine the phase function of the blaze with the two parameters of the phase constant h and the phase shift, and by varying at least one of the phase constant or the phase shift, it is possible to have a design with good outlook.

The fifth mode of the present invention is the method for manufacturing the diffractive multi-focal ophthalmic lens according to the fourth mode, wherein when adjusting the phase of the composite profile, the adjusted profile is set so as to include the zones for which the phase constant h changes periodically in a radial direction.

The sixth mode of the present invention is the method for manufacturing the diffractive multi-focal ophthalmic lens according to the fourth or fifth mode, wherein when adjusting the phase of the composite profile, the adjusted profile is set so as to include the zones for which the phase shift τ changes periodically in a radial direction.

In accordance with the method for manufacturing the diffractive multi-focal ophthalmic lens of the fifth or sixth mode, by having zones with the periodically changing phase constant or phase shift set, it is possible to more efficiently adjust the peak intensity at specific focal point positions (addition power) with the light intensity distribution on the optical axis, for example. Also, with zone regions for which the phase constant h or the phase shift τ change periodically, it is also possible to realize imaging characteristics that are not dependent on the lens radial direction region position or the like.

The seventh mode of the present invention is the method for manufacturing the diffractive multi-focal ophthalmic lens according to any of the first to sixth modes, wherein adjustment of the amplitude of the composite profile is performed by adjusting a light transmittance in the zone of the composite profile.

According to this mode, for example by adjusting the light transmittance of a specific zone, while keeping the peak intensity of the light beams at a specific addition power roughly constant, by adjusting the peak intensity of the light beams at another addition power, or adjusting the light transmittance of the zone for each region in the lens radial direction, it is also possible to set so that the light beam intensity changes at the focal point position according to the effective lens aperture.

The eighth mode of the present invention is the method for manufacturing the diffractive multi-focal ophthalmic lens according to the seventh mode, wherein when adjusting the amplitude of the composite profile, the adjusted profile is set so as to include the zones for which the light transmittance changes periodically in a radial direction.

In accordance with this mode, the same as with the method for manufacturing the diffractive multi-focal ophthalmic lens of the fifth or sixth mode, it is possible to have efficient adjustment or the like of the peak intensity at specific focal point positions (addition power).

The ninth mode of the present invention is the method for manufacturing the diffractive multi-focal ophthalmic lens according to any of the first to eighth modes, wherein by adjusting at least one of the phase and amplitude of the composite profile, at least two zones positioned continuously in a radial direction in the composite profile are integrated.

According to the manufacturing method of this mode, while ensuring the plurality of addition powers set by the plurality of starting profiles, it is possible to further simplify the composite profile by adjusting the phase and amplitude. Because of that, for example when forming the composite profile as a relief form diffractive structure, it is possible to more easily perform manufacturing of the lens. Furthermore, it is also possible to inhibit loss such as by light scattering or the like by simplifying the profile, thus leading to improved image characteristics as well.

The tenth mode of the present invention is the method for manufacturing the diffractive multi-focal ophthalmic lens according to any of the first to ninth modes, wherein at least one of the starting profiles is a first starting profile having a zone pitch expressed by Equation 8 in at least a portion thereof.

$$r_n = \sqrt{r_1^2 + \frac{2\lambda(n-1)}{P_1}} \quad \text{[Equation 8]}$$

$r_n$: nth zone radius of the first starting profile
$r_1$: First zone radius of the first starting profile
$P_1$: Addition power of the first starting profile
n: Natural number
λ: Design wavelength According to this mode, by using the first starting profile equipped with a Fresnel pitch zone expressed by Equation 8, it is possible to make settings efficiently and with high precision using the Fresnel zone characteristics for setting of optical focal points using first order diffracted light and the like in addition to the optical focal points by the 0th order diffracted light. The zone pitch setting equations expressed with Equation 8 noted above and Equation 10 described later are called "general setting equations" with this specification.

The eleventh mode of the present invention is the method for manufacturing the diffractive multi-focal ophthalmic lens according to the tenth mode, wherein a first zone radius $r_1$ of the first starting profile is expressed by Equation 9.

$$r_1 = \sqrt{\frac{2\lambda}{P_1}} \qquad \text{[Equation 9]}$$

In accordance with this mode, it is possible to set the zone pitch of the first starting profile using a more simplified Fresnel pitch, and possible to more easily perform design of the diffractive structure, and also possible to efficiently check with good precision the diffracted light using a method such as simulation or the like.

Also, with the tenth and eleventh modes described above, in addition to the first starting profile, it is possible to use a Fresnel pitch zone as the second profile overlapped on that, and by doing that, it is possible to further improve the technical effect of greater efficiency through design, simulation or the like as described above. In specific terms, with the tenth and eleventh modes described above, it is possible to suitably use the twelfth mode or thirteenth mode hereafter.

Specifically, the twelfth mode of the present invention is the method for manufacturing the diffractive multi-focal ophthalmic lens according to the tenth or eleventh mode, wherein in addition to the first starting profile, a second starting profile having a zone pitch expressed by Equation 10 in at least a portion thereof is used as the starting profile.

$$r_m = \sqrt{r_1'^2 + \frac{2\lambda(m-1)}{P_2}} \qquad \text{[Equation 10]}$$

$r_m$: mth zone radius of the second starting profile
$r_1'$: First zone radius of the second starting profile
$P_2$: Addition power of the second starting profile
m: Natural number
λ: Design wavelength Also, the thirteenth mode of the present invention is the method for manufacturing the diffractive multi-focal ophthalmic lens according to the twelfth mode, wherein a first zone radius $r_1'$ of the second starting profile is expressed by Equation 11.

$$r_1' = \sqrt{\frac{2\lambda}{P_2}} \qquad \text{[Equation 11]}$$

Furthermore, the fourteenth mode of the present invention is the method for manufacturing the diffractive multi-focal ophthalmic lens according to the twelfth or thirteenth mode, wherein an addition power $P_2$ given by the second starting profile is expressed by a relational expression of Equation 12 using an addition power $P_1$ given by the first starting profile, a and b are mutually different natural numbers, and quotients when a and b are divided by a mutual greatest common divisor thereof are both an integer other than 1.

$$P_2 = \frac{a}{b} \times P_1 \qquad \text{[Equation 12]}$$

According to this mode, as is clear from the analysis and examples described hereafter, with the target diffractive multi-focal lens, it is possible to set at least three focal points for the focal point positions on the optical axis with a large degree of freedom of design and with good positional accuracy.

Specifically, by performing many experiments and studies, the inventors obtained the novel knowledge. That is, the synchronous conditions proposed previously by the invention described in Patent Document 1 were limited conditions in which a plurality of zones were synchronized with one zone. Meanwhile, the present invention makes it possible to further expand such synchronous conditions. Also, with this mode that was completed based on this knowledge, the ratio of the relative period count relationship of the mutually overlapping zone region of the first starting profile and the zone region of the second starting profile is obtained without limit compared to the invention noted in Patent Document 1, and by satisfying the condition that when a and b expressed by Equation 12 are used as a/b and that a/b must be other than X or 1/X (X is a natural number), it becomes possible to set the position of the intermediate focal point with a great degree of freedom of design. The examples described later can be referenced for specifics, but with the first zone profile that gives the addition power $P_1$ and the second profile that gives the addition power $P_2$, the addition power $P_1$ and $P_2$ are determined by Equation 12, and by constituting a zone profile with those overlapped and synthesized (composite profile), in addition to the addition power by the first starting profile, it is possible to easily and precisely additionally set an addition power of a different diopter value from that. Of course, with the other modes not included in the fourteenth mode of the present invention, it goes without saying that it is possible to make settings a/b as X or 1/X (X is a natural number).

With each of the modes of the present invention including this mode, a region for which first and second starting profiles are overlapped is not necessary over the entire lens optical region, and it is acceptable to provide it partially in the lens radial direction. For example, it is also possible to form the first starting profile over the entire lens optical region, and provide the second starting profile only on limited regions of the lens radial direction overlapping the first starting profile. Also, as is described later with the seventeenth, twenty-second, and twenty-third modes, in regions for which the first and second starting profiles are overlapped, it is also possible to further provide third, fourth, or fifth starting profiles suitably overlapping.

Also, according to this mode, with Equation 12 that determines the addition power $P_2$ given by the second zone profile, by having a and b be natural numbers, it is possible to mutually correlate the number of zones constituting the first and second starting profiles and the addition power $P_1$ and $P_2$ with natural numbers a and b as described later. Then, as a result, the profile that is overlapped and synthesized has a periodic zone repeated structure, and it becomes possible to obtain a diffractive multi-focal ophthalmic lens for which the generation of at least three focal points is reliably expressed over the entire region of the composite profile.

The relationship of the addition power of the first and second starting profiles with the number of zones constituting both profiles is described as follows. In a case when the diffractive structure is constituted from concentric circle zones having Fresnel pitches, for the first starting profile for which the addition power is $P_1$ and the second starting profile for which the addition power is $P_2$, by using Equation 9 and Equation 11, it is possible to express their respective zone radii $r_n$ and $r_m$ using Equation 13 and Equation 14 noted below.

$$r_n = \sqrt{\frac{2n\lambda}{P_1}} \qquad \text{[Equation 13]}$$

nth zone radius of the first starting profile $$r_m = \sqrt{\frac{2m\lambda}{P_2}}$$ [Equation 14]

mth zone radius of the second starting profile

When Equation 12 which is the relational expression of first starting profile addition power $P_1$ and second starting profile addition power $P_2$ is substituted with Equation 14, for the mth zone radius of the second starting profile, Equation 15 noted below is obtained.

$$r_m = \sqrt{\frac{2bm\lambda}{aP_1}}$$ [Equation 15]

Here, when $r_n$ and $r_m$ are made to be equal, from Equation 13 and Equation 15, the relational expression of Equation 16 noted below is obtained.

$$\sqrt{\frac{2n\lambda}{P_1}} = \sqrt{\frac{2bm\lambda}{aP_1}}$$ [Equation 16]

Furthermore, the relational expression of Equation 17 is obtained from Equation 16 noted above.

$$a \times n = b \times m$$ [Equation 17]

Here, n and m express zone numbers, and an integral value must be used. Also, a and b are natural numbers, so there will always be a combination of n and m for which both sides of the equation of Equation 17 are equal. In other words, for n and m, $a \times b \times \Omega$ ($\Omega$ is a natural number) which is a common multiple of a and b are divided respectively by a or b. Therefore, the zone radius that matches between the first and second starting profile can be specified using the zone numbers n and m with Equation 18 and Equation 19.

$$n = b \times \Omega (\Omega: \text{Natural number})$$ [Equation 18]

$$m = a \times \Omega (\Omega: \text{Natural number})$$ [Equation 19]

Said another way, the addition power of the second starting profile is expressed by Equation 12, and by having a and b be mutually different natural numbers, based on Equation 17, it is possible to set a zone count so that the zone radius between zone counts n and m match, in other words, so that the zones are synchronized.

For example, when the addition power of the second starting profile is $P_2 = P_1 \times (3/4)$, a=3 and b=4, from Equation 18 and Equation 19, the zone radii of the respective diffraction profiles for every zone count of n=4, 8, 12, ..., m=3, 6, 9, ... are synchronized and matched. By overlapping these profiles that can be synchronized with each other, the diffractive structure is constituted, and using this overlapping diffractive structure, the diffractive multi-focal ophthalmic lens having a focal point at a specific intermediate position is realized. Incidentally, in regards to this kind of theoretical relationship of addition power and the synchronous zone count, with the background art document group, the addition power is limited to 1/b, in other words, ½, ⅓, ¼, ..., because this is a structure by which a plural b-number of zones are allocated to one zone (a=1).

With the examples described later, the setting equation that determines the zone pitches with Equation 13 and Equation 14 will be called the "standard setting equation."

With this mode, in the lens radial direction, it is possible to have a synchronous structure by which the zone diameter of the first starting profile and the zone diameter of the second starting profile match with each other at specific zone positions, or can also have an asynchronous structure for which none of the zone diameters match. With profiles that have been overlapped and synthesized regardless of the matching or non-matching at a specific zone radius, it is possible to form a periodic structure, and with this structure, it is possible to obtain a diffractive multi-focal ophthalmic lens that can realize at least three focal points. With this periodic structure, it is not necessary for one period or greater to be formed in the lens radial direction, and it is possible to have the first and second starting profiles provided overlapping in a radial direction region that is not one full period. Specifically, as long as the target focal points are formed, a mode having only one zone in a region for which at least one of the first starting profile and the second starting profile is overlapped is also included.

Not limited to Equation 17 noted above, the numerical expression that specifies each mode of the present invention expresses the technical concept and is a design guideline, but it also generates errors with manufacturing processes and the like, for example. Because of that, as a requirement of the diffractive multi-focal ophthalmic lens provided by being manufactured with a structure according to each of the modes, it is sufficient as long as each numerical expression requirement is satisfied so as to achieve the target technical effect, and in regards to the dimensions of the diffractive structure with the diffractive multi-focal ophthalmic lens which is a product, a strict mathematical interpretation is not required, and it is sufficient as long as the optical operational effects that are the object of the modes are exhibited. For example, by setting a/b mathematically to an irrational number or the like, even with a mode for which there is not a complete mathematical match of the zone radii of designated periods that are synchronous in the radial direction, by there being a synchronous structure for which it is regarded as being essentially synchronous in a range for which there are no optical problems, it is possible to realize an ophthalmic multi-focal intraocular lens equipped with optical characteristics that achieve the object of the modes of the invention described above. Said another way, the technical concept of whether a/b is a rational number or irrational number being expressed mathematically is clear, but it is not necessary for the diffractive lens to be a specific structure according to the mathematically expression, and as long as the target optical characteristics are achieved, this can be thought of as being included in the scope of the fourteenth mode described above and any of the related modes described later.

Also, with the description above, with the first starting profile and the second starting profile, a mode was used for which the zone radii matched for each synchronous designated zone, but with the modes described above, it is not essential that the zone radii match for each synchronous zone count. For example, it is also possible to have the zone radii of synchronous positions be different from each other by having the zone radii shifted overall. Specifically, the synchronous conditions for the first starting profile and the second starting profile are sufficient as long as they are satisfied in terms of the period calculation, and for example it is not necessary for there to actually be synchronous positions in the lens radial direction such that the zone radii match with each other. Specifically, even if none of the zone radii match, it is sufficient to have the synchronous conditions mutually satisfied, including cases when the first starting profile and the second starting profile have a mutually synchronous relationship between mutually different radial direction zone positions.

The fifteenth mode of the present invention is the method for manufacturing the diffractive multi-focal ophthalmic lens according to the fourteenth mode, wherein a and b in Equation 12 are set to be $a/b > 1/2$.

According to this mode, for example by setting a relationship for which the addition power $P_2$ by the second starting profile in relation to the addition power $P_1$ by the first starting profile is set to be $P_2 > P_1 \times (1/2)$, the focal point set at a position in the intermediate between far and near can be set even closer to the near focal point, and for example with an ophthalmic lens, when near vision is used for reading, it is possible to set the focal point at a position suitable for viewing a personal computer screen. As is described also with the sixteenth mode described later, with this mode, the b-number of zone regions of the first starting profile and the a-number of zone regions of the second starting profile having a mutually synchronous relationship, for example, can be realized advantageously by setting with a relationship of $a/b > 1/2$.

The sixteenth mode of the present invention is the method for manufacturing the diffractive multi-focal ophthalmic lens according to the fourteenth or fifteenth mode, wherein in regards to a and b in Equation 12, a synchronous structure, for which a b-number of zone pitches that are continuous in the first starting profile and an a-number of zone pitches that are continuous in the second starting profile are mutually the same within the same region, is set for at least a portion of a region where the first starting profile and the second starting profile are overlapped.

With this mode, since zone pitches having a mutually synchronous structure for the first and second zone profiles are provided in the same overlapping region, it is possible to obtain a simplified composite profile structure, and to more clarify an overlapping structure, and the like.

The seventeenth mode of the present invention is the method for manufacturing the diffractive multi-focal ophthalmic lens according to any of the first to sixteenth modes, wherein the composite profile includes the diffractive structure for which in addition to the first starting profile and the second starting profile, a third starting profile is further overlapped on the same region.

According to this mode, in a region for which the first and second starting profiles for which mutually different addition power have been set, it is possible to further overlap and provide a third starting profile for which addition power different from that of the first and second starting profiles is set, and by doing that, possible to set four or more focal points, for example.

The eighteenth mode of the present invention is the method for manufacturing the diffractive multi-focal ophthalmic lens according to the seventeenth mode, wherein at least a portion of the third starting profile has a zone pitch given by Equation 20, and an addition power $P_3$ given by the third starting profile is different from both of the addition powers given by the first and second starting profiles.

$$r_q = \sqrt{r_1^{\prime\prime 2} + \frac{2\lambda(q-1)}{P_3}}$$ [Equation 20]

$r_q$: qth zone radius of the third starting profile
$r_1''$: First zone radius of the third starting profile
$P_3$: Addition power of the third starting profile
q: Natural number
$\lambda$: Design wavelength In accordance with this mode, in addition to the first and second zone profiles, the third zone profile also has at least a portion of the zone region set with the Fresnel pitch, and by doing that, when setting a composite profile with three types or more of zone profiles overlapping, it is possible to more easily and precisely perform optical characteristics adjustment and design.

The nineteenth mode of the present invention is the method for manufacturing the diffractive multi-focal ophthalmic lens according to the eighteenth mode, wherein a first zone radius $r_1''$ of the third starting profile is expressed by Equation 21.

$$r_1'' = \sqrt{\frac{2\lambda}{P_3}}$$ [Equation 21]

In accordance with this mode, the zone pitch setting equation of Equation 20 of the third zone profile shown with the eighteenth mode is expressed as a more simplified standard setting equation of Equation 22, and in addition to it being possible to easily perform design of the diffractive structure, it is also possible to precisely and efficiently confirm the diffracted light with a method such as simulation or the like.

$$r_q = \sqrt{\frac{2q\lambda}{P_3}}$$ [Equation 22]

The twentieth mode of the present invention is the method for manufacturing the diffractive multi-focal ophthalmic lens according to any of the seventeenth to nineteenth modes, wherein at least a portion of the composite profile has a synchronous structure for which, with $c_1$, $c_2$ and $c_3$ all being mutually different natural numbers, a $c_3$-number of zone pitches continuous in the third starting profile is the same as either a $c_1$-number of zone pitches continuous in the first starting profile or a $c_2$-number of zone pitches continuous in the second starting profile.

With the diffractive multi-focal ophthalmic lens manufactured according to this mode, the addition power $P_3$ of the third starting profile is set having the synchronous zone pitch expressed by the relationship $P_3 = (c_3/c_1) \times P_1$ or $P_3 = (c_3/c_2) \times P_2$ in relation to at least one of the addition power $P_1$ of the first starting profile or the addition power $P_2$ of the second starting profile.

With this mode, the first, second, and third starting profile zone regions can also respectively be set having an asynchronous relationship with one zone region of any other starting profile, but on the other hand, with the relational expression of $P_3 = (c_3/c_1) \times P_1$ or $P_3 = (c_3/c_2) \times P_2$, by having $c_3$, or $c_1$ or $c_2$ be 1, the third starting profile and the first or second starting profile can also be set to be synchronous having a relationship of a zone count of 1:X (or X:1) with X being a natural number. In this way, the synchronous relation of the zone region of the third starting profile in relation to the first and second starting profiles can be set with a high degree of freedom, and based on that, it is also possible to ensure a high degree of freedom for setting the focal point position given by the third starting profile.

The twenty-first mode of the present invention is the method for manufacturing the diffractive multi-focal ophthalmic lens according to any of the seventeenth to twentieth modes, wherein the addition power $P_2$ given by the second starting profile is expressed by a relational expression of Equation 12 using the addition power $P_1$ given by the first starting profile with a and b being mutually different natural numbers, while the addition power $P_3$ given by the third starting profile is determined by Equation 23 using the addition power $P_1$, and with a greatest common divisor being z for three integers of (b×e), (a×e), and (b×d) expressed using a, b, d, and e in Equation 12 and Equation 23, at least a portion of the composite profile has a synchronous structure for which a (b×e)/z-number of continuous zone pitches in the first starting profile, an (a×e)/z-number of continuous zone pitches in the second starting profile, and a (b×d)/z-number of continuous zone pitches in the third starting profile are mutually the same.

$$P_3 = \frac{d}{e} \times P_1 \qquad \text{[Equation 23]}$$

(d, e: Mutually different natural numbers)

With the diffractive multi-focal ophthalmic lens manufactured in accordance with this mode, by using the greatest common divisor z, based on the relationship of addition powers $P_1$, $P_2$, and $P_3$ given respectively by the first, second, and third starting profiles, it is possible to simplify and easily understand the synchronous relationship mutually between each zone pitch of the first, second, and third starting profiles. Also, by using the concept of this mode, for example as shown in example 8 described later, in cases when there is a different number of rational number denominators shown by Equation 12 and Equation 23 for setting the addition power of the first, second, and third starting profiles, by arranging the rational number denominators of each starting profile using the least common multiple, it is possible to understand the number of numerators as a number of synchronous zones of a repeated structure.

The twenty-second mode of the present invention is the method for manufacturing the diffractive multi-focal ophthalmic lens according to any of the seventeenth to twenty-first modes, wherein in addition to the first starting profile, the second starting profile, and the third starting profile, a fourth starting profile is also set, and the composite profile includes the diffractive structure which has the first, second, third, and fourth starting profiles overlapped on the same region.

The twenty-third mode of the present invention is the method for manufacturing the diffractive multi-focal ophthalmic lens according to the twenty-second mode, wherein in addition to the first starting profile, the second starting profile, the third starting profile, and the fourth starting profile, a fifth starting profile is also set, and the composite profile includes the diffractive structure which has the first, second, third, fourth, and fifth starting profiles overlapped on the same region.

With the diffractive multi-focal ophthalmic lens manufactured in accordance with the twenty-second and twenty-third modes of the present invention, by setting regions with four or more types of zone profiles having mutually different zone pitches overlapped for at least a portion of the diffractive structure, five or more or six or more focal point positions are set on the optical axis, so it is possible to ensure an even greater degree of freedom of adjusting the light intensity distribution on the optical axis, and for example it is possible to also make clearer the field of vision with a broader focal point position.

The twenty-fourth mode of the present invention is the method for manufacturing the diffractive multi-focal ophthalmic lens according to any of the first to twenty-third modes, wherein the diffractive structure comprises a relief structure reflecting an optical path length correlating to the phase.

For the relief that gives diffracted light with this mode, it is especially preferable to use a surface relief type such as an uneven type, a film thickness modulation type or the like. Also, by using the relief type diffractive structure in accordance with this mode, it is possible to improve the focal point design and precision.

As the relief in accordance with this mode, when forming an uneven surface such as the blaze shape described previously or the like, aside from a method using machining processing such as cutting or the like, in addition to processing of optical elements such as a glass substrate or the like using developing processing using electron beam resist and electron beams, it is possible to use various types of well known relief processing technology such as processing technology of the optical elements using repetition of a semiconductor process of film thickness lamination using photolithography and etching or the like.

The twenty-fifth mode of the present invention is the method for manufacturing the diffractive multi-focal ophthalmic lens according to any of the first to twenty-fourth modes, wherein it is possible to generate at least three focal points, and one of the at least three focal points is used for far vision, another focal point is used for near vision, and yet another focal point is used for intermediate vision.

With this mode, for example by following the fourteenth or fifteenth mode, between the far focal point using 0th order diffracted light and the near focal point using the addition power by the first zone profile, it is possible to set a intermediate focal point at any position further toward the far focal point or further toward the near focal point than the intermediate position, for example, with a high degree of freedom and a high precision level for setting the position. As a result, in addition to the focal point for far vision used for when driving a car or the like and the focal point for near vision used for reading or the like, it is possible to set a focal point for intermediate vision used for personal computer work or the like.

Also, by following the fifteenth mode noted above in particular, the focal point position for intermediate vision can also be set at a position near the focal point position for near vision, for example, so considering the user's living environment or the like, it is possible to suitably set each focal point position with a high degree of freedom so as to realize a focal point position suited for the user.

The twenty-sixth mode of the present invention is the method for manufacturing the diffractive multi-focal ophthalmic lens according to any of the first to twenty-fifth modes, wherein settings are made such that the focal point for far vision is given by a 0th order diffracted light of the diffractive structure, and the focal point for near vision and the focal point for intermediate vision are respectively given by a +1 order diffracted light of the first starting profile and the second starting profile.

With the diffractive multi-focal ophthalmic lens manufactured using this mode, with at least three focal points, the focal point for far, the focal point for near, and the focal point for intermediate region between those are given by the diffractive structure 0th order or +1 order diffracted light of the starting profile, so it is even easier to set the concentrated light and thus the light energy for each focal point. In addition, by performing zone adjustment of the composite profile according to the present invention, it is possible to easily and effectively control multi-order light, and as a result, while maintaining each focal point position light intensity and intensity ratio without significant loss, it is possible to improve the quality of vision by reducing multi-order light.

With the present invention of the modes described above, by providing regions with a plurality of starting profiles overlapped only in a specific region in the lens radial direction, it is possible to make settings such that optical characteristics of a plurality of focal points or a single focal point are exhibited with specific lens aperture regions.

In specific terms, for example, it is possible to make settings such that at least three focal points given by the region for which the first starting profile and the second starting profile are overlapped are generated with a lens aperture diameter of a predetermined setting diameter or greater. When using these kinds of settings, considering the fact that when the lens aperture diameter is made smaller, the depth of focus becomes deeper, for example, while three focal points are realized in a state for which the lens aperture diameter is larger and the depth of focus is shallower, by having one or two focal points in a state for which the lens aperture diameter is small and the depth of focus is deep, it is also possible to increase the light condensing rate of the light energy to those few focal point positions.

In particular by applying this to an ophthalmic lens, considering the fact that when the pupil contracts according to the level of brightness in the environment, the depth of focus becomes deeper, by essentially eliminating the optical characteristics by the composite profile at the optical diameter of diameter of 2 mm or less, for example, the focusing function for intermediate vision in fine weather outdoors or the like is suppressed, and it is possible to improve the contrast by efficiently ensuring the light energy volume at each required focal point for far and near vision. When applying this mode to an ophthalmic lens, it is preferable to set the setting diameter relating to the lens aperture diameter to a suitable value within a range of 0.8 to 3 mm, such as 2 mm or the like, for example, and to have the composite profile formed only in regions for which the diameter is greater than that.

In more specific terms, for example while a single starting profile is formed in a region of a smaller diameter than the setting diameter mentioned above, the composite profile made by overlapping the first and second starting profiles are formed on a region of a larger diameter than the setting diameter. As a result, in a state for which the effective aperture is small, while satisfying the imaging performances at points with different distances with a large depth of focus, while ensuring the light amount by increasing the light focusing efficiency to a focal point of a specific position, it is possible to ensure clarity of an image at points with different distances by increasing the number of focal points on the optical axis when the depth of focus has become shallow due to the effective aperture becoming larger.

Also, for example by using this for an ophthalmic lens, by setting the radial direction position of each starting profile and the composite profile formed by overlapping those taking into consideration the changes in pupil diameter with photopic vision, mesopic vision, and scotopic vision, it is also possible to substantially generate the necessary focal points according to the environment such as illuminance and the like. At that time, it is possible to suitably adjust and set at which position in the lens radial direction and at what level of radial direction width to provide the second starting profile that generates the composite profile by being overlapped on the first starting profile formed over the entire radial direction, for example, and by doing that, for example when using this for an ophthalmic lens, it is possible to further improve the degree of freedom for tuning of the conditions for the addition power to be manifested, the light intensity at the focal point position or the like used with intermediate vision, and the like.

With the starting profile, by making a variable setting for the first zone radius, while maintaining the Fresnel zone relational expression, it is possible to do change setting from the second zone pitch and thereafter. Because of that, by doing a variable setting of the first zone radius with the first starting profile and the second starting profile, it is possible to adjust the lens diameter region for which three focal points are generated, and at the radial direction end edge part of the lens radial direction region, settings that match the zone radii of the first and second starting profiles can also be easily realized.

Specifically, for example, when setting a partial overlapping region by providing the second starting profile overlapping the first starting profile only in a specific region of the lens radial direction, it is possible to match the first and second starting profile zone radii at the radial direction boundary line of the partial overlapping region and the non-overlapping region. In specific terms, for example, when partially overlapping the first and second starting profiles using the relationship of Equation 18 and Equation 19, it is possible to easily set matching zone radii on the boundary line of the overlapping regions. For example, by using the nth zone radius $r_n$ of the first starting profile expressed with Equation 8 and using a first zone diameter $r_1'$ of the second starting profile expressed with Equation 10, it is possible to have a synchronous structure for which the $b \times \Omega$ number of zone pitches from the (n+1)th of the first starting profile and the $a \times \Omega$ number of zone pitches from the second of the second starting profiles be the same, and in relation to the diffractive structure of the first starting profile, the diffractive structure of the second starting profile can be synchronized and overlapped at either of the inner circumference edge part or the outer circumference edge part of the diffractive structure by the second starting profile.

As a result, the inner circumference region up to the nth number of the diffractive structure by the first starting profile is made to be a non-overlapping region for which only the diffractive structure by the first starting profile is provided, and the zone region up to the number $n+b \times \Omega$ from the number n+1 of the diffractive structure by the first starting profile is an overlapping region for which is provided the composite profile made by overlapping of the first starting profile and the second starting profile. Also, over the entirety of the non-overlapping region and the overlapping region, the diffractive structure by the first starting profile is provided having a designated Fresnel zone pitch continuously in the radial direction. In fact, the diffractive structure by the second starting profile is created by forming a diffractive structure that coexists connected synchronously with the zone of the diffractive structure by the first starting profile at the boundary part of the overlapping region and the non-overlapping region.

The twenty-seventh mode of the present invention is a diffractive multi-focal ophthalmic lens capable of generating at least three focal points in an optical axis direction using a diffractive structure comprising a plurality of zones in a concentric circle form, the diffractive multi-focal ophthalmic lens being characterized in that: the diffractive structure comprises a composite profile which includes a phase profile that is dividable into a plurality of starting profiles being overlapped each other, and for which radial direction positions of the respective zones are set according to the plurality of starting profiles; and an adjusted profile is set for which at least one of the zones of the composite profile is a zone having a different phase and/or amplitude from an overlapping of the plurality of starting profiles.

With the diffractive multi-focal ophthalmic lens constituted according to this mode, the composite profile with the diffractive structure that realizes three or more focal points is not only a zone profile that can be identified as a phase profile for which are overlapped a plurality of starting profiles equipped with a diffractive structure providing the respective designated focal points, but also equipped together is a mode comprising an adjusted profile for which the phase profile is adjusted with the composite profile zones as the subject. Because of that, not only is it possible to efficiently understand, set and the like the focal point position or the light intensity ratio between each focal point depending on each starting point profile, but it is also possible to greatly ensure the level of freedom of setting the optical characteristics by adjusting the composite profile zone as the subject without depending on the starting profile. As a result, for example while maintaining the light intensity ratio or the like at the focal point position or between the focal points set depending on each starting profile, it is possible to easily and efficiently perform multi-order light control and the like such as that improves the light intensity at each focal point position with suppression of minute peaks on the optical axis of secondary multi-order light or the like due to high order diffracted light, and it is possible to realize the diffractive multi-focal ophthalmic lens that gives the target optical characteristics to a high degree.

With the diffractive multi-focal ophthalmic lens of this mode, with the composite profile, it is sufficient to be able to understand the optical characteristics with at least a portion of the radial direction divided into a plurality of starting profiles, and for example it is possible for the composite profile to be equipped together with a region comprising only single starting profiles and regions with a plurality of starting profiles overlapping at a portion in the radial direction. It is also desirable for the setting of the phase profile in relation to a designated zone of the composite profile to be performed by at least one of phase adjustment and amplitude adjustment as described later. A preferred specific mode is as noted with the example below.

The twenty-eighth mode of the present invention is the diffractive multi-focal ophthalmic lens of the twenty-seventh mode, wherein by the adjusted profile being set for which at least one of the zones of the composite profile is the zone having the different phase and/or amplitude from the overlapping of the plurality of starting profiles, compared to the phase profile comprising the overlapping of the plurality of starting profiles, a level of multi-order light for a light intensity distribution in the optical axis direction is suppressed. With this mode, the multi-order light for which the light intensity level is suppressed can be at least one order of the multi-order light other than the focal point settings on the optical axis, and it is not necessary for the level of all the multi-order light to be suppressed.

The twenty-ninth mode of the present invention is the diffractive multi-focal ophthalmic lens of the twenty-seventh or twenty-eighth mode, wherein in at least one of the plurality of starting profiles, at least a portion thereof has a Fresnel pitch. By using at least a Fresnel pitch, it is possible to make easier processes such as zone overlapping and phase and amplitude adjustment or the like.

The thirtieth mode of the present invention is the diffractive multi-focal ophthalmic lens of any of the twenty-seventh to twenty-ninth modes, wherein a radius of each zone that is a non-Fresnel pitch in a mode where the plurality of starting profiles are overlapped is substantially a Fresnel pitch in the adjusted profile by the plurality of zones being integrally consolidated.

By adjusting at least one of phase and amplitude of the composite profile, the diffractive multi-focal ophthalmic lens of this mode is identified as the one having the diffractive structure in which at least two zones that are continuous in the plurality of zones of the composite profile are integrated to be one zone. The composite profile for which at least one of phase and amplitude is adjusted has a different phase profile from that of the simple overlapping of the starting profiles. Because of that, while ensuring the generation of a plurality of focal points set by the zones of each starting profile, it is possible to simplify the phase profile by integrating the zones with the adjusted profile. Because of that, for example when forming the zone profile as a relief form diffractive structure, it is possible to perform manufacturing of the lens more easily. Furthermore, it is also possible to inhibit loss such as due to light scattering or the like by simplifying the profile, thus leading to improved imaging characteristics as well.

Furthermore, with the present invention, using a blaze shaped phase function is suitable because it gives high versatility, and makes optical calculation, manufacturing and processing easier, and provides high utility. In more specific terms, with the present invention, the thirty-first to thirty-third modes noted hereafter can be preferably used.

Specifically, the thirty-first mode of the present invention is the diffractive multi-focal ophthalmic lens of any of the twenty-seventh to thirtieth modes, wherein at least a portion of the phase of the adjusted profile is expressed as a blaze shaped function in relation to a lens radial distance.

Also, the thirty-second mode of the present invention is the diffractive multi-focal ophthalmic lens of any of the twenty-seventh to thirty-first modes, wherein in the plurality of starting profiles, at least a portion of each phase is expressed as a blaze shaped function in relation to a lens radial distance.

Furthermore, the thirty-third mode of the present invention is the diffractive multi-focal ophthalmic lens of the thirty-first or thirty-second mode, wherein the blaze shaped function is expressed by Equation 24.

$$\phi(r) = \frac{\phi_i - \phi_{i-1}}{r_i - r_{i-1}} \times r + \frac{\phi_{i-1} \times r_i - \phi_i \times r_{i-1}}{r_i - r_{i-1}} + \tau \qquad \text{[Equation 24]}$$

r: Radial distance from the lens center
$r_{i-1}$: Inner diameter of the ith zone (radius)
$r_i$: Outer diameter of the ith zone (radius)
$\phi_{i-1}$: Phase at the inner diameter (radius) position of the ith zone
$\phi_i$: Phase at the outer diameter (radius) position of the ith zone
$\tau$: Phase shift The thirty-fourth mode of the present invention relates to a series invention for which a plurality of lenses are combined into a set, and provides a diffractive multi-focal ophthalmic lens set comprising a plurality of types of diffractive multi-focal ophthalmic lenses combined into a series, each of the diffractive multi-focal ophthalmic lenses capable of generating at least three focal points in an optical axis direction using a diffractive structure comprising a plurality of zones in a concentric circle form, the diffractive structure comprising a composite profile which includes a phase profile that is dividable into a plurality of starting profiles being overlapped each other, and for which radial direction positions of the respective zones are set according to the plurality of starting profiles, wherein adjusted profiles are set in the respective diffractive multi-focal ophthalmic lenses for which, for each adjusted profile, at least one of the zones of the composite profile is a zone having a different phase and/or amplitude from an overlapping of the plurality of starting profiles, and light intensity distributions of the diffractive multi-focal ophthalmic lenses in the optical axis direction are made mutually different by settings of the adjusted profiles being mutually different.

According to this mode, it is possible to realize provision to the market as a series a suitable combination mode as needed of a plurality of types of lenses set with mutually different optical characteristics for example such as with (a) a type emphasizing near vision, (b) a type emphasizing intermediate vision, (c) a type emphasizing far vision, and (d) a uniformly visible type for each position. Also, by putting into series form in this way, when selling or using the diffractive multi-focal ophthalmic lens of the present invention noted in the modes described above, it is possible to handle these actions even more efficiently.

Effect of the Invention

As is clear from the description above, according to the present invention relating to the diffractive multi-focal ophthalmic lens and the manufacturing method thereof, while maintaining the basic characteristics of the plurality of focal point positions obtained by setting depending on the plurality of starting profiles that can be mutually overlapped and mutually divided and the light intensity ratio of those focal point positions, based on the phase information of each zone of the composite profile, it is possible to efficiently realize control of the light intensity distribution on the optical axis such as by improving the light intensity at each focal point or the like by suppressing the intensity of secondary multi-order light.

Also, according to the present invention relating to a set of diffractive multi-focal ophthalmic lenses, as noted above, it is possible to provide for use in the market the diffractive multi-focal ophthalmic lenses in a more efficient and easier to use state.

BRIEF DESCRIPTION OF THE DRAWINGS

FIGS. 4A-4C are graphs for describing the relative relationship of each phase function for starting profiles (1) and (2) having a blaze shaped phase function and the composite profile generated by overlapping those.

FIGS. 5A-5D are drawings relating to the composite profile of example 1 of the present invention, where FIGS. 5A and 5B show each phase profile of starting profiles (1) and (2) as the first and second zone profiles, FIG. 5C shows the composite profile as the overlapped phase profiles, and FIG. 5D is a graph showing the intensity distribution in the optical axis direction of the diffractive structure constituted by overlapping.

FIG. 7A shows the composite profile as overlapped phase profiles, and FIG. 7B is a graph showing the intensity distribution in the optical axis direction of the diffractive structure constituted by overlapping.

FIG. 8A is a graph of the phase function showing together the adjusted profile as example 2 obtained by changing and adjusting the phase constant of a specific zone with the composite profile shown in FIG. 7A and the composite profile before adjustment, and FIG. 8B is a graph showing together the light intensity distribution of the diffractive multi-focal lens having that adjusted profile and the light intensity distribution of the diffractive multi-focal lens having the composite profile before adjustment.

FIGS. 9A and 9B are drawings relating to the composite profile as example 3 of the present invention, where FIG. 9A shows the composite profile as overlapped phase profiles, and FIG. 9B is a graph showing the intensity distribution in the optical axis direction of the diffractive structure constituted by overlapping.

FIG. 11A is a graph of the phase function showing together the adjusted profile of example 4 obtained by adjusting the phase and amplitude with the composite profile of example 3 as the subject and the composite profile before adjustment, FIG. 11B is a front view showing in model form a lens for which transmittance was adjusted when doing amplitude adjustment of a specific zone, and FIG. 11C is a graph showing together the light intensity distribution of the diffractive multi-focal lens having the adjusted profile of this example and the light intensity distribution of the diffractive multi-focal lens having the composite profile before adjustment.

FIGS. 12A-12C are drawings relating to the diffractive multi-focal lens of example 5 of the present invention, where FIG. 12A is a graph of the phase function showing together the adjusted profile of example 5 obtained by adjusting the phase and amplitude with the composite profile of example 3 as the subject and the composite profile before adjustment, FIG. 12B is a front view showing in model form a lens for which transmittance was adjusted when doing amplitude adjustment of a specific zone, and FIG. 12C is a graph showing together the light intensity distribution of the diffractive multi-focal lens having the adjusted profile of this example and the light intensity distribution of the diffractive multi-focal lens having the composite profile before adjustment.

FIGS. 13A and 13B show each phase profile of starting profiles (1) and (2) as the first and second zone profiles, FIG. 13C shows the composite profile as the overlapped phase profiles, and FIG. 13D is a graph showing the intensity distribution in the optical axis direction of the diffractive structure constituted by overlapping.

FIGS. 15A and 15B are drawings relating to the diffractive multi-focal lens of example 7 of the present invention obtained by implementing a different phase adjustment to that of example 6 on the same composite profile as example 6, where FIG. 15A is a graph of the phase function showing together the adjusted profile as example 7 obtained by adjusting the phase of a specific zone with the composite profile shown in FIG. 13C and the composite profile before adjustment, and FIG. 15B is a graph showing together the light intensity distribution of the diffractive multi-focal lens having that adjusted profile and the light intensity distribution of the diffractive multi-focal lens having the composite profile before adjustment.

FIG. 16A is a front view of the image that appears on the retina, FIG. 16B is a graph of the intensity distribution on the image plane, and FIG. 16C is a Landolt ring image expressing visual performance.

FIG. 17A is a front view of the image that appears on the retina, FIG. 17B is a graph of the intensity distribution on the image plane, and FIG. 17C is a Landolt ring image expressing visual performance.

FIGS. 18A-18E show the results of simulation of the imaging characteristics projected on the retina surface in a state with the diffractive multi-focal lens constituted from the adjusted profile of example 7 set in the eye as an intraocular lens or contact lens, where FIG. 18A is a front view of the image that appears on the retina, FIG. 18B is a graph of the intensity distribution on the image plane, and FIG. 18C is a Landolt ring image expressing visual performance. FIG. 18D is a drawing showing the site at which the intensity distribution of the Landolt ring projected on the retina is displayed, and FIG. 18E is a drawing showing the intensity distribution of FIG. 16C, FIG. 17C, and FIG. 18C.

FIGS. 19A, 19B and 19C show each phase profile of starting profiles (1), (2) and (3) as the first, second and third zone profiles, FIG. 19D shows the composite profile as the overlapped phase profiles, and FIG. 19E is a graph showing the intensity distribution in the optical axis direction of the diffractive structure constituted by overlapping.

FIG. 21A is a graph showing the adjusted profile of example 8, FIG. 21B is a graph showing the zone profile of the standard Fresnel pitch, and FIG. 21C is a graph showing the adjusted profile of example 7.

FIGS. 22A-22F are drawings relating to the diffractive multi-focal lens of example 9 that has a standard Fresnel pitch by which four focal points can be generated by phase adjustment of specific zones, where FIG. 22A is a graph of the phase function of the adjusted profile, FIG. 22B is a graph of the light intensity distribution, and FIGS. 22C-22F are Landolt images showing the simulation results of visual performance when the diffractive multi-focal lens is set in the eye as an intraocular lens.

FIG. 23A is a graph showing the phase function of the adjusted profile, and FIG. 23B is a graph of the light intensity distribution.

FIG. 24A shows each phase profile of starting profiles (1) and (2) as the first and second zone profiles, FIG. 24B shows the composite profile as the overlapped phase profiles, and FIG. 24C is a graph showing the intensity distribution in the optical axis direction of the diffractive structure constituted by overlapping.

FIG. 25A is a graph of the phase function showing together the adjusted profile as example 11 obtained by adjusting the phase of a specific zone with the composite profile shown in FIG. 24B and the composite profile before adjustment, FIG. 25B is a graph showing together the light intensity distribution of the diffractive multi-focal lens having that adjusted profile and the light intensity distribution of the diffractive multi-focal lens having the composite profile before adjustment, and FIG. 25C is a drawing showing an enlarged view of the region enclosed by the dotted line in FIG. 25B.

FIG. 26A shows each phase profile of starting profiles (1) and (2)

as the first and second zone profiles, FIG. 26B shows the composite profile as the overlapped phase profiles, and FIG. 26C is a graph showing the intensity distribution in the optical axis direction of the diffractive structure constituted by overlapping.

FIG. 27A is a graph of the phase function showing together the adjusted profile as example 12 obtained by adjusting the phase of a specific zone with the composite profile shown in FIG. 26B and the composite profile before adjustment, FIG. 27B is a graph showing together the light intensity distribution of the diffractive multi-focal lens having that adjusted profile and the light intensity distribution of the diffractive multi-focal lens having the composite profile before adjustment, and FIG. 27C is a drawing showing an enlarged view of the region enclosed by the dotted line in FIG. 27B.

EMBODIMENTS FOR CARRYING OUT THE INVENTION

Figure 1:
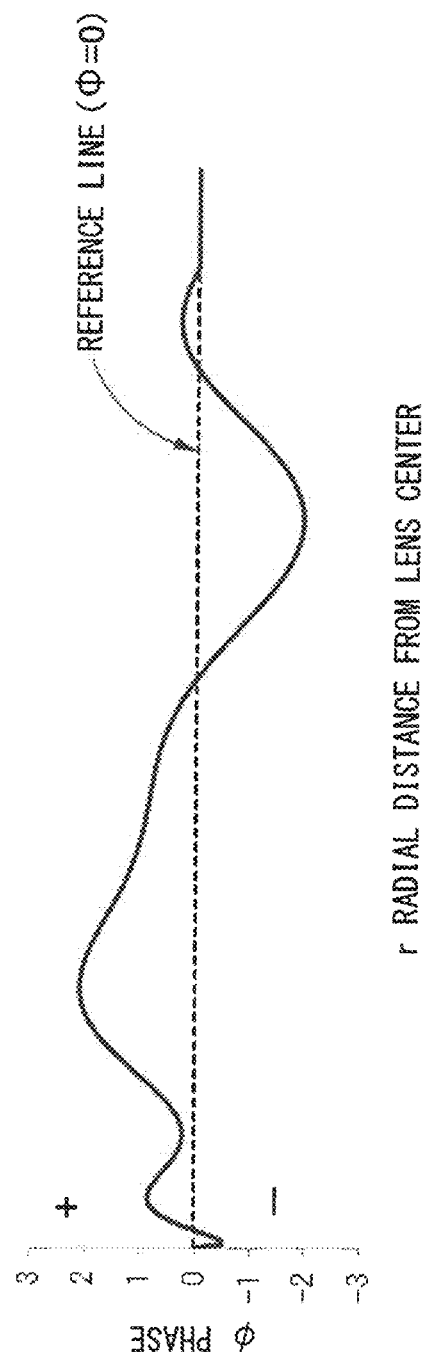
FIG. 1 is a graph of the phase function with the r-φ coordinate system expressing the relationship of the phase φ of the phase modulation structure provided in the diffractive lens with the lens radial direction position r.
Figures 2A, 2B, 2C, 2D:
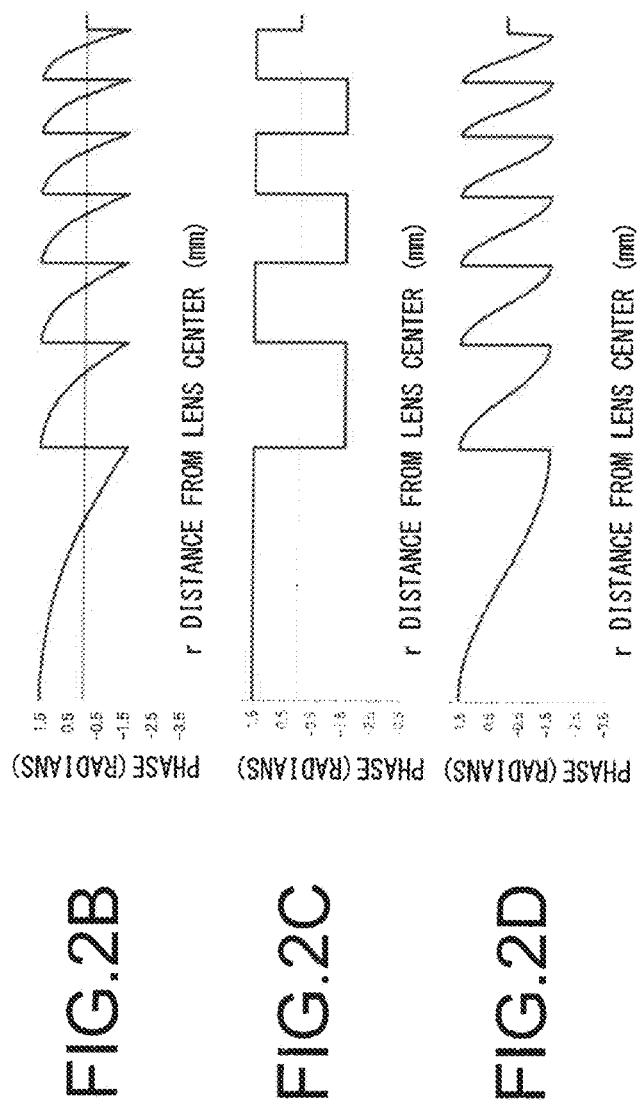
FIGS. 2A-2D show graphs with FIGS. 2A, 2B, 2C and 2D each showing the blaze as one mode of the phase function for the diffractive lens.
Figure 3:
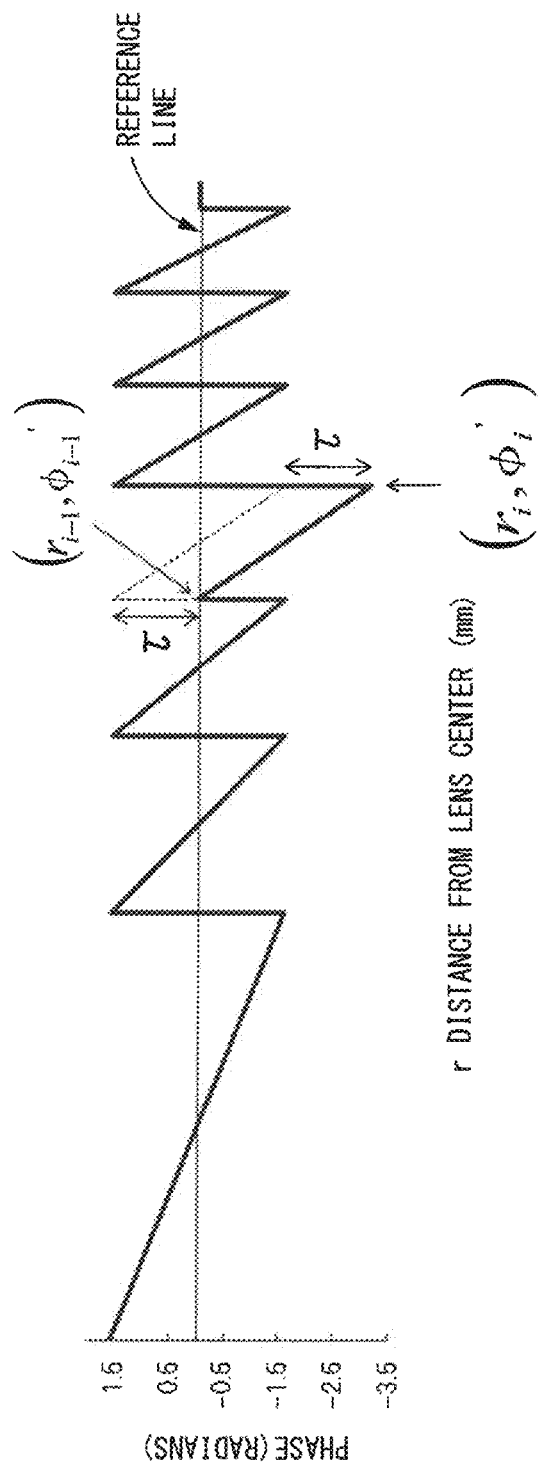
FIG. 3 is a graph using the phase shift τ to show the status when the blaze is shifted in the φ axis direction in relation to the reference line of the graph with the blaze phase function φ(r) expressed on the reference line.

Following, by showing and describing some examples as modes for carrying out the present invention, the present invention will be made clear in more specific terms.

Example Conditions and the Like

To start, we will describe the calculation simulation methods, conditions and the like used with the examples below. For the calculation software, an item was used that can calculate amplitude distribution and intensity distribution from each zone based on a diffraction integral equation derived from a theory known in the field called the scalar diffraction theory. Using this calculation software, we calculated the intensity distribution on the optical axis. A far point light source was set up as light source for calculation, and the calculation was performed on the assumption that parallel light beams in the same phase enter into the lens. Also, in the calculation, it was assumed that the media on the object and image sides are vacuum and the lens is an ideal lens having no aberration (light beams passing through the lens form an image at the same focal point regardless of the emitting position of the light). Further, the calculation was performed based on the assumption that the wavelength equals 546 nm and the refractive power of the lens for the 0th order diffracted light (basic refractive power) equals 7 D, considering ophthalmology or the like.

For the intensity distribution on the optical axis, the distance on the optical axis from the lens position as the base point to the image plane was converted to diopters, the focal point position of the 0th order diffracted light was standardized as 0 D, and intensity was plotted on that standardized scale. Unless otherwise noted, the lens aperture range for which the calculation simulation was performed was the region up to the zone number noted in each example.

In the examples using a blaze shaped phase, the mathematical formula for the blaze is based on Equation 3. In regards to the first, second, and so on starting profiles and composite profile, the phase of the blaze is noted using the phase constant h of Equation 4. Also, unless otherwise noted, the phase shift in Equation 3 is zero.

Also, for the zone diameter in the tables and drawings noted in the examples, the phase profiles are set as being centrosymmetric to the lens, and are shown across the radial direction region from the center of the lens cross section. Unless otherwise noted, the light transmittance when passing through the zone was 100%.

However, according to the method of the present invention, when manufacturing the diffractive multi-focal lens that is able to generate at least three focal points in the optical axis direction using the diffractive structure comprising a plurality of zones in a concentric circle form, typically, control of the optical characteristics settings is performed according to a mode including steps (A) to (E) below, and this mode was followed for each of the examples below.

(A) A step of preparing a plurality of starting profiles for which phase and amplitude for modulating the light that passes through the zone are given for each zone, comprising a plurality of zones in a concentric circle form.

(B) A step of having at least two of the starting profiles be overlapped in the same region in the zone radial direction to be one profile.

(C) A step of recording on the composite profile as one profile the zone positions of starting profiles overlapped with each other, and arranging the new phase and amplitude made by overlapping the phase and amplitude of the starting profiles in the corresponding zone radial direction on the composite profile.

(D) A step of determining the optical characteristics by setting the intensity distribution in the optical axis direction by adjusting at least one of the phase and amplitude of the composite profile for at least one of the zones recorded on the composite profile.

(E) A step of manufacturing the diffractive multi-focal lens for which the adjusted profile having the adjusted phase and amplitude is provided on at least a portion of the diffractive structure.

Example 1

(i) Preparation of the Composite Profile

First, we will describe the specifications of the diffractive lens equipped with the composite profile that is the base for adjusting at least one of the phase and amplitude according to the present invention. The diffractive lens has as a base an item showing imaging characteristics for which at least three focal points are generated at optional positions on the optical axis, and the image characteristics are given by using a diffractive structure having a composite profile for which two starting profiles (1) and (2) are overlapped on the same region.

Both starting profiles (1) and (2) have the phase function as a blaze shaped function, where with the starting profile (1), based on Equation 13 which is the standard setting equation, the zone pitch is determined such that the addition power $P_1$ is $P_1=4$ diopters (hereafter, diopter is abbreviated as D). With the starting profile (2), based on the standard setting equation of Equation 14, the zone pitch is determined such that the addition power $P_2$ is ¾ of $P_1$ with $P_2=3$ D. The phase constant of starting profiles (1) and (2) are respectively 0.48 and 0.39. The composite profile was obtained by both starting profiles having this profile being overlapped on the same region which is the overlapping region, and adding the phase. Details of the starting profiles and composite profile are shown in Table 1 and FIGS. 5A, 5B, and 5C.

TABLE 1

| Starting profile (1) Addition power $P_1 = 4$ D | | Starting profile (2) Addition power $P_2 = 3$ D | | Composite profile(Example 1) | | | | |
|---|---|---|---|---|---|---|---|---|
| Zone No. | Zone radius (mm) | Phase constant | Zone No. | Zone radius (mm) | Phase constant | Zone No. | Zone radius (mm) Outer radius | Inner radius | Phase (radians) | |
| $n$ | $r_n$ | $h$ | $m$ | $r$ | $h$ | $i$ | $r_i$ | $r_{i-1}$ | $\phi_i{'}$ | $\phi_{i-1}{'}$ |
| 1 | 0.5225 | 0.48 | 1 | 0.6033 | 0.39 | 1 | 0.5225 | 0 | −2.4049 | 2.7332 |
| 2 | 0.7389 | 0.48 | 2 | 0.8532 | 0.39 | 2 | 0.6033 | 0.5225 | −0.8436 | 0.6110 |
| 3 | 0.9050 | 0.48 | 3 | 1.0450 | 0.39 | 3 | 0.7389 | 0.6033 | −1.6123 | 1.6068 |
| 4 | 1.0450 | 0.48 | 4 | 1.2066 | 0.39 | 4 | 0.8532 | 0.7389 | −1.7932 | 1.4036 |
| 5 | 1.1683 | 0.48 | 5 | 1.3491 | 0.39 | 5 | 0.9050 | 0.8532 | −0.9441 | 0.6572 |
| 6 | 1.2798 | 0.48 | 6 | 1.4778 | 0.39 | 6 | 1.0450 | 0.9050 | −2.7332 | 2.0718 |
| 7 | 1.3824 | 0.48 | 7 | 1.5962 | 0.39 | 7 | 1.1683 | 1.0450 | −2.1524 | 2.7332 |
| 8 | 1.4778 | 0.48 | 8 | 1.7065 | 0.39 | 8 | 1.2066 | 1.1683 | −0.7535 | 0.8635 |
| 9 | 1.5675 | 0.48 | 9 | 1.8100 | 0.39 | 9 | 1.2798 | 1.2066 | −1.5421 | 1.6969 |
| 10 | 1.6523 | 0.48 | | | | 10 | 1.3491 | 1.2798 | −1.7584 | 1.4789 |
| 11 | 1.7329 | 0.48 | | | | 11 | 1.3824 | 1.3491 | −0.9168 | 0.6971 |
| 12 | 1.8100 | 0.48 | | | | 12 | 1.4778 | 1.3824 | −2.7332 | 2.0992 |
| | | | | | | 13 | 1.5675 | 1.4778 | −2.1379 | 2.7332 |
| | | | | | | 14 | 1.5962 | 1.5675 | −0.7404 | 0.8780 |
| | | | | | | 15 | 1.6523 | 1.5962 | −1.5284 | 1.7101 |
| | | | | | | 16 | 1.7065 | 1.6523 | −1.7437 | 1.4875 |
| | | | | | | 17 | 1.7329 | 1.7065 | −0.9091 | 0.7067 |
| | | | | | | 18 | 1.8100 | 1.7329 | −2.7332 | 2.1069 |

With this composite profile, there is a synchronous structure for which the zone radii of starting profiles (1) and (2) are matched using the zone numbers for which n=4Ω and m=3Ω (Ω is a natural number), and for which four continuous zone pitches of starting profile (1) and three continuous zone pitches of starting profile (2) are the same. As a result, the composite profile for which these profiles are synthesized has six blazes newly formed in the region having that synchronous structure. Therefore, a structure is exhibited which has phase profiles of a similar pattern repeated in zone units of the first to sixth, seventh to twelfth, thirteenth to eighteenth, and so on for the composite profile (hereafter called a repeated structure).

Also, these repeated structures give the basic information of which zones are adjusted when the following adjusting the phase and amplitude. The intensity distribution on the optical axis of the composite profile having that repeated blaze structure is shown in FIG. 5D.

As can be understood from FIG. 5D, with the intensity distribution of this composite profile, we can see that three main peaks are generated at positions of 0 D, 3 D, and 4 D. The peak generated at 0 D is based on the 0th order diffracted light of this composite profile, the 4 D peak is based on the +1 order diffracted light of starting profile (1), and the 3 D peak is based on the +1 order diffracted light of starting profile (2).

The features of this composite profile are in being able to generate focal points at positions correlating to the addition power set with the starting profile, and in being able to generate at least three focal points at any position by freely setting the addition power of the starting profile.

Because of that, if the diffractive multi-focal lens comprising the composite profile of this example is used for an ophthalmic lens, for example, it is possible to use the 0 D peak as the focal point for far vision, the 4 D peak as the peak for the focal point for ensuring visual power in near regions, and the 3 D peak as the focal point for ensuring visual power in the intermediate regions between these. Also, when using this example as an intraocular lens that is inserted and fixed in the human eye, focal points are respectively generated at positions of approximately 35 cm in front for the 4 D power for near use, and approximately 45 to 50 cm in front for the 3 D power for intermediate use. The focal point position for intermediate use correlates exactly to the distance at which a personal computer monitor screen is positioned, and thus, it is possible to make a multi-focal ophthalmic lens that is useful for work viewing monitor screens such as of a personal computer or the like in addition to for far and near distances.

However, in the intensity distribution diagram of FIG. 5D, we can see that a plurality of peaks is generated though the intensity of other than these main peaks is small. These peaks other than the main peaks are generated secondarily by interference of diffracted light of orders other than those noted above, and are called multi-order light or the like. When multi-order light is generated, incidental light is distributed to unnecessary points, the intensity of the target important peaks decreases, and thus, this is one cause of loss of brightness, clarity or the like when viewing an object.

Furthermore, the light that is imaged on the focal point positions of the multi-order light is mixed in the image plane of the target focal point position as stray light, and can be a cause of halo, glare or the like. Halo is a ring shaped or band shaped light that appear around a light source when viewing a far point light source at night, and when a halo is generated, there is sometimes a decrease in visibility at night. Halo reflects the distribution of light in noise form that is generated near the image plane center of the focal point position of 0th order diffracted light used as the focal point for far vision. This noise is generated by stray light such as the multi-order light noted above. The farther the generation position of the multi-order light on the optical axis becomes from the focal point position of the 0th order diffracted light, the broader a halo becomes.

With the diffractive lens having this kind of composite profile, the method for adjusting the phase with the composite profile to reduce multi-order light, and the diffractive multi-focal lens equipped with the adjusted profile obtained as a result are shown hereafter as example 1.

(ii) Generation of the Adjusted Profile Using Phase Adjustment

Figure 6A:
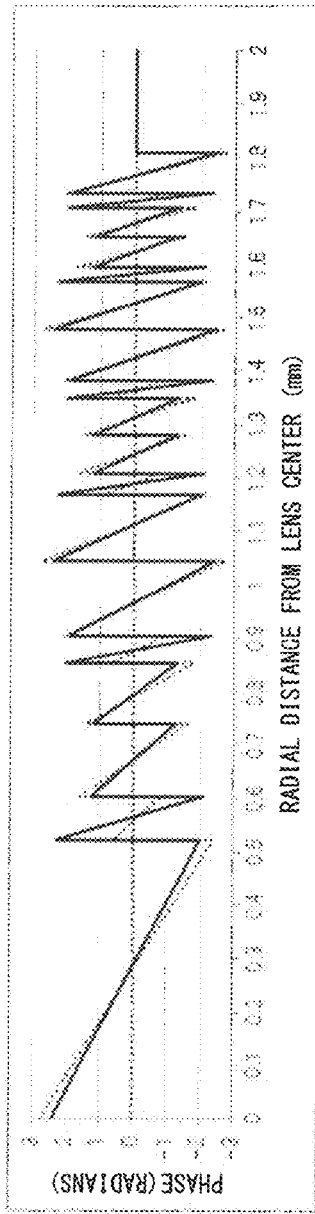
FIG. 6A is a graph of the phase function showing together the adjusted profile as example 1 obtained by changing and adjusting the phase constant of a specific zone with the composite profile shown in FIG. 5C and the composite profile before adjustment.

When doing adjustment, first, the phase is divided into the phase constant and the phase shift for each zone of the composite profile. By dividing in this way, it becomes possible to easily understand the details of the repeated structure of the phases of the composite profile using numerical value data, and to consistently perform the adjustment described later also using that variable. In specific terms, using the phases $\phi_{i-1}'$ and $\phi_i'$ of the composite profile described above, based on Equation 3 and Equation 4, the phase constant h for each zone was found as $h=(\phi_{i-1}'-\phi_i')/2\pi$, and the phase shift τ was found as $\tau=(\phi_{i-1}'+\phi_i')/2$. Table 2 shows the phase constant and phase shift found by separating in this way. In the table, column (A) shows the zone number of the composite profile. Column (B) shows the zone diameter (outer diameter and inner diameter) of each zone. Column (C) shows the phase constant when the blaze of the composite profile is decomposed into the phase constant and phase shift. Column (D) shows the phase shift of the composite profile. As described previously, with this example, the composite profile is synthesized so that starting profiles (1) and (2) have synchronous structures, so a similar blaze repeated structure is formed with the first to sixth, seventh to twelfth, and thirteenth to eighteenth zones, and for both the phase constant and the phase shift, almost the same numerical values are allocated to zones corresponding to this repeated structure.

to the seventh to twelfth and thirteenth to eighteenth. The significant change points from the composite profile are the points for which items for which the phase constant of the second, fifth, eighth, eleventh, fourteenth, and seventeenth zones was 0.23 to 0.26 were changed to 0.7. For the remainder, both the phase constant and the phase shift were changed in a range that remains at the fine adjustment level as shown in Table 2. This profile after adjustment is shown together with the composite profile in FIG. 6A. In the drawing, the solid line shows the adjusted profile after adjustment, and the dotted line shows the composite profile before adjustment.

Figure 6B:
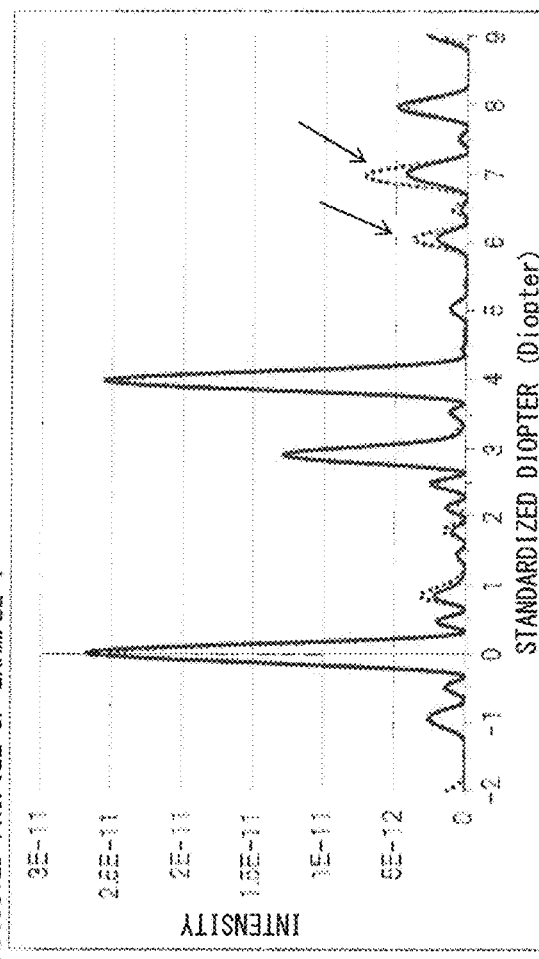
FIG. 6B is a graph showing together the light intensity distribution of the diffractive multi-focal lens having that adjusted profile and the light intensity distribution of the diffractive multi-focal lens having the composite profile before adjustment.

We can see from the drawing that for zones set so that the phase constant becomes larger, the tilt of the blaze becomes larger. The intensity distribution on the optical axis of the profile adjusted in this way is shown in FIG. 6B. From FIG. 6B, we can see that the appearance position of the major peaks and the intensity of the major peaks do not change before and after adjustment. We can see that what changes are the peaks of the multi-order light of the high order region, and with the composite profile, a number of the multi-order light peaks that stood out are reduced (see the arrow positions in the drawing).

By adjusting the phase in composite profile zone units in this way, it is possible to reduce the excess peaks due to multi-order light while maintaining the intensity distribution of peaks set with the composite profile. Specifically, obtaining the composite profile by overlapping the starting profiles initially with the present invention means preparing profiles that can generate at least three focal points at any position as

TABLE 2

| Zone No. i | Zone radius (mm) | | Composite profile (Example 1) | | Adjusted profile(Example 1) | | | |
|---|---|---|---|---|---|---|---|---|
| | Outer radius $r_i$ | Inner radius $r_{i-1}$ | Phase constant h | Phase shift τ | Phase constant h | Phase shift τ | After adjustment $\phi_i'$ | After adjustment $\phi_{i-1}'$ |
| 1 | 0.5225 | 0 | 0.818 | 0.1641 | 0.7 | 0.1885 | −2.0106 | 2.3876 |
| 2 | 0.6033 | 0.5225 | 0.232 | −0.1163 | 0.7 | 0.0942 | −2.1049 | 2.2934 |
| 3 | 0.7389 | 0.6083 | 0.512 | −0.0028 | 0.4 | 0 | −1.2566 | 1.2566 |
| 4 | 0.8532 | 0.7389 | 0.509 | −0.1948 | 0.4 | −0.0785 | −1.3352 | 1.1781 |
| 5 | 0.9050 | 0.8532 | 0.255 | −0.1435 | 0.7 | −0.1571 | −2.3562 | 2.0420 |
| 6 | 1.0450 | 0.9050 | 0.765 | −0.3307 | 0.7 | −0.2513 | −2.4504 | 1.9478 |
| 7 | 1.1683 | 1.0450 | 0.778 | 0.2904 | 0.7 | 0.1885 | −2.0106 | 2.3876 |
| 8 | 1.2066 | 1.1683 | 0.257 | 0.0550 | 0.7 | 0.0942 | −2.1049 | 2.2934 |
| 9 | 1.2798 | 1.2066 | 0.515 | 0.0774 | 0.4 | 0 | −1.2566 | 1.2566 |
| 10 | 1.3491 | 1.2798 | 0.514 | −0.1398 | 0.4 | −0.0785 | −1.3352 | 1.1781 |
| 11 | 1.3824 | 1.3491 | 0.257 | −0.1098 | 0.7 | −0.1571 | −2.3562 | 2.0420 |
| 12 | 1.4778 | 1.3824 | 0.769 | −0.3170 | 0.7 | −0.2513 | −2.4504 | 1.9478 |
| 13 | 1.5675 | 1.4778 | 0.775 | 0.2976 | 0.7 | 0.1885 | −2.0106 | 2.3876 |
| 14 | 1.5962 | 1.5675 | 0.258 | 0.0688 | 0.7 | 0.0942 | −2.1049 | 2.2934 |
| 15 | 1.6523 | 1.5962 | 0.515 | 0.0908 | 0.4 | 0 | −1.2566 | 1.2566 |
| 16 | 1.7005 | 1.6523 | 0.514 | −0.1281 | 0.4 | −0.0785 | −1.3352 | 1.1781 |
| 17 | 1.7329 | 1.7085 | 0.257 | −0.1012 | 0.7 | −0.1571 | −2.3562 | 2.0420 |
| 18 | 1.8100 | 1.7329 | 0.770 | −0.3132 | 0.7 | −0.2513 | −2.4504 | 1.9478 |
| (A) | (B) | | (C) | (D) | (E) | (F) | (G) | |

The phase constant and phase shift were changed according to Table 2 to perform phase adjustment. The phase of each zone with the adjusted profile obtained as a result is shown together in Table 2. Column (E) in the table shows the varied phase constant, and column (F) shows the varied phase shift. Also, column (G) shows the conversion of the blaze after the adjustment to peak and valley phases $\phi_{i-1}'$ and $\phi_i'$.

With this example, the adjusted value of the phase constant and the phase shift from the first to sixth is one pattern, and a combination of this numerical value was also allocated shown with this example. These excellent imaging characteristics make it possible to have an even more excellent diffractive multi-focal lens by reducing halo and glare by improving the resolution through further tuning with the composite profile zone as the subject, and this kind of effect can be said to be a technical effect that can not be achieved realistically by adjusting the zones as the subject with each starting profile.

In other words, when the phase or amplitude is modulated in zone units with the starting profiles as the subject, these modulated modes give an influence over two or more zones with the composite profile made by overlapping of the starting profiles, and a plurality of zones change in conjunction. Therefore, it is not possible to give as much freedom for the adjustment with the starting profiles as is possible with the zone unit adjustment with the composite profile.

Example 2

(i) Preparation of the Composite Profile

Figure 7A:
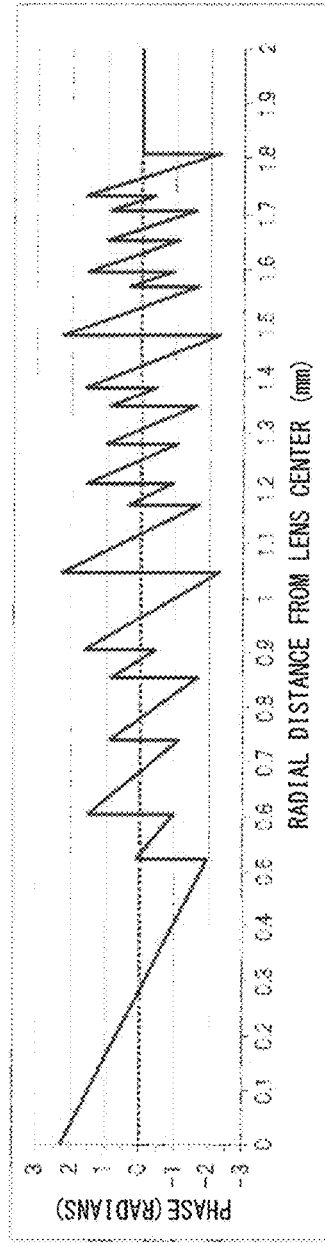
FIGS. 7A and 7B are drawings relating to the composite profile as example 2 of the present invention, where
Figure 7B:
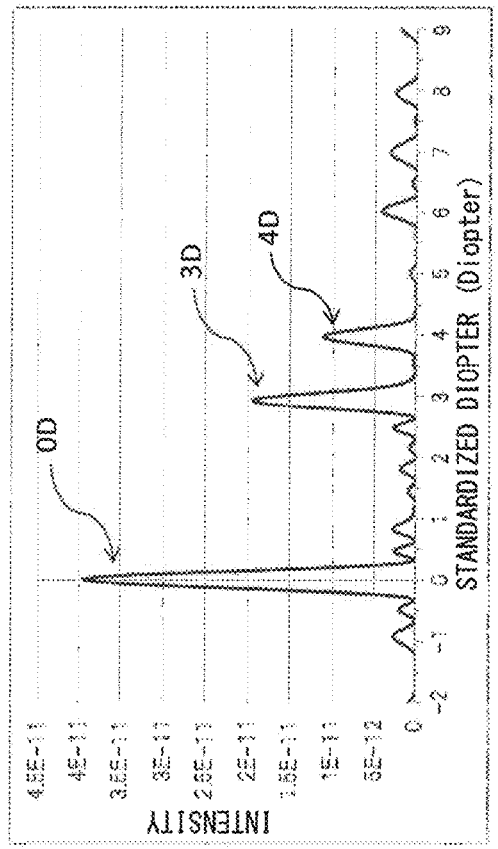

When acquiring the composite profile, the same starting profiles (1) and (2) as example 1 noted above were used other than that only the phase constant was varied. The phase constant of starting profiles (1) and (2) are respectively 0.33 and 0.4. The same as with example 1, the starting profiles (1) and (2) were overlapped in the same region to obtain the composite profile. The details of the composite profile are shown in Table 3 and FIG. 7A. Also, the intensity distribution on the optical axis of the composite profile of this example is shown in FIG. 7B.

ture. Also, for the intensity distribution of the composite profile, peaks are generated at the same position as example 1. However, because the phase constant is varied, the peak intensity differs from that of example 1 in accordance with that change.

With this example, 0 D has the highest intensity, with next being 3 D, and 4 D being set so as to be the smallest. The phase constant of starting profile (1) is set to be smaller than that of example 1 at 0.33, so the contribution of the +1 order light from the starting profile (1) is smaller in accordance with that phase constant variation, and as a result, the 4 D peak intensity is smaller. When that multi-focal lens is used as an ophthalmic lens, it can be a lens that emphasizes the visual performance of the 3 D medium region.

With the composite profile of this example as well, small peak groups are generated in high order regions (regions of approximately 6 to 8 D). The phase of the composite profile was adjusted to reduce the multi-order light. The diffractive

TABLE 3

| Starting profile (1) Addition power $P_1 = 4\,D$ | | Starting profile (2) Addition power $P_2 = 3\,D$ | | Composite profile(Example 2) Zone radius (mm) | | | | |
|---|---|---|---|---|---|---|---|---|
| Zone | | Zone | | | | | | |
| Zone No. | radius (mm) | Phase constant | Zone No. | radius (mm) | Phase constant | Zone No. | Outer radius | Inner radius | Phase (radians) | |
| n | $r_i$ | h | m | r | h | i | $r_i$ | $r_{i-1}$ | $\phi_i'$ | $\phi_{i-1}'$ |
| 1 | 0.5225 | 0.33 | 1 | 0.6033 | 0.4 | 1 | 0.5225 | 0 | −1.9566 | 2.2934 |
| 2 | 0.7389 | 0.33 | 2 | 0.8532 | 0.4 | 2 | 0.6033 | 0.5225 | −0.9943 | 0.1168 |
| 3 | 0.9050 | 0.33 | 3 | 1.0450 | 0.4 | 3 | 0.7389 | 0.6033 | −1.1437 | 1.5190 |
| 4 | 1.0450 | 0.33 | 4 | 1.2066 | 0.4 | 4 | 0.8532 | 0.7389 | −1.6471 | 0.9297 |
| 5 | 1.1683 | 0.33 | 5 | 1.3491 | 0.4 | 5 | 0.9050 | 0.8532 | −0.4584 | 0.8661 |
| 6 | 1.2798 | 0.33 | 6 | 1.4778 | 0.4 | 6 | 1.0450 | 0.9050 | −2.2934 | 1.6150 |
| 7 | 1.3824 | 0.33 | 7 | 1.5962 | 0.4 | 7 | 1.1683 | 1.0450 | −1.6977 | 2.2934 |
| 8 | 1.4778 | 0.33 | 8 | 1.7065 | 0.4 | 8 | 1.2066 | 1.1683 | −0.9324 | 0.3758 |
| 9 | 1.5675 | 0.33 | 9 | 1.8100 | 0.4 | 9 | 1.2798 | 1.2066 | −1.0717 | 1.5809 |
| 10 | 1.6523 | 0.33 | | | | 10 | 1.3491 | 1.2798 | −1.6197 | 1.0017 |
| 11 | 1.7329 | 0.33 | | | | 11 | 1.3824 | 1.3491 | −0.4304 | 0.8935 |
| 12 | 1.8100 | 0.33 | | | | 12 | 1.4778 | 1.3824 | −2.2934 | 1.6431 |
| | | | | | | 13 | 1.5675 | 1.4778 | −1.6828 | 2.2934 |
| | | | | | | 14 | 1.5962 | 1.5675 | −0.9233 | 0.3906 |
| | | | | | | 15 | 1.6523 | 1.5962 | −1.0577 | 1.5900 |
| | | | | | | 16 | 1.7065 | 1.6523 | −1.6131 | 1.0158 |
| | | | | | | 17 | 1.7329 | 1.7065 | −0.4225 | 0.9002 |
| | | | | | | 18 | 1.8100 | 1.7329 | −2.2934 | 1.6510 |

For the starting profiles (1) and (2) of the composite profile of this example, the same starting profiles (1) and (2) as with example 1 were used other than that the phase constant was varied, so the zone position of the composite profile is the same as that of example 1. On the other hand, the blaze step and peak and valley positions are different from those of example 1, but the same repeated structure is exhibited within the region having the synchronous strucmulti-focal lens equipped with the adjusted profile obtained as a result is shown hereafter as example 2.

(ii) Generation of the Adjusted Profile by Phase Adjustment

When doing adjustment, the same as with example 1, first, the phase information of the composite profile is divided into the phase constant and the phase shift, and the phase adjustment is performed based on that. The details of the divided composite profile phase constant and phase shift as well as the adjusted profile are shown in Table 4.

TABLE 4

| | Zone radius (mm) | | Composite profile (Example 2) | | Adjusted profile(Example 2) | | | |
|---|---|---|---|---|---|---|---|---|
| Zone No. | Outer radius | Inner radius | Phase constant | Phase shift | Phase constant | Phase shift | After adjustment | After adjustment |
| i | r | r | h | τ | h | τ | $\phi_i'$ | $\phi_{i-1}'$ |
| 1 | 0.5225 | 0 | 0.676 | 0.168 | 0.6 | 0.157 | −1.7279 | 2.0420 |
| 2 | 0.6033 | 0.5225 | 0.177 | −0.439 | 0 | −0.314 | −0.3142 | −0.3142 |

TABLE 4-continued

| | Zone radius (mm) | | Composite profile (Example 2) | | Adjusted profile(Example 2) | | | |
|---|---|---|---|---|---|---|---|---|
| Zone No. i | Outer radius r | Inner radius r | Phase constant h | Phase shift τ | Phase constant h | Phase shift τ | After adjustment $\phi_i'$ | After adjustment $\phi_{i-1}'$ |
| 3 | 0.7389 | 0.6033 | 0.424 | 0.188 | 0.4 | 0.094 | −1.1624 | 1.3509 |
| 4 | 0.8532 | 0.7389 | 0.410 | −0.359 | 0.4 | −0.314 | −1.5708 | 0.9425 |
| 5 | 0.9050 | 0.8532 | 0.211 | 0.204 | 0 | 0.047 | 0.0471 | 0.0471 |
| 6 | 1.0450 | 0.9050 | 0.622 | −0.339 | 0.7 | −0.785 | −2.9845 | 1.4137 |
| 7 | 1.1683 | 1.0450 | 0.635 | 0.298 | 0.6 | 0.471 | −1.4137 | 2.3562 |
| 8 | 1.2066 | 1.1683 | 0.208 | −0.278 | 0 | −0.126 | −0.1257 | −0.1257 |
| 9 | 1.2798 | 1.2066 | 0.422 | 0.255 | 0.4 | 0.173 | −1.0838 | 1.4294 |
| 10 | 1.3491 | 1.2798 | 0.417 | −0.309 | 0.4 | −0.236 | −1.4923 | 1.0210 |
| 11 | 1.3824 | 1.3491 | 0.211 | 0.232 | 0 | 0.079 | 0.0785 | 0.0785 |
| 12 | 1.4778 | 1.3824 | 0.627 | −0.325 | 0.7 | −0.785 | −2.9845 | 1.4137 |
| 13 | 1.5675 | 1.4778 | 0.633 | 0.305 | 0.6 | 0.471 | −1.4137 | 2.3562 |
| 14 | 1.5962 | 1.5675 | 0.209 | −0.266 | 0 | −0.126 | −0.1257 | −0.1257 |
| 15 | 1.6523 | 1.5962 | 0.421 | 0.266 | 0.4 | 0.188 | −1.0681 | 1.4451 |
| 16 | 1.7065 | 1.6523 | 0.418 | −0.299 | 0.4 | −0.220 | −1.4765 | 1.0367 |
| 17 | 1.7329 | 1.7065 | 0.211 | 0.239 | 0 | 0.094 | 0.0942 | 0.0942 |
| 18 | 1.8100 | 1.7329 | 0.628 | −0.321 | 0.7 | −0.314 | −2.5133 | 1.8850 |

When doing the adjustment of this example, the phase constant has the numerical value varied in the region of from the first to sixth zones, and that combination pattern was similarly set for from the seventh to twelfth and the thirteenth to eighteenth. In regards to the phase shift, the combination pattern between from the seventh to twelfth and from the thirteenth to eighteenth regions are almost the same, and the combination pattern with the first to sixth region was set to be slightly different. The adjusted profile is shown in FIG. 8A.

The characteristic feature of the adjusted profile of this example is that the phase constant of the second, fifth, eighth, eleventh, fourteenth, and seventeenth zones is h=0, and there is no tilt. The zones with h=0 are also one form of blaze with the present invention, and function as diffractive zones. The phase shift does not vary greatly from the composite profile setting value, and other than being adjusted by being slightly shifted to the minus side for the sixth and twelfth zones, was kept in the fine adjustment range. FIG. 8B shows the intensity distribution on the optical axis of this adjusted profile.

From FIG. 8B, we can see that the major peak generation positions and their intensity are kept almost the same before and after adjustment. On the other hand, we can see that there is a decrease in regards to small peaks due to multi-order light of the high order regions. Because of that, by the decrease in the multi-order light, when using the lens of this example as an ophthalmic lens, it is possible to obtain a diffractive multi-focal ophthalmic lens for which halo and glare are reduced when viewing far at night, while ensuring visual performance in the far, near, and intermediate regions.

Example 3

(i) Preparation of the Composite Profile

When acquiring the composite profile, the same starting profiles (1) and (2) as example 1 noted above were used other than that only the phase constant was varied. The phase constant of starting profiles (1) and (2) are respectively 0.47 and 0.47. The same as with example 1, the starting profiles (1) and (2) were overlapped in the same region to obtain the composite profile. The details of the composite profile are shown in Table 5 and FIG. 9A. Also, the intensity distribution on the optical axis of the composite profile of this example is shown in FIG. 9B.

TABLE 5

| Starting profile (1) Addition power $P_1 = 4 D$ | | | Starting profile (2) Addition power $P_2 = 3 D$ | | | Composite profile(Example 3) | | | | |
|---|---|---|---|---|---|---|---|---|---|---|
| | | | | | | | Zone radius (mm) | | Phase (radians) | |
| Zone No. n | Zone radius (mm) r | Phase constant h | Zone No. m | Zone radius (mm) r | Phase constant h | Zone No. i | Outer radius r | Inner radius r | $\phi_i'$ | $\phi_{i-1}'$ |
| 1 | 0.5225 | 0.47 | 1 | 0.6033 | 0.47 | 1 | 0.5225 | 0 | −2.5575 | 2.9531 |
| 2 | 0.7389 | 0.47 | 2 | 0.8532 | 0.47 | 2 | 0.6033 | 0.5225 | −1.1029 | 0.3956 |
| 3 | 0.9050 | 0.47 | 3 | 1.0450 | 0.47 | 3 | 0.7389 | 0.6033 | −1.6023 | 1.8502 |
| 4 | 1.0450 | 0.47 | 4 | 1.2066 | 0.47 | 4 | 0.8532 | 0.7389 | −2.0327 | 1.3508 |
| 5 | 1.1683 | 0.47 | 5 | 1.3491 | 0.47 | 5 | 0.9050 | 0.8532 | −0.7971 | 0.9204 |
| 6 | 1.2798 | 0.47 | 6 | 1.4778 | 0.47 | 6 | 1.0450 | 0.9050 | −2.9531 | 2.1560 |
| 7 | 1.3824 | 0.47 | 7 | 1.5962 | 0.47 | 7 | 1.1683 | 1.0450 | −2.2532 | 2.9531 |
| 8 | 1.4778 | 0.47 | 8 | 1.7065 | 0.47 | 8 | 1.2066 | 1.1683 | −1.0147 | 0.6999 |
| 9 | 1.5675 | 0.47 | 9 | 1.8100 | 0.47 | 9 | 1.2798 | 1.2066 | −1.5177 | 1.9884 |
| 10 | 1.6523 | 0.47 | | | | 10 | 1.3491 | 1.2798 | −1.9937 | 1.4354 |

TABLE 5-continued

| Starting profile (1) Addition power $P_1$ = 4 D | | Starting profile (2) Addition power $P_2$ = 3 D | | Composite profile(Example 3) | | | | |
|---|---|---|---|---|---|---|---|---|
| Zone No. n | Zone radius (mm) r | Phase constant h | Zone No. m | Zone radius (mm) r | Phase constant h | Zone No. i | Zone radius (mm) Outer radius r / Inner radius r | | Phase (radians) $\phi_i'$ / $\phi_{i-1}'$ |

| Zone No. n | Zone radius (mm) r | Phase constant h | Zone No. m | Zone radius (mm) r | Phase constant h | Zone No. i | Outer radius r | Inner radius r | $\phi_i'$ | $\phi_{i-1}'$ |
|---|---|---|---|---|---|---|---|---|---|---|
| 11 | 1.7329 | 0.47 | | | | 11 | 1.3824 | 1.3491 | −0.7641 | 0.9594 |
| 12 | 1.8100 | 0.47 | | | | 12 | 1.4778 | 1.3824 | −2.9531 | 2.1890 |
| | | | | | | 13 | 1.5675 | 1.4778 | −2.2357 | 2.9531 |
| | | | | | | 14 | 1.5962 | 1.5675 | −1.0018 | 0.7174 |
| | | | | | | 15 | 1.6523 | 1.5962 | −1.5012 | 1.9513 |
| | | | | | | 16 | 1.7065 | 1.6523 | −1.9842 | 1.4519 |
| | | | | | | 17 | 1.7329 | 1.7065 | −0.7548 | 0.9689 |
| | | | | | | 18 | 1.8100 | 1.7329 | −2.9531 | 2.1983 |

For the starting profiles (1) and (2) of the composite profile of this example, the same starting profiles (1) and (2) as with example 1 and 2 were used other than that the phase constant was varied, so the zone position of the composite profile is the same as that of example 1. On the other hand, the blaze step and peak and valley positions on the phase axis are different from those of example 1 and 2, but the same repeated structure is exhibited within the region having the synchronous structure. Also, for the intensity distribution of the composite profile, peaks are generated at the same positions as example 1 and 2. However, because the phase constant is varied, the peak intensity differs from that of example 1 and 2 in accordance with that change.

With the composite profile of this example, the phase constant of starting profiles (1) and (2) are set to be equal so as to have the peak intensity of the 0 D, 3 D, and 4 D positions be approximately the same. As shown in FIG. 9B, the peak of the respective positions have approximately the same intensity. When using the diffractive lens comprising this composite profile as an ophthalmic lens, it is possible for it to be a multi-focal ophthalmic lens with specifications for which the visual performance will be approximately the same in the respective far, near, and intermediate regions.

However, with the composite profile of this example, as can be seen from FIG. 9B, a peak group due to high intensity multi-order light is generated in the high order region. In particular, peaks at 7 D show intensity that is about half that of the major peaks, and generation of those high intensity peaks decreases the gain of the light of the major peaks, and there is the risk of aggravating halo and glare. The phase of the composite profile was adjusted to reduce the multi-order light. The diffractive multi-focal lens equipped with the adjusted profile obtained as a result is shown hereafter as example 3.

(ii) Generation of the Adjusted Profile by Phase Adjustment

When doing adjustment, the same as with example 1 and 2, first, the phase information of the composite profile is divided into the phase constant and the phase shift, and the phase adjustment is performed based on that. The details of the divided composite profile phase constant and phase shift as well as the adjusted profile are shown in Table 6.

TABLE 6

| | Zone radius (mm) | | Composite profile (Example 3) | | Adjusted profile(Example 3) | | | |
|---|---|---|---|---|---|---|---|---|
| Zone No. i | Outer radius $r_i$ | Inner radius r | Phase constant h | Phase shift τ | Phase constant h | Phase shift τ | After adjustment $\phi_i'$ | After adjustment $\phi_{i-1}'$ |
| 1 | 0.5225 | 0 | 0.877 | 0.198 | 0.7 | 0.157 | −2.0420 | 2.3562 |
| 2 | 0.6033 | 0.5225 | 0.239 | −0.354 | 0.7 | −0.314 | −2.5133 | 1.8850 |
| 3 | 0.7389 | 0.6033 | 0.549 | 0.124 | 0.1 | 0 | −0.3142 | 0.3142 |
| 4 | 0.8532 | 0.7389 | 0.539 | −0.341 | 0.7 | 0 | −2.1991 | 2.1991 |
| 5 | 0.9050 | 0.8582 | 0.273 | 0.062 | 0.7 | 0.063 | −2.1363 | 2.2619 |
| 6 | 1.0450 | 0.9050 | 0.813 | −0.399 | 0.7 | −1.257 | −3.4558 | 0.9425 |
| 7 | 1.1683 | 1.0450 | 0.829 | 0.350 | 0.7 | 0 | −2.1991 | 2.1991 |
| 8 | 1.2066 | 1.1683 | 0.273 | −0.157 | 0.7 | 0 | −2.1991 | 2.1991 |
| 9 | 1.2798 | 1.2066 | 0.550 | 0.210 | 0.1 | 0.157 | −0.1571 | 0.4712 |
| 10 | 1.3491 | 1.2798 | 0.546 | −0.279 | 0.7 | 0 | −2.1991 | 2.1991 |
| 11 | 1.3824 | 1.3491 | 0.274 | 0.098 | 0.7 | 0 | −2.1991 | 2.1991 |
| 12 | 1.4778 | 1.3324 | 0.818 | −0.382 | 0.7 | −0.942 | −3.1416 | 1.2566 |
| 13 | 1.5675 | 1.4778 | 0.826 | 0.359 | 0.7 | 0 | −2.1991 | 2.1991 |
| 14 | 1.5962 | 1.5675 | 0.274 | −0.142 | 0.7 | 0 | −2.1991 | 2.1991 |
| 15 | 1.6523 | 1.5962 | 0.549 | 0.225 | 0.1 | 0.157 | −0.1571 | 0.4712 |
| 16 | 1.7065 | 1.6523 | 0.547 | −0.266 | 0.7 | 0 | −2.1991 | 2.1991 |
| 17 | 1.7329 | 1.7065 | 0.274 | 0.107 | 0.7 | 0 | −2.1991 | 2.1991 |
| 18 | 1.8100 | 1.7329 | 0.820 | −0.377 | 0.7 | −0.628 | −2.8274 | 1.5708 |

Figure 10A:
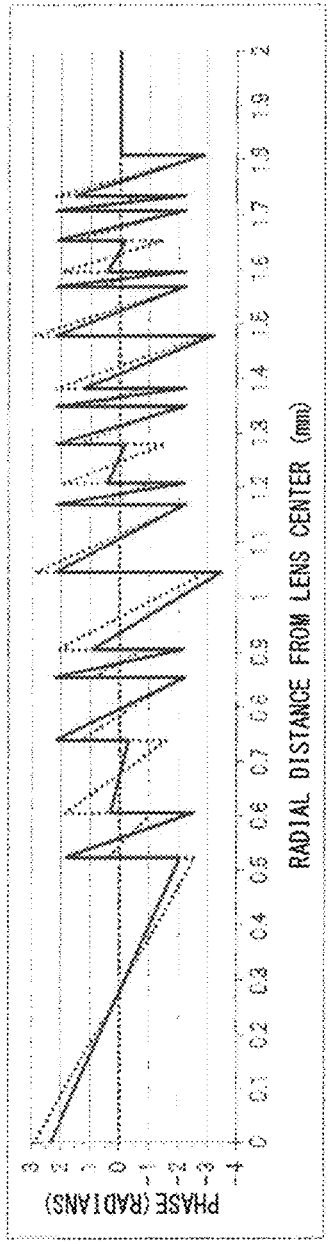
FIG. 10A is a graph of the phase function showing together the adjusted profile as example 3 obtained by changing and adjusting the phase constant of a specific zone with the composite profile shown in FIG. 9A and the composite profile before adjustment.

With this example, adjustment of the composite profile was performed while referencing the pattern of the divided phase constant and phase shift. The main change points are that the phase constants of the second, fifth, eighth, eleventh, fourteenth, and seventeenth zones that were around 0.24 to 0.27 were made to be a large value of 0.7, and the phase constants of the third, ninth, and fifteenth zones that were approximately 0.55 were made to be a small value of 0.1. There were also points such as significantly shifting the phase shift with the sixth and twelfth zones in the minus direction. Other than that was kept to a fine adjustment level. An adjusted profile diagram and the intensity distribution on the optical axis after the changes are respectively shown in FIGS. 10A and 10B.

Figure 10B:
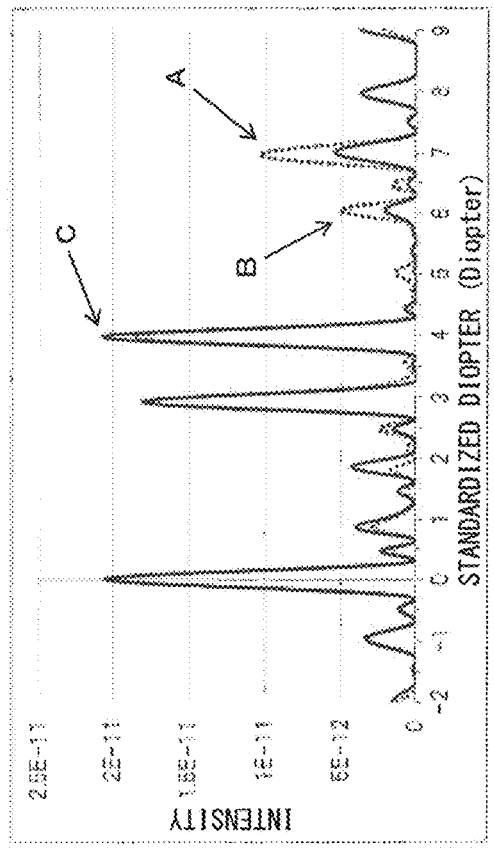
FIG. 10B is a graph showing together the light intensity distribution of the diffractive multi-focal lens having that adjusted profile and the light intensity distribution of the diffractive multi-focal lens having the composite profile before adjustment.

From FIG. 10B, we can see that the major peak generation positions and their intensity are kept almost the same before and after adjustment. On the other hand, we can see that the peak of approximately 7 D which was marked with the composite profile before adjustment (arrow A in FIG. 10B) decreased to approximately half. We can also see that the intensity of the approximately 6 D peak (arrow B in the same drawing) also significantly decreased. By decreasing the peaks by these multi-order lights, that portion is distributed to an increase in the 4 D peak intensity (arrow C), and this brings an effect of improving the gain of the light of the major peaks.

As a result of the light intensity distribution on the optical axis being controlled so as to be able to decrease multi-order light in this way and improve the light intensity at each focal point position that accompanies this, when using the lens of this example as an ophthalmic lens, it is possible to have a diffractive multi-focal lens for which halo and glare are reduced when viewing far at night, while ensuring vision power in far, near, and intermediate regions.

Example 4

With examples 1 to 3, we described the method for controlling multi-order light by adjusting the phase. With this example, we will describe the method for controlling when using amplitude adjustment together in addition to phase adjustment.

With this example, the same composite profile was used as with example 3 for the composite profile. Specifically, this example is an example when using together amplitude adjustment with the composite profile of example 3 as the subject. In specific terms, as shown in Table 7, the phase constant and phase shift are newly adjusted for the composite profile of example 3, and the light transmittance was varied for amplitude adjustment.

TABLE 7

| Zone No. i | Zone radius (mm) Outer radius $r_i$ | Zone radius (mm) Inner radius $r_{i-1}$ | Composite profile (Example 3) Phase constant h | Composite profile (Example 3) Phase shift τ | Adjusted profile (Example 4) Phase constant h | Adjusted profile (Example 4) Phase shift τ | Adjusted profile (Example 4) After adjustment $\phi_i'$ | Adjusted profile (Example 4) After adjustment $\phi_{i-1}'$ | Transmittance (%) |
|---|---|---|---|---|---|---|---|---|---|
| 1 | 0.5225 | 0 | 0.877 | 0.198 | 0.766 | 0.168 | −2.2394 | 2.5761 | 100 |
| 2 | 0.6033 | 0.5225 | 0.239 | −0.354 | 0.210 | −0.262 | −0.9228 | 0.3995 | 50 |
| 3 | 0.7389 | 0.6033 | 0.549 | 0.124 | 0.480 | 0.082 | −1.4265 | 1.5905 | 100 |
| 4 | 0.8532 | 0.7389 | 0.539 | −0.341 | 0.472 | −0.271 | −1.7537 | 1.2124 | 100 |
| 5 | 0.9050 | 0.8532 | 0.273 | 0.062 | 0.239 | 0.009 | −0.7412 | 0.7596 | 50 |
| 6 | 1.0450 | 0.9050 | 0.813 | −0.399 | 0.712 | −0.339 | −2.5761 | 1.8978 | 100 |
| 7 | 1.1683 | 1.0450 | 0.829 | 0.350 | 0.725 | 0.298 | −1.9804 | 2.5761 | 100 |
| 8 | 1.2066 | 1.1683 | 0.273 | −0.157 | 0.239 | −0.093 | −0.8439 | 0.6585 | 50 |
| 9 | 1.2798 | 1.2066 | 0.550 | 0.210 | 0.481 | 0.157 | −1.3545 | 1.6693 | 100 |
| 10 | 1.3491 | 1.2798 | 0.546 | −0.279 | 0.478 | −0.217 | −1.7188 | 1.2845 | 100 |
| 11 | 1.8824 | 1.3491 | 0.274 | 0.098 | 0.240 | 0.041 | −0.7131 | 0.7945 | 50 |
| 12 | 1.4778 | 1.3824 | 0.818 | −0.382 | 0.717 | −0.325 | −2.5761 | 1.9258 | 100 |
| 13 | 1.5675 | 1.4778 | 0.826 | 0.359 | 0.723 | 0.305 | −1.9656 | 2.5761 | 100 |
| 14 | 1.5962 | 1.5675 | 0.274 | −0.142 | 0.240 | −0.080 | −0.8324 | 0.6733 | 50 |
| 15 | 1.6523 | 1.5962 | 0.549 | 0.225 | 0.481 | 0.170 | −1.3404 | 1.6809 | 100 |
| 16 | 1.7065 | 1.6523 | 0.547 | −0.266 | 0.479 | −0.206 | −1.7103 | 1.2985 | 100 |
| 17 | 1.7329 | 1.7065 | 0.274 | 0.107 | 0.240 | 0.049 | −0.7052 | 0.8030 | 50 |
| 18 | 1.8100 | 1.7329 | 0.820 | −0.377 | 0.718 | −0.321 | −2.5761 | 1.9337 | 100 |

Amplitude adjustment correlates to varying the amplitude function A (x) of Equation 2 noted above. The specific adjustment of the amplitude can be performed by controlling the light transmittance. With this example, when light made incident on a designated zone with the composite profile is emitted without being blocked, the transmittance is 100%, and for example when it is 80%, the amplitude function is a multiple of 0.8, and when it is 50%, 0.5 is multiplied on the amplitude function, and a simulation was done by calculating the intensity distribution from the conjugate absolute value of the wave function comprising that amplitude function.

With this example, while the phase adjustment of the composite profile is kept at a fine adjustment level, there is joint use of amplitude adjustment for which the transmittance of the second, fifth, eighth, eleventh, fourteenth, and seventeenth zones is 50%. That transmittance setting can be implemented using a method such as reducing the transmittance by dyeing the concerned region using a dye or the like, for example.

Figure 11A:
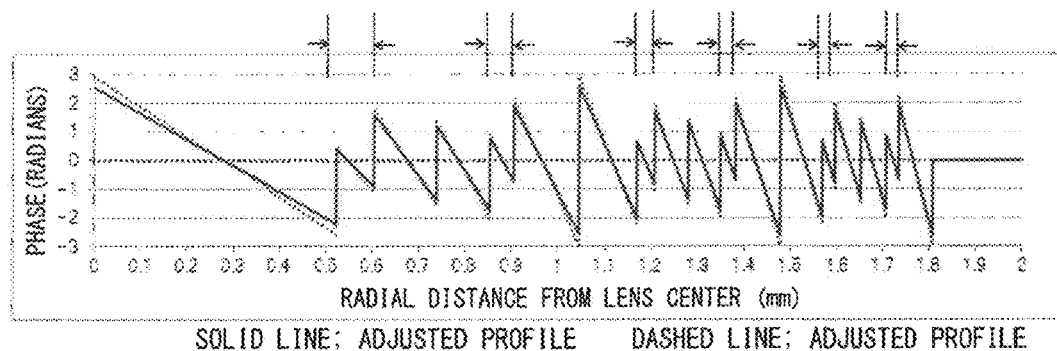
FIGS. 11A-11C are drawings relating to the diffractive multi-focal lens of example 4 of the present invention, where
Figure 11B:
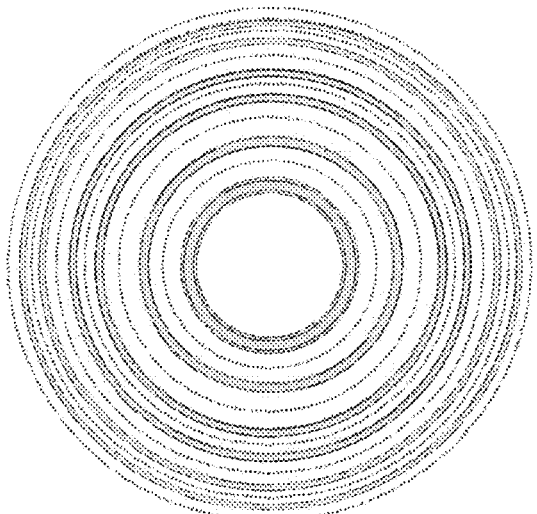

With this example, the adjusted profile obtained from the composite profile described above is shown in FIG. 11A. The phase adjustment is kept at a fine adjustment level, so there is no significant difference in the phase profile before and after adjustment. The zone with the transmittance at 50% is shown in the drawing. FIG. 11B shows a front view when the profile drawing is used as an actual lens. In the drawing, the gray region correlates to the zone for which the transmittance is 50%.

Figure 11C:
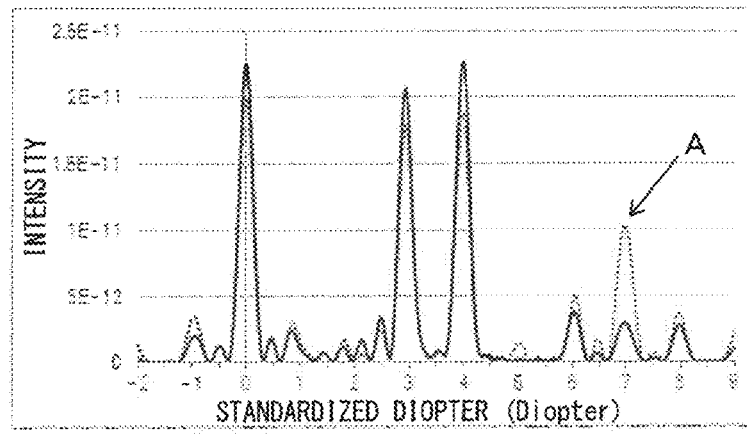

FIG. 11C shows a comparison of the intensity distribution in the optical axis direction of the adjusted profile of this example with that of the comparison profile. As can be understood from FIG. 11C, there is no change in the major peak generating position before and after adjustment. We can also see that there is no change in the intensity ratio of 0 D, 3 D, and 4 D, and that the intensity ratio of the composite profile is maintained.

Meanwhile, with the composite profile, the marked peak of approximately 7 D (arrow A) was further reduced even more than with example 3, and we can see that it was reduced to about ¼. Also, the significant reduction amount of the multi-order light peak is distributed to an increase in intensity of the major peak, and we can see that the respective intensity of the major peaks of 0 D, 3 D, and 4 D became larger.

When an item for which amplitude adjustment is used together in this way is used as an ophthalmic lens, there is an increase in the gain of each focal point peak while reducing halo and glare, so there is further improvement in clarity of visual performance and the like of each focal point position.

Example 5

With this example, the same as with example 4, this is a specific example when using amplitude adjustment together in addition to phase adjustment. With example 4, we described an example of performing amplitude adjustment with the transmittance at 50%, but with this example, we will describe a case when transmittance is 0%, in other words, of using together amplitude adjustment such as that completely blocks the transmission of light.

Specifically, with this example, with the same composite profile as example 3 as the subject, phase and amplitude adjustment of that profile were performed. To vary the amplitude adjustment conditions, phase adjustment was implemented again so as to correspond to that amplitude adjustment. The details of that adjusted profile are shown in Table 8.

such as blocking the light completely by coating a pigment or the like on the concerned region, for example.

The adjusted profile of this example is shown in FIG. 12A. Compared to the composite profile, the overall phase constant was set to be small, so the profile blaze step is a little smaller by that amount. The zone with the transmittance at 0% is shown in the drawing. FIG. 12B shows a front view when the profile drawing is actually used as a lens. In the drawing, the blacked out region correlates to the zone for which the transmittance is 0%.

FIG. 12C shows a comparison of the intensity distribution in the optical axis direction of the adjusted profile of this example with that of the comparison profile. As can be understood from FIG. 12C, there is no change in the major peak generating position before and after adjustment. We can also see that there is also no change in the intensity ratio of 0 D, 3 D, and 4 D, and that the intensity ratio of the composite profile is maintained.

Meanwhile, with the composite profile, the marked multi-order light peak was further reduced even more than with example 4, and we can see in particular that the peak of approximately 7 D that stood out (arrow A) was reduced to close to zero. Also, a reduction effect worked for almost all the multi-order light peaks, and the amount of reduction of these peaks was redistributed to an intensity increase in the major peaks, and we can see this brought a significant increase in gain for all the major peaks.

The general trend is for gain to decrease when there is a zone for which the transmittance is zero, but the trend with this example is different, with a significant increase in gain even while there is a zone with transmittance of zero. This shows that the adjustment conditions of this example are conditions that make it possible to lead diffracted light to the major focal point positions with high efficiency and without waste.

TABLE 8

| Zone No. | Zone radius (mm) | | Composite profile (Example 3) | | Adjusted profile(Example 5) | | | | Transmittance (%) |
| --- | --- | --- | --- | --- | --- | --- | --- | --- | --- |
| | Outer radius r | Inner radius r | Phase constant h | Phase shift τ | Phase constant h | Phase shift τ | After adjustment $\phi_i'$ | After adjustment $\phi_{i-1}'$ | |
| 1 | 0.5225 | 0 | 0.877 | 0.198 | 0.656 | 0.139 | −1.921 | 2.199 | 100 |
| 2 | 0.6033 | 0.5225 | 0.239 | −0.354 | 0.182 | −0.170 | −0.743 | 0.403 | 0 |
| 3 | 0.7389 | 0.6033 | 0.549 | 0.124 | 0.411 | 0.040 | −1.251 | 1.331 | 100 |
| 4 | 0.8532 | 0.7389 | 0.539 | −0.341 | 0.406 | −0.200 | −1.475 | 1.074 | 100 |
| 5 | 0.9050 | 0.8532 | 0.273 | 0.062 | 0.204 | −0.043 | −0.685 | 0.599 | 0 |
| 6 | 1.0450 | 0.9050 | 0.813 | −0.399 | 0.611 | −0.280 | −2.199 | 1.639 | 100 |
| 7 | 1.1683 | 1.0450 | 0.829 | 0.350 | 0.622 | 0.246 | −1.708 | 2.199 | 100 |
| 8 | 1.2066 | 1.1683 | 0.273 | −0.157 | 0.205 | −0.028 | −0.673 | 0.617 | 0 |
| 9 | 1.2798 | 1.2066 | 0.550 | 0.210 | 0.412 | 0.105 | −1.191 | 1.400 | 100 |
| 10 | 1.3491 | 1.2798 | 0.546 | −0.279 | 0.410 | −0.155 | −1.444 | 1.134 | 100 |
| 11 | 1.3824 | 1.3491 | 0.274 | 0.098 | 0.206 | −0.016 | −0.662 | 0.630 | 0 |
| 12 | 1.4778 | 1.3824 | 0.818 | −0.382 | 0.615 | −0.268 | −2.199 | 1.663 | 100 |
| 13 | 1.5675 | 1.4778 | 0.826 | 0.359 | 0.620 | 0.252 | −1.695 | 2.199 | 100 |
| 14 | 1.5962 | 1.5675 | 0.274 | −0.142 | 0.206 | −0.017 | −0.663 | 0.629 | 0 |
| 15 | 1.6523 | 1.5962 | 0.549 | 0.225 | 0.412 | 0.115 | −1.180 | 1.410 | 100 |
| 16 | 1.7065 | 1.6523 | 0.547 | −0.266 | 0.411 | −0.146 | −1.436 | 1.145 | 100 |
| 17 | 1.7329 | 1.7065 | 0.274 | 0.107 | 0.206 | −0.009 | −0.656 | 0.637 | 0 |
| 18 | 1.8100 | 1.7329 | 0.820 | −0.377 | 0.616 | −0.265 | −2.199 | 1.669 | 100 |

The phase adjustment of this example was performed so as to make the overall phase constant smaller. In addition to that phase adjustment, used together was amplitude adjustment such that the transmittance of the second, fifth, eighth, eleventh, fourteenth, and seventeenth zones is 0%. The transmittance setting can be implemented with a method Therefore, when the diffractive multi-focal lens based on the adjusted profile of this example is used as an ophthalmic lens, it is possible to have an ophthalmic lens with further reduction of halo and glare, and also to be useful as an ophthalmic lens that can realize even sharper visual performance in all regions of far, near, and intermediate with significantly increased gain of each major peak.

Example 6

Next, we will describe using the example below as an example of adjusting at least one of phase and amplitude with an item for which the composite profile specifications were changed by changing the addition power of the starting profile (2). First, example 6 is a specific example of a mode of changing the type of the composite profile for adjustment.

(i) Preparation of the Composite Profile

When acquiring the composite profile, both starting profiles (1) and (2) have the phase function as a blaze shaped function, where based on Equation 13 and Equation 14 which are standard setting equations, the respective zone pitches are determined such that with the starting profile (1), the addition power $P_1$ is $P_1=4$ D, and with the starting profile (2), it is determined such that the addition power $P_2$ is ⅔ of $P_1$ with $P_2=2.666$ D. The phase constant of starting profiles (1) and (2) are respectively 0.4 and 0.4.

Figure 13A:
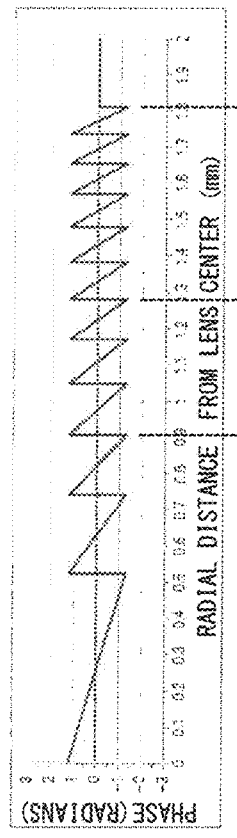
FIGS. 13A-13D are drawings relating to the composite profile as example 6 of the present invention, where
Figure 13B:
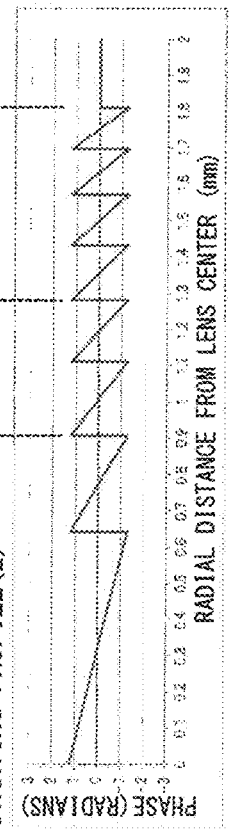
Figure 13C:
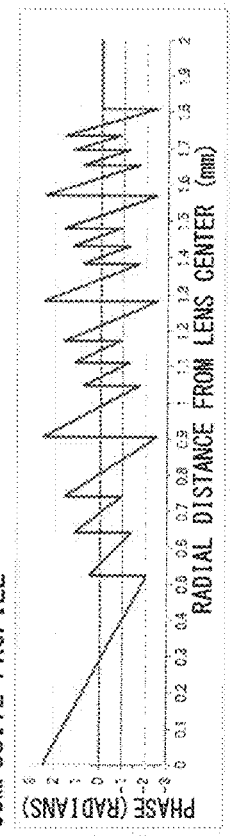

Also, the composite profile was obtained by overlapping both starting profiles (1) and (2) having this profile on the same region and adding the phase. The details of starting profiles (1) and (2) and the composite profile are shown in Table 9 and FIGS. 13A, 13B, and 13C.

D is based on the 0th order diffracted light of this composite profile, the 4 D peak is based on the +1 order diffracted light of starting profile (1), and the 2.67 D peak is based on the +1 order diffracted light of starting profile (2).

The difference between the composite profile of this example and that of the group of previously noted examples is the point that the addition power of starting profile (2) is changed, and with this example, by setting the addition power of starting profile (2) to 2.67 D, even the composite profile definitely has a peak generated at the point of 2.67 D. We can see that in this way, it is possible to generate at least three focal points freely simply by changing the addition power of the starting profile.

Also, the intensity distribution of the composite profile of this example has the 0 D peak intensity as the highest, and while the 2.67 and 4 D peaks are lower than that, they became equal. When using the diffractive lens comprising that profile as an intraocular lens, the 0 D peak for far vision is the highest, and the 4 D and 2.67 D peaks for near vision and intermediate vision are almost equal, so this becomes standard as the specification of an actual intraocular lens for which far vision is normally the most important. For a patient using this lens, far vision is ensured, it is possible to

TABLE 9

| Starting profile (1) Addition power $P_1 = 4$ D | | Starting profile (2) Addition power $P_2 = 2.666$ D | | Composite profile(Example 6) | | | | |
|---|---|---|---|---|---|---|---|---|
| Zone No. | Zone radius (mm) | Phase constant | Zone No. | Zone radius (mm) | Phase constant | Zone No. | Zone radius (mm) Outer radius | Zone radius (mm) Inner radius | Phase (radians) |
| n | $r_n$ | h | m | $r_m$ | h | i | $r_i$ | $r_{i-1}$ | $\phi_i'$ | $\phi_{i-1}'$ |
| 1 | 0.5225 | 0.4 | 1 | 0.6399 | 0.4 | 1 | 0.5225 | 0 | −2.0521 | 2.5133 |
| 2 | 0.7389 | 0.4 | 2 | 0.9050 | 0.4 | 2 | 0.6399 | 0.5225 | −1.3637 | 0.4612 |
| 3 | 0.9050 | 0.4 | 3 | 1.1084 | 0.4 | 3 | 0.7389 | 0.6399 | −0.9387 | 1.1496 |
| 4 | 1.0450 | 0.4 | 4 | 1.2798 | 0.4 | 4 | 0.9050 | 0.7389 | −2.5133 | 1.5746 |
| 5 | 1.1683 | 0.4 | 5 | 1.4309 | 0.4 | 5 | 1.0450 | 0.9050 | −1.7300 | 2.5133 |
| 6 | 1.2798 | 0.4 | 6 | 1.5675 | 0.4 | 6 | 1.1084 | 1.0450 | −1.2916 | 0.7833 |
| 7 | 1.3824 | 0.4 | 7 | 1.6931 | 0.4 | 7 | 1.1683 | 1.1084 | −0.8788 | 1.2216 |
| 8 | 1.4778 | 0.4 | 8 | 1.8100 | 0.4 | 8 | 1.2798 | 1.1683 | −2.5133 | 1.6345 |
| 9 | 1.5675 | 0.4 | | | | 9 | 1.3824 | 1.2798 | −1.7061 | 2.5133 |
| 10 | 1.6523 | 0.4 | | | | 10 | 1.4309 | 1.3824 | −1.2776 | 0.8072 |
| 11 | 1.7329 | 0.4 | | | | 11 | 1.4778 | 1.4309 | −0.8636 | 1.2357 |
| 12 | 1.8100 | 0.4 | | | | 12 | 1.5675 | 1.4778 | −2.5133 | 1.6497 |
| | | | | | | 13 | 1.6523 | 1.5675 | −1.6967 | 2.5133 |
| | | | | | | 14 | 1.6931 | 1.6523 | −1.2716 | 0.8165 |
| | | | | | | 15 | 1.7329 | 1.6931 | −0.8565 | 1.2417 |
| | | | | | | 16 | 1.8100 | 1.7329 | −2.5133 | 1.6567 |

Figure 13D:
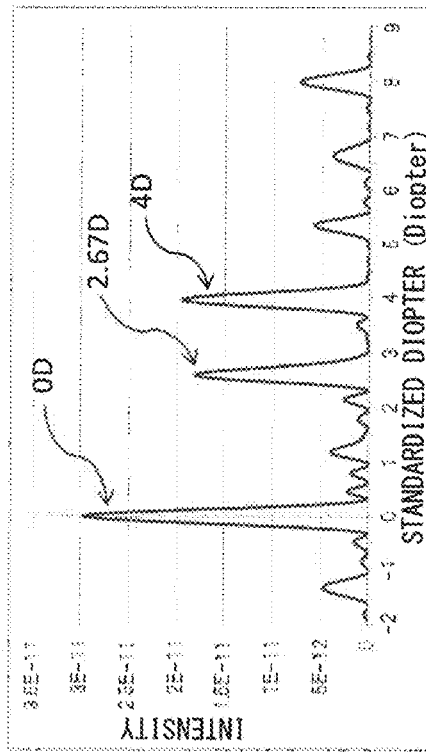

With the composite profile of this example, there is a synchronous structure for which the zone radii of starting profiles (1) and (2) are matched using the zone numbers for which n=3Ω and m=2Ω (Ω is a natural number), and for which three continuous zone pitches of starting profile (1) and two continuous zone pitches of starting profile (2) are the same. As a result, an item for which these profiles are synthesized has four blazes newly formed in the synchronous region. Therefore, a structure is exhibited which has phase profiles of a similar pattern repeated in zone units of the first to fourth, fifth to eighth, ninth to twelfth, thirteenth to sixteenth, and so on for the composite profile. FIG. 13D shows the intensity distribution on the optical axis of the composite profile obtained in this way.

The intensity distribution of this composite profile is an item for which three major peaks are generated at the positions of 0 D, 2.67 D, and 4 D. The peak generated at 0 D is based on the 0th order diffracted light of this composite profile, the 4 D peak is based on the +1 order diffracted light of starting profile (1), and the 2.67 D peak is based on the +1 order diffracted light of starting profile (2).

also have visual ability at the reading position, and it is also possible to do work while viewing a personal computer monitor since it is also possible to see at a position correlating to 2.67 D, specifically, a point of approximately 50 to 60 cm in front.

However, as can be seen from FIG. 13D, with the composite profile of this example, excess peaks are generated due to multi-order light, so there is a risk of halo, glare or the like occurring with a decrease in the gain of the major peaks due to those peaks. In particular, the high order region (5 D to 8 D region) peaks are a cause of expanded halos, and reduction of these peaks is important. In light of that, at least one of phase and amplitude of the composite profile is adjusted to perform reduction of peaks due to multi-order light without changing the composite profile intensity ratio, and the diffractive multi-focal lens equipped with the adjusted profile obtained as a result is shown hereafter as example 6.

(ii) Generation of the Adjusted Profile Using Phase Adjustment

When doing adjustment, the same as the group of examples noted above, first, the phase information of the composite profile is divided into the phase constant and the phase shift, and the phase adjustment is performed based on that. The details of the divided composite profile phase constant and phase shift as well as the adjusted profile are shown in Table 10.

With this example, we can see that by this phase adjustment, the intensity of the high order region multi-order light peaks (arrows in FIG. 14B) is reduced. Regarding the major peaks, though the intensity ratio does not change with the composite profile before adjustment, the amount of reduction of the multi-order light peaks increases the major peak intensity by that amount because it is redistributed to these major peaks, which was found to increase gain.

TABLE 10

| Zone No. i | Zone radius (mm) | | Composite profile (Example 6) | | Adjusted profile(Example 6) | | | |
|---|---|---|---|---|---|---|---|---|
| | Outer radius $r_i$ | Inner radius $r_{i-1}$ | Phase constant h | Phase shift τ | Phase constant h | Phase Shift τ | After adjustment $\phi_i'$ | After adjustment $\phi_{i-1}'$ |
| 1 | 0.5225 | 0 | 0.727 | 0.231 | 0.6 | 0.157 | −1.7279 | 2.0420 |
| 2 | 0.6399 | 0.5225 | 0.290 | −0.451 | 0.2 | 0.628 | 0 | 1.2566 |
| 3 | 0.7389 | 0.6399 | 0.332 | 0.105 | 0.2 | 0.628 | 0 | 1.2566 |
| 4 | 0.9050 | 0.7389 | 0.651 | −0.469 | 0.6 | −0.628 | −2.5133 | 1.2566 |
| 5 | 1.0450 | 0.9050 | 0.675 | 0.392 | 0.6 | 0.157 | −1.7279 | 2.0420 |
| 6 | 1.1084 | 1.0450 | 0.330 | −0.254 | 0.2 | 0.628 | 0 | 1.2566 |
| 7 | 1.1683 | 1.1084 | 0.334 | 0.171 | 0.2 | 0.628 | 0 | 1.2566 |
| 8 | 1.2798 | 1.1683 | 0.660 | −0.439 | 0.6 | −0.628 | −2.5133 | 1.2566 |
| 9 | 1.3824 | 1.2798 | 0.672 | 0.404 | 0.6 | 0.157 | −1.7279 | 2.0420 |
| 10 | 1.4309 | 1.3824 | 0.332 | −0.235 | 0.2 | 0.628 | 0 | 1.2566 |
| 11 | 1.4778 | 1.4309 | 0.334 | 0.186 | 0.2 | 0.628 | 0 | 1.2566 |
| 12 | 1.5675 | 1.4778 | 0.668 | −0.432 | 0.6 | −0.628 | −2.5133 | 1.2566 |
| 13 | 1.6523 | 1.5675 | 0.670 | 0.408 | 0.6 | 0.157 | −1.7279 | 2.0420 |
| 14 | 1.6931 | 1.6523 | 0.332 | −0.228 | 0.2 | 0.628 | 0 | 1.2566 |
| 15 | 1.7329 | 1.6931 | 0.334 | 0.193 | 0.2 | 0.628 | 0 | 1.2566 |
| 16 | 1.8100 | 1.7329 | 0.664 | −0.428 | 0.6 | −0.628 | −2.5133 | 1.2566 |

The composite profile of this example is made by repeating a similar phase structure with four continuous zone pitches, so considering that regularity, first, phase adjustment was performed for the first to fourth zones. For the phase constant, this remains at the fine adjustment level, but the phase shift was changed significantly. Specifically, the second and third phase shifts were shifted greatly to the plus side, and the blaze valley position of those zones were made to be on the reference line. The pattern adjusted in this way was also set for the fifth to eighth, ninth to twelfth, and thirteenth to sixteenth zones which are the other repeated regions.

Figure 14A:
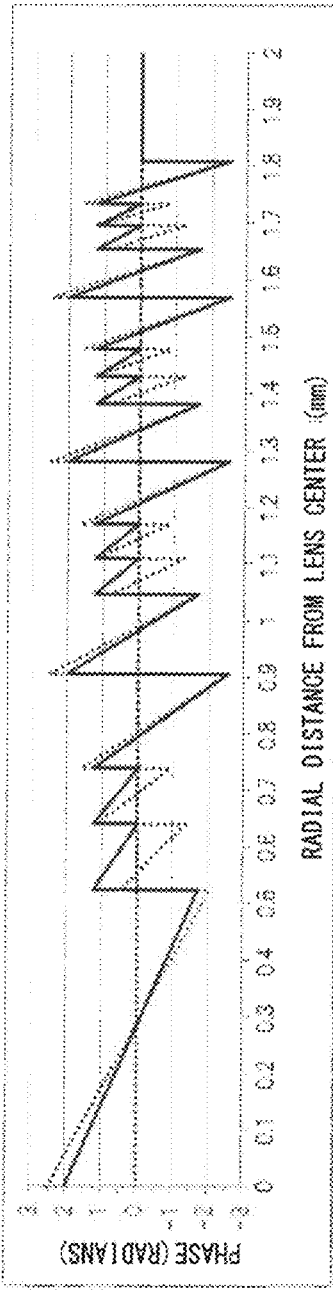
FIG. 14A is a graph of the phase function showing together the adjusted profile as example 6 obtained by adjusting the phase of a specific zone with the composite profile shown in FIG. 13C and the composite profile before adjustment.
Figure 14B:
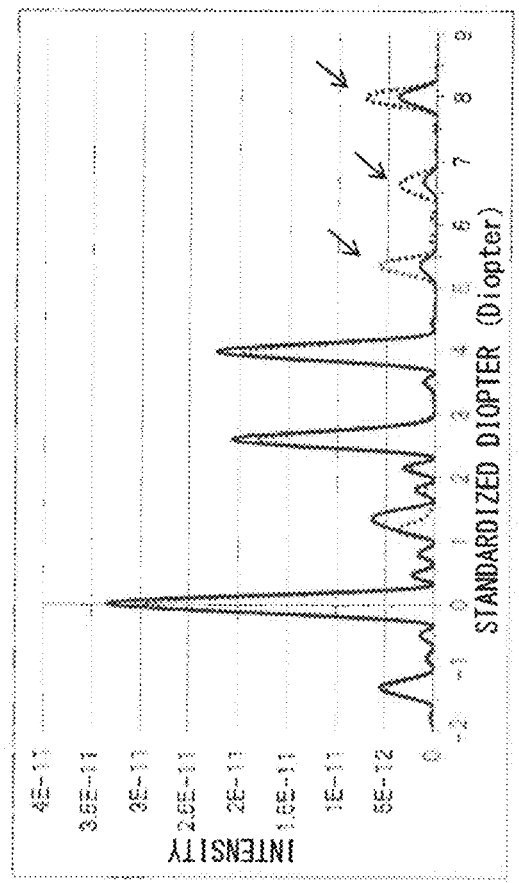
FIG. 14B is a graph showing together the light intensity distribution of the diffractive multi-focal lens having that adjusted profile and the light intensity distribution of the diffractive multi-focal lens having the composite profile before adjustment.

The adjusted profile and intensity distribution on the optical axis obtained in this way are respectively shown in FIG. 14A and FIG. 14B compared with the composite profile.

Example 7

With example 6 noted above, by implementing phase adjustment with the composite profile zones as the subject, peaks due to multi-order light are reduced, and it was shown that it is possible to control light intensity distribution. With this example, we will describe an example of other phase adjustment conditions.

First, the phase constant and phase shift were varied with the same composite profile as was used with example 6 as the subject. The details of the obtained adjusted profile are shown in Table 11.

TABLE 11

| Zone No. i | Zone radius (mm) | | Composite profile (Example 6) | | Adjusted profile(Example 7) | | | |
|---|---|---|---|---|---|---|---|---|
| | Outer radius $r_i$ | Inner radius $r_{i-1}$ | Phase constant h | Phase Shift τ | Phase constant h | Phase Shift τ | After adjustment $\phi_i'$ | After adjustment $\phi_{i-1}'$ |
| 1 | 0.5225 | 0 | 0.727 | 0.231 | 0.6 | 0.157 | −1.7279 | 2.0420 |
| 2 | 0.6399 | 0.5225 | 0.290 | −0.451 | 0 | 0.628 | 0.6283 | 0.6283 |
| 3 | 0.7389 | 0.6399 | 0.332 | 0.105 | 0 | 0.628 | 0.6283 | 0.6283 |
| 4 | 0.9050 | 0.7389 | 0.651 | −0.469 | 0.6 | −0.628 | −2.5133 | 1.2566 |
| 5 | 1.0450 | 0.9050 | 0.675 | 0.392 | 0.6 | 0.157 | −1.7279 | 2.0420 |
| 6 | 1.1084 | 1.0450 | 0.330 | −0.254 | 0 | 0.628 | 0.6283 | 0.6283 |
| 7 | 1.1683 | 1.1084 | 0.334 | 0.171 | 0 | 0.628 | 0.6283 | 0.6283 |
| 8 | 1.2798 | 1.1683 | 0.660 | −0.439 | 0.6 | −0.628 | −2.5133 | 1.2566 |
| 9 | 1.3824 | 1.2798 | 0.672 | 0.404 | 0.6 | 0.157 | −1.7279 | 2.0420 |
| 10 | 1.4309 | 1.3824 | 0.332 | −0.235 | 0 | 0.628 | 0.6283 | 0.6283 |
| 11 | 1.4778 | 1.4309 | 0.334 | 0.186 | 0 | 0.628 | 0.6283 | 0.6283 |
| 12 | 1.5675 | 1.4778 | 0.663 | −0.432 | 0.6 | −0.628 | −2.5133 | 1.2566 |

TABLE 11-continued

| | Zone radius (mm) | | Composite profile (Example 6) | | Adjusted profile(Example 7) | | | |
|---|---|---|---|---|---|---|---|---|
| Zone No. i | Outer radius $r_i$ | Inner radius $r_{i-1}$ | Phase constant h | Phase Shift τ | Phase constant h | Phase Shift τ | After adjustment $\phi_i'$ | After adjustment $\phi_{i-1}'$ |
| 13 | 1.6523 | 1.5675 | 0.670 | 0.408 | 0.6 | 0.157 | −1.7279 | 2.0420 |
| 14 | 1.6931 | 1.6523 | 0.332 | −0.228 | 0 | 0.628 | 0.6283 | 0.6283 |
| 15 | 1.7329 | 1.6931 | 0.334 | 0.193 | 0 | 0.628 | 0.6283 | 0.6283 |
| 16 | 1.8100 | 1.7329 | 0.664 | −0.428 | 0.6 | −0.628 | −2.5133 | 1.2566 |

With this example, with the adjustment conditions of example 6, there is no difference other than that the phase constant of the second and third zones is h=0, and that change is applied to the same repeated regions with the phase constant of the sixth, seventh, tenth, eleventh, fourteenth, and fifteenth zones as h=0. This change was used to set the adjustment conditions of this example. The adjusted profile obtained with this example and the intensity distribution on the optical axis are respectively shown in FIGS. 15A and 15B.

With this example, with both the second and third zones with the phase adjustment conditions, the phase constant h=0, and the phase shift was set to be the same, so these are zones become one integrated single unit zone that is parallel to the reference line which has no blaze tilt. This structure is set in each repeated region. The intensity distribution of this adjusted profile is one for which the multi-order light peaks of the high order regions shown with example 6 are further reduced, and the intensity of the 0th order diffraction peaks is further increased.

Incidentally, in relation to examples 6 and 7 described above, an investigation was done by simulation of the imaging characteristics projected on the plane of retina in a state inserted into the human eye with these examples as actual intraocular lens specifications. Specifically, a simulated operation was made in a state with the adjusted profile of examples 6 and 7 and the composite profile of example 6 as a comparative example being provided as a relief structure on the front surface of the intraocular lens, and that intraocular lens being inserted in the human eye, and an investigation was done of the image formed on the retina when viewing far objects with that eye optical system.

In specific terms, to study the state of halos when viewing far street lamps, car headlights or the like at night, light emitted from a light source with a point light source at a far distance made incident as plane waves on the eyeball, the intensity distribution on the image plane of the 0 D peak focal point position used for far vision was calculated, and the halo was evaluated using this intensity distribution. The intensity distribution on the image plane for that point light source will hereafter be called the point spread function.

Furthermore, to also confirm visual performance when viewing an object with spreading at a far distance, simulation was also done of visual performance when viewing a Landolt ring correlating to visual acuity of 0.2. In regard to the Landolt ring simulation, the Landolt ring image data was converted to actual size when projected on the retina, and a convolution calculation was implemented between that converted image and the point spread function noted above, and the image data obtained from those results was used as the image that is imaged on the retina.

The simulation was performed under the following conditions using VirtualLab (product name) made by Light Trans GmbH.

Eye optical system: System for which the cornea, aqueous humor, iris, intraocular lens, vitreous humor, and retina are arranged in that order, and the refractive index and shape are set based on human eye data
Intraocular lens power: 20 D
Light source: Far point type light source
Light wavelength: 546 nm
Pupil diameter: Diameter 3.6 mm The simulated results of the composite profile of example 6, the adjusted profile of example 6, and the adjusted profile of example 7 are respectively shown in FIGS. 16A, 16B, and 16C, FIGS. 17A, 17B, and 17C, and FIGS. 18A, 18B, and 18C. In the drawings, FIGS. 16A, 17A and 18A do image display of the point spread function obtained from the simulation calculation, and regards this as a halo image. The maximum value of the brightness scale between images is the same and made so it is possible to compare as is. Also, in the drawings, FIGS. 16B, 17B and 18B plot the intensity of the point spread function image plane center in relation to the radial direction. In the drawings, FIGS. 16C, 17C and 18C show the results of convolution calculation of the Landolt ring and the point spread function noted above. Also, to quantitatively compare the brightness of the Landolt ring on the image plane, the intensity distribution of the region shown by the arrow of FIG. 18D is shown in FIG. 18E in regards to each example.

Figure 16A:
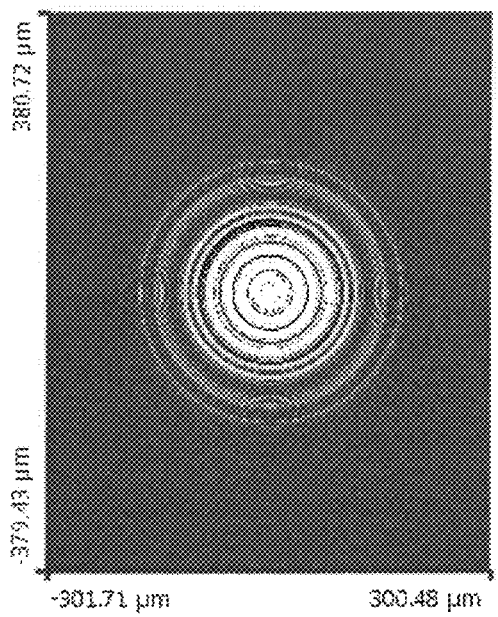
FIGS. 16A-16C show the results of simulation of the imaging characteristics projected on the retina surface in a state with the diffractive multi-focal lens constituted from the composite profile of example 6 set in the eye as an intraocular lens or contact lens, where
Figure 16B:
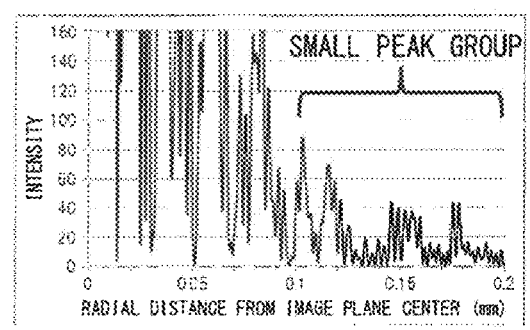
Figure 16C:
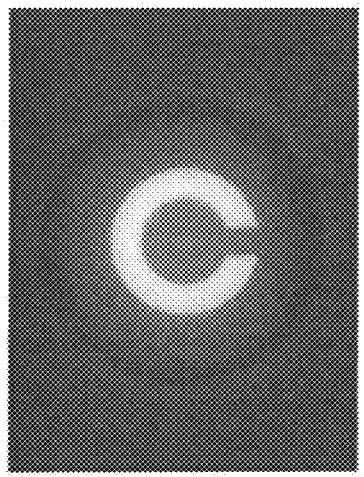

From the results shown in FIGS. 16A and 16B, we can see that with the composite profile before adjustment, the halo spread is large, and in the halo shaped region that spread to the periphery, a group of noise form small peaks are generated. These small peaks such as noise are generated by light that forms peak groups by multi-order light being imaged on the retina, and we can see that the existence of the peak group by multi-order light brings halo spread.

Figure 17A:
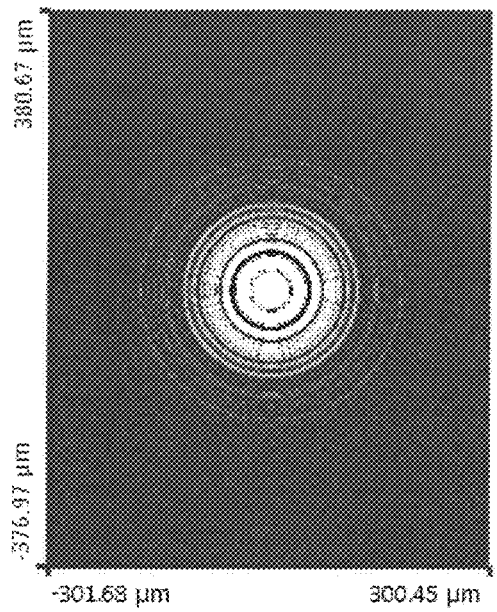
FIGS. 17A-17C show the results of simulation of the imaging characteristics projected on the retina surface in a state with the diffractive multi-focal lens constituted from the adjusted profile of example 6 set in the eye as an intraocular lens or contact lens, where
Figure 17B:
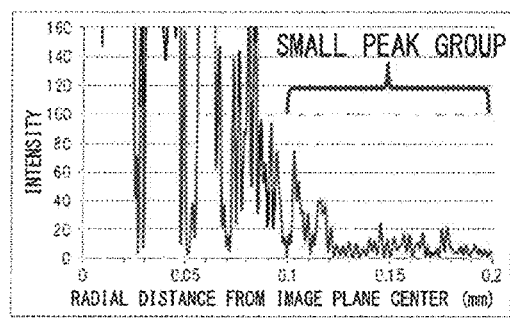
Figure 17C:
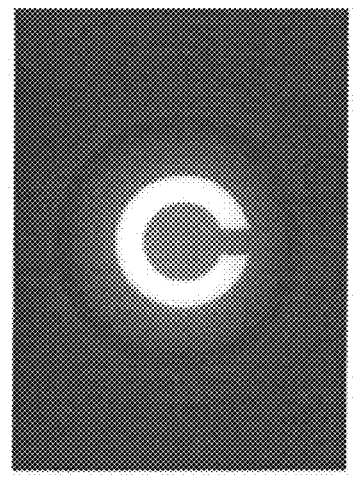

In contrast to this, from the results shown in FIGS. 17A and 17B, with the adjusted profile of example 6, we can see that the halo spread is smaller than with the composite profile. For the point spread function as well, we can see that there is a significant decrease in the noise form peak intensity. This is because with the adjusted profile of example 6, the intensity of the peak group due to multi-order light is decreased, and as a result, the halo spread is reduced.

Also, from the results shown in FIGS. 18A and 18B, we can see that with the adjusted profile of example 7, the noise due to multi-order light is further decreased, and with the halo simulation as well, the halo spread is suppressed more.

Furthermore, from the Landolt ring simulation results shown in each of FIGS. 16C, 17C and 18C, we can see that the composite profile of example 6 has the lowest brightness, the brightness becomes higher in the sequence of the adjusted profile of example 6 and then example 7, and the contrast becomes higher in sequence. This contrast is also clear from the intensity distribution drawing of FIG. 18E. This is due to the fact that as described above, with the adjusted profile of example 6 and 7, the multi-order light peaks decrease, and the gain of the intensity of the major peaks improves.

Therefore, as can be understood from the simulation results when using as the intraocular lens, we can see that the tuning by phase and amplitude adjustment of the present invention is successful in reducing halo and improving contrast.

Example 8

With examples 1 to 7 described above, regarding phase and amplitude adjustment, the subject was a composite profile synthesized from two starting profiles. With example 8, we will describe an example of adjusting the composite profile when there are three starting profiles.

(i) Preparation of the Composite Profile

The third starting profile in addition to starting profiles (1) and (2) will be called starting profile (3). The phase function of the respective starting profiles used when acquiring the composite profile are blaze shaped functions, where based on Equation 13, Equation 14, and Equation 22 which are standard setting equations, the respective zone pitches are determined such that with the starting profile (1), the addition power $P_1$ is $P_1=4$ D, with the starting profile (2), the addition power $P_2$ is ⅔ of $P_1$ with $P_2=2.666$ D, and with starting profile (3), the addition power $P_3$ is ⅓ of $P_1$, with $P_3=1.333$ D. The phase constant of starting profiles (1), (2) and (3) are respectively 0.425, 0.325, and 0.25. The starting profiles are overlapped on the same region, and the composite profile was obtained by adding the phase. Details of the starting profiles and composite profile are shown in Table 12 and FIGS. 19A, 19B, 19C, and 19D.

zone diameters match for pitches of the zone count being (b×e)/z=9/3=3 for starting profile (1), (a×e)/z=6/3=2 for starting profile (2), and (b×d)/z=3/3=1 for starting profile (3). We can see this relationship from FIGS. 19A, 19B, 19C, and 19D. With the composite profile, a structure is formed which has phase distribution of the same form repeated in zone regions with four zones of the first to fourth, fifth to eighth, ninth to twelfth, and thirteenth to sixteenth as units.

Figure 19A:
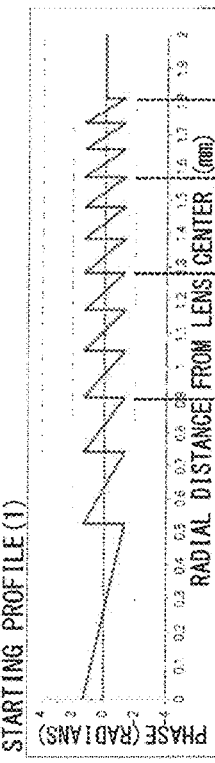
FIGS. 19A-19E are drawings relating to the composite profile with example 8 of the present invention, where
Figure 19B:
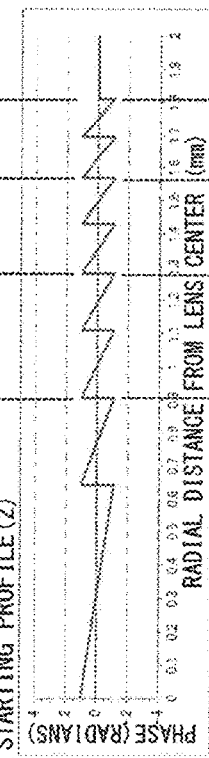
Figure 19C:
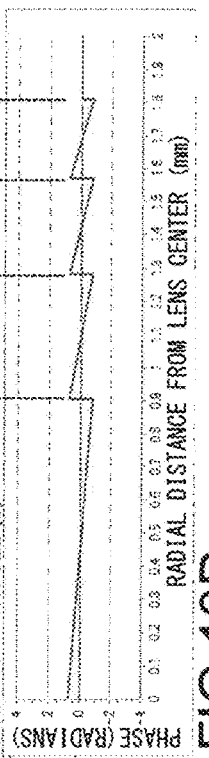
Figure 19D:
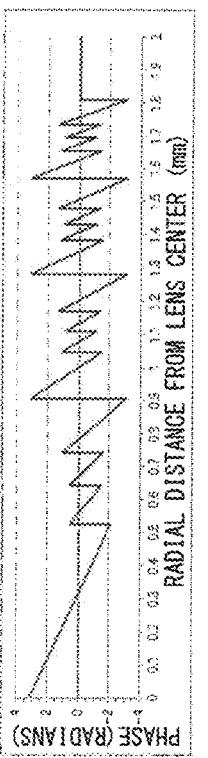
Figure 19E:
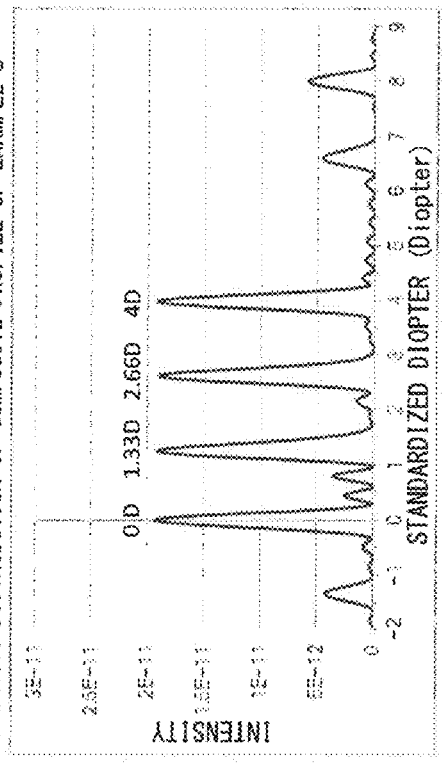

FIG. 19E shows the intensity distribution on the optical axis of this composite profile. With this composite profile, four peaks of about the same intensity are generated at positions of 0 D, 1.33 D, 2.66 D, and 4 D. When a lens that uses a diffractive structure for this composite profile is used as an ophthalmic lens, for example, this is suitable as specifications for a four focal point multi-focal ophthalmic lens with 0 D for far vision, 4 D for near vision, 2.66 D for intermediate vision for viewing a personal computer monitor or the like, and 1.33 D for a second intermediate vision for seeing a range of about 1 m to 2 m in front. This second intermediate vision focal point is a focal point that is useful for clearly seeing dust or trash when sweeping a floor or the like. Also, since the peak intensities are respectively the same, the visual performance is balanced for the respective regions.

However, with the composite profile of this example, as can be seen from FIG. 19E, several peaks due to multi-order light are generated with the light intensity distribution. These peaks hinder improvement in gain of the major peaks, and are also the cause of halo and glare. In light of that, at least one of phase and amplitude of the composite profile is adjusted to perform reduction of peaks due to multi-order light, and as a result, the diffractive multi-focal lens equipped with the adjusted profile shown hereafter was obtained as example 8.

TABLE 12

| | Starting profile (1) Addition power $P_1 = 4$ D | | | Starting profile (2) Addition power $P_2 = 2.666$ D | | | Starting profile (3) Addition power $P_3 = 1.333$ D | | | Composite profile (Example 8) | | | |
|---|---|---|---|---|---|---|---|---|---|---|---|---|---|
| | | | | | | | | | | | Zone radius (mm) | | | |
| Zone No. | Zone radius (mm) | Phase constant | Zone No. | Zone radius (mm) | Phase constant | Zone No. | Zone radius (mm) | Phase constant | Zone No. | Outer radius | Inner radius | Phase (radians) | |
| n | $r_n$ | h | m | $r_n$ | h | q | $r_n$ | h | i | $r_i$ | $r_{i-1}$ | $\varphi_i'$ | $\varphi_{i-1}'$ |
| 1 | 0.5225 | 0.425 | 1 | 0.6399 | 0.325 | 1 | 0.9050 | 0.25 | 1 | 0.5225 | 0 | −2.1030 | 3.1416 |
| 2 | 0.7389 | 0.425 | 2 | 0.9050 | 0.325 | 2 | 1.2798 | 0.25 | 2 | 0.6399 | 0.5225 | −1.4600 | 0.5674 |
| 3 | 0.9050 | 0.425 | 3 | 1.1084 | 0.325 | 3 | 1.5675 | 0.25 | 3 | 0.7389 | 0.6399 | −1.5740 | 0.5820 |
| 4 | 1.0450 | 0.425 | 4 | 1.2798 | 0.325 | 4 | 1.8100 | 0.25 | 4 | 0.9050 | 0.7389 | −3.1416 | 1.0964 |
| 5 | 1.1683 | 0.425 | 5 | 1.4309 | 0.325 | | | | 5 | 1.0450 | 0.9050 | −1.5210 | 3.1416 |
| 6 | 1.2798 | 0.425 | 6 | 1.5675 | 0.325 | | | | 6 | 1.1084 | 1.0450 | −1.1251 | 1.1493 |
| 7 | 1.3824 | 0.425 | 7 | 1.6931 | 0.825 | | | | 7 | 1.1683 | 1.1084 | −1.3463 | 0.9170 |
| 8 | 1.4778 | 0.425 | 8 | 1.8100 | 0.325 | | | | 8 | 1.2798 | 1.1683 | −3.1416 | 1.3241 |
| 9 | 1.5675 | 0.425 | | | | | | | 9 | 1.3824 | 1.2798 | −1.4749 | 3.1416 |
| 10 | 1.6523 | 0.425 | | | | | | | 10 | 1.4809 | 1.3324 | −1.0829 | 1.1954 |
| 11 | 1.7329 | 0.425 | | | | | | | 11 | 1.4778 | 1.4309 | −1.3117 | 0.9592 |
| 12 | 1.8100 | 0.425 | | | | | | | 12 | 1.5675 | 1.4778 | −3.1416 | 1.3587 |
| | | | | | | | | | 13 | 1.6523 | 1.5675 | −1.4566 | 3.1416 |
| | | | | | | | | | 14 | 1.6931 | 1.6523 | −1.0651 | 1.2137 |
| | | | | | | | | | 15 | 1.7329 | 1.6931 | −1.2964 | 0.9770 |
| | | | | | | | | | 16 | 1.8100 | 1.7329 | −3.1416 | 1.3740 |

With the composite profile comprising three starting profiles of this example, from the relational expressions of Equation 12 and Equation 23 noted above, a=2, b=3, d=1, and e=3 are allocated, and a characteristic feature is that a synchronous structure is formed for which the zone diameter matches with a number of zone pitches correlating to the quotient with each respective number divided using the greatest common divisor of z=3 of the three integral values for which (b×e)=9, (a×e)=6, and (b×d)=3. Specifically, the (ii) Generation of the Adjusted Profile by Phase Adjustment When doing adjustment, the same as with the examples noted above, first, the phase information of the composite profile is divided into the phase constant and the phase shift, and the phase adjustment is performed based on that. The details of the divided composite profile phase constant and phase shift as well as the adjusted profile are shown in Table 13.

TABLE 13

| Zone No. i | Zone radius (mm) Outer radius $r_i$ | Zone radius (mm) Inner radius $r_{i-1}$ | Composite profile (Example 8) Phase constant h | Composite profile (Example 8) Phase Shift τ | Adjusted profile(Example 8) Phase constant h | Adjusted profile(Example 8) Phase Shift τ | Adjusted profile(Example 8) After adjustment $\phi_i'$ | Adjusted profile(Example 8) After adjustment $\phi_{i-1}'$ |
|---|---|---|---|---|---|---|---|---|
| 1 | 0.5225 | 0 | 0.835 | 0.519 | 0.7 | −0.785 | −2.9845 | 1.4137 |
| 2 | 0.6399 | 0.5225 | 0.323 | −0.446 | 0.2 | 1.037 | 0.4084 | 1.6650 |
| 3 | 0.7389 | 0.6399 | 0.343 | −0.496 | 0.2 | −0.220 | −0.8482 | 0.4084 |
| 4 | 0.9050 | 0.7389 | 0.674 | −1.023 | 0.3 | −1.068 | −2.0106 | −0.1257 |
| 5 | 1.0450 | 0.9050 | 0.742 | 0.810 | 0.7 | −0.785 | −2.9845 | 1.4137 |
| 6 | 1.1084 | 1.0450 | 0.362 | 0.012 | 0.2 | 1.100 | 0.4712 | 1.7279 |
| 7 | 1.1683 | 1.1084 | 0.360 | −0.215 | 0.2 | −0.157 | −0.7854 | 0.4712 |
| 8 | 1.2798 | 1.1683 | 0.711 | −0.909 | 0.4 | −1.068 | −2.3248 | 0.1885 |
| 9 | 1.3824 | 1.2798 | 0.735 | 0.833 | 0.7 | −0.785 | −2.9845 | 1.4137 |
| 10 | 1.4309 | 1.3824 | 0.363 | 0.056 | 0.2 | 1.100 | 0.4712 | 1.7279 |
| 11 | 1.4778 | 1.4309 | 0.361 | −0.176 | 0.2 | −0.157 | −0.7854 | 0.4712 |
| 12 | 1.5675 | 1.4778 | 0.716 | −0.891 | 0.4 | −1.068 | −2.3248 | 0.1885 |
| 13 | 1.6523 | 1.5675 | 0.732 | 0.842 | 0.7 | −0.785 | −2.9845 | 1.4137 |
| 14 | 1.6931 | 1.6523 | 0.363 | 0.074 | 0.2 | 1.100 | 0.4712 | 1.7279 |
| 15 | 1.7829 | 1.6931 | 0.362 | −0.160 | 0.2 | −0.157 | −0.7854 | 0.4712 |
| 16 | 1.8100 | 1.7329 | 0.719 | −0.884 | 0.4 | −1.068 | −2.3248 | 0.1885 |

When obtaining the adjusted profile with this example, the main adjustment points implemented on each zone of the composite profile are as follows. Regarding the phase constant, the big change points by adjustment were that the phase constant of the fourth, eighth, twelfth, and sixteenth zones of the composite profile which were in a range from 0.67 to 0.72 were set to small values of 0.3 or 0.4, and regarding phase shift, the first, fifth, ninth, and thirteenth zones before adjustment which were arranged at the plus side were shifted to the minus side, and the second, sixth, tenth, and fourteenth zones were shifted to the plus side.

Figure 20A:
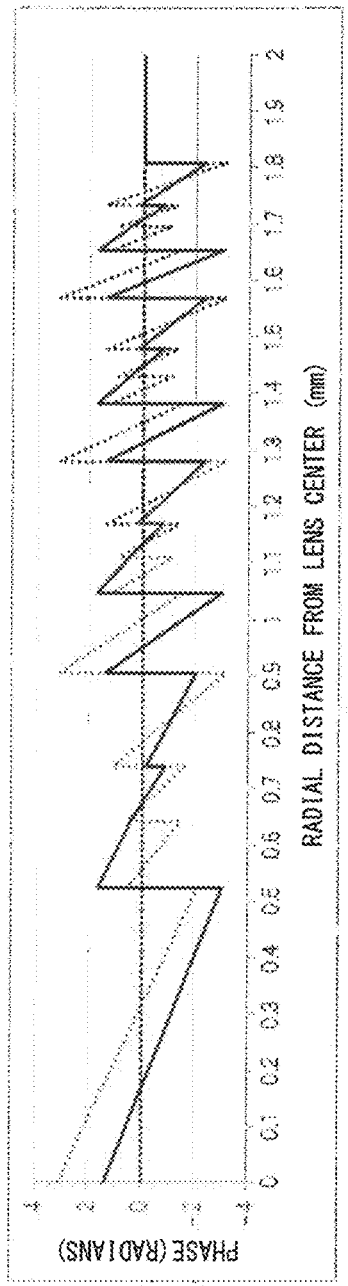
FIG. 20A is a graph of the phase function showing together the adjusted profile as example 8 obtained by adjusting the phase of a specific zone with the composite profile shown in FIG. 19D and the composite profile before adjustment.

FIG. 20A shows the adjusted profile obtained by this adjustment. The feature points with the adjusted profile are that the peak and valley positions of the blaze of the second and third, sixth and seventh, tenth and eleventh, and fourteenth and fifteenth zones almost match, and since the tilt of the zones are almost the same as each other, that these mutual zones are regarded as essentially having a continuous-roof single blaze shape form.

Figure 20B:
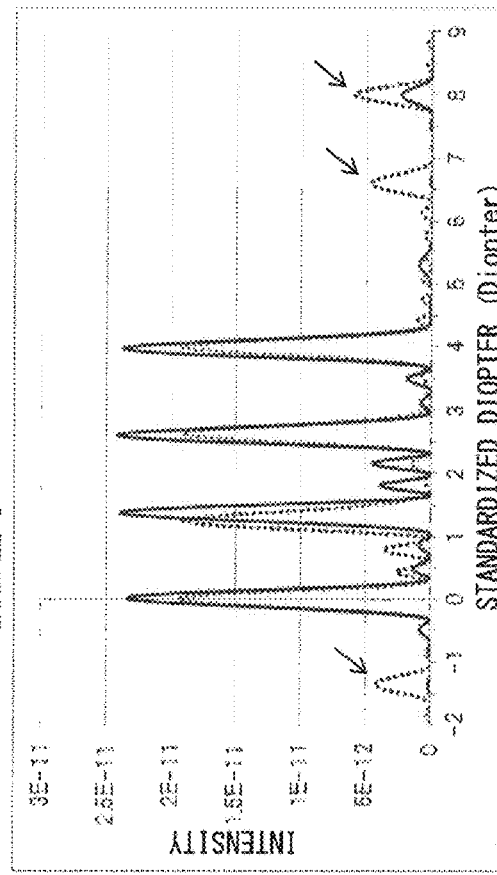
FIG. 20B is a graph showing together the light intensity distribution of the diffractive multi-focal lens having that adjusted profile and the light intensity distribution of the diffractive multi-focal lens having the composite profile before adjustment.

FIG. 20B shows the intensity distribution in the optical axis direction of the adjusted profile. This intensity distribution has a significant reduction in peaks due to multi-order light acknowledged with this composite profile. Also, the intensity ratio before adjustment is maintained with the four major peaks, and we can see that at the amount by which the multi-order light peaks decrease, there is a significant increase in the gain leading to an increase in the intensity of these major peaks.

By preparing the composite profile from three starting profiles in this way, and using the method for adjusting at least one of phase and amplitude, four focal points can be formed freely, and unnecessary peaks due to multi-order light can be reduced, making it possible to provide a multi-focal lens with excellent sharpness when viewing objects in each focal point region, and for which halo, glare and the like are reduced.

Example 9

Figure 21A:
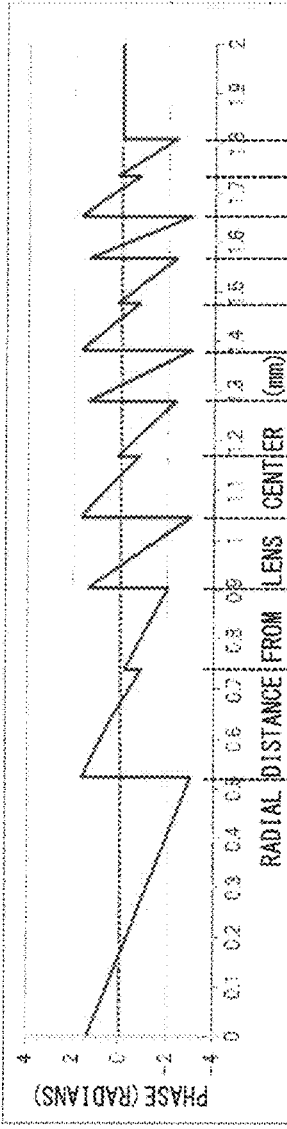
FIGS. 21A-21C are explanatory drawings showing matching with the standard Fresnel pitch for the zone pitch with the adjusted profile of the diffractive multi-focal lens of example 8, where
Figure 21B:
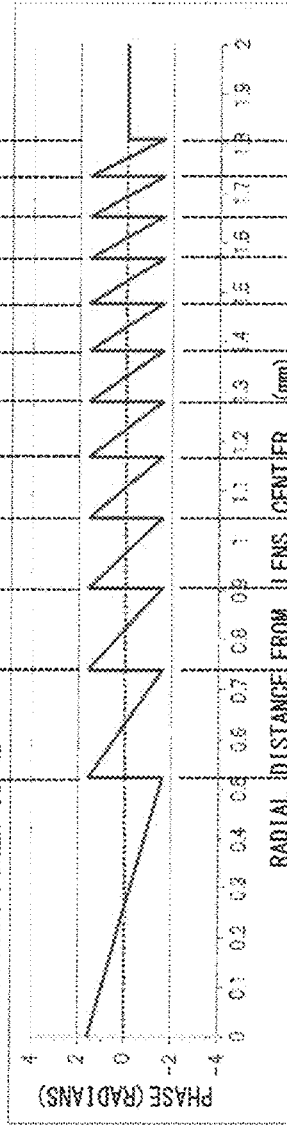
Figure 21C:
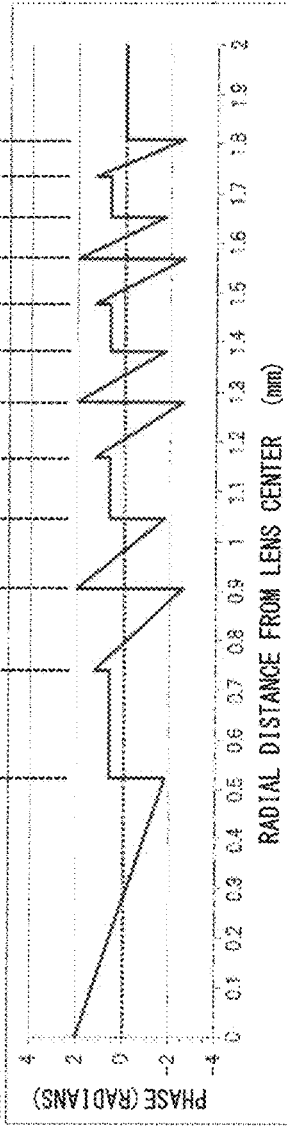

With example 8 noted above, we described that as a result of phase adjustment, the adjacent zones of the second and third, sixth and seventh, tenth and eleventh, and fourteenth and fifteenth are regarded essentially as one continuous-roof blaze shape. When this essentially one continuous-roof blaze is regarded as one zone, the adjusted profile of example 8 has the same zone pitches as the standard Fresnel pitch for which the addition power is 4 D. The relationship of this zone pitch is shown in FIGS. 21A and 21B. When regarding the adjacent zones of the adjusted profile of example 8 as one zone, we can see that this matches with the zone pitch of the standard Fresnel zone. Specifically, in the mode where the plurality of starting profiles are overlapped, the radius of each zone is a non-Fresnel pitch as shown in FIG. 19, for example. Meanwhile, in the adjusted profile, as shown in FIGS. 20 to 21, the radius of each zone can be understood to be substantially a Fresnel pitch by the plurality of zones being integrally consolidated.

On the other hand, there is the same relationship with the adjusted profile of example 7 as well, and with that adjusted profile, the adjacent zones of the second and third, sixth and seventh, tenth and eleventh, and fourteenth and fifteenth have the phase constant as h=0, and because the phase shift is the same value, this is one zone that is essentially completely integrated. The drawing of that adjusted profile of example 7 is shown together as FIG. 21C. Similarly, we can see that the standard Fresnel zone has the same zone pitch. The adjusted profile of example 7 was designed as an item that mainly generates three focal points.

When the phase function is in blaze form, although differing according to the blaze step, it is generally understood that the number of focal points given by the standard Fresnel zone is only two comprising a combination of an n order and (n+1) order diffracted light such as 0th order and first order diffracted light, or first order and second order diffracted light or the like corresponding to the set addition power. However, here, even with the standard Fresnel zone, depending on the phase and amplitude adjustment, it is possible to have diffraction specifications that give at least three focal points. If we can apply the theory that even with the standard Fresnel zone diffractive lens, this is an item that could be obtained as a result of adjusting phase and amplitude of designated zones with the composite profile of a plurality of starting profiles based on the present invention, we can understand this as a diffractive multi-focal lens that gives three or more focal points based on the plurality of starting profiles. Said another way, even with the standard Fresnel zone diffractive lens, it is possible to understand the profile obtained by adjusting the phase and amplitude of that zone as being divided into a plurality of starting profiles, and we can understand this as a diffractive multi-focal lens of a structure equipped with three or more focal points according to the present invention.

With this example, we performed design of a diffractive lens that can be a four focal point lens suitable as an intraocular lens by using a method for adjusting at least one of phase and amplitude of the standard Fresnel zone based on this kind of new information, specifically, a diffractive multi-focal lens that can be understood as being obtained as a result of implementing adjustment of phase or amplitude on a specified zone of the composite profile obtained by overlapping the zones of the plurality of starting profiles.

In specific terms, first, the zone profiles were set using the standard setting equation such that the addition power is 4 D. In regards to the zone profile, a blaze shaped phase function is set for each zone, and an adjusted profile was obtained for which the blaze phase constant and phase shift were adjusted. The details of the adjusted profile of this example are shown in Table 14.

TABLE 14

| Zone No. i | Zone radius (mm) | | Phase constant h | Phase Shift τ | Adjusted profile(Example 9) | |
|---|---|---|---|---|---|---|
| | Outer radius $r_i$ | Inner radius $r_{i-1}$ | | | After adjustment $\phi_i'$ | After adjustment $\phi_{i-1}'$ |
| 1 | 0.5225 | 0 | 0.6 | −0.314 | −2.1991 | 1.5708 |
| 2 | 0.7389 | 0.5225 | 0.4 | 0.628 | −0.6283 | 1.8850 |
| 3 | 0.9050 | 0.7389 | 0.3 | −0.565 | −1.5080 | 0.3770 |
| 4 | 1.0450 | 0.9050 | 0.6 | −0.314 | −2.1991 | 1.5708 |
| 5 | 1.1683 | 1.0450 | 0.4 | 0.628 | −0.6283 | 1.8850 |
| 6 | 1.2798 | 1.1683 | 0.3 | −0.565 | −1.5080 | 0.3770 |
| 7 | 1.3824 | 1.2798 | 0.6 | −0.314 | −2.1991 | 1.5708 |
| 8 | 1.4778 | 1.3824 | 0.4 | 0.628 | −0.6283 | 1.8850 |
| 9 | 1.5675 | 1.4778 | 0.3 | −0.565 | −1.5080 | 0.3770 |
| 10 | 1.6523 | 1.5675 | 0.6 | −0.314 | −2.1991 | 1.5708 |
| 11 | 1.7329 | 1.6523 | 0.4 | 0.628 | −0.6283 | 1.8850 |
| 12 | 1.8100 | 1.7329 | 0.3 | −0.565 | −1.5080 | 0.3770 |

The drawing of the adjusted profile of this example is shown in FIG. 22A. The adjusted profile of this example is a profile directly set from the standard Fresnel zone having referenced the phase information of the adjusted profile of example 8 noted above. FIG. 22B shows the intensity distribution on the optical axis of the adjusted profile. The intensity distribution of this adjusted profile has the greatest intensity at the 0 D peak, and this is distributed continuously next with 4 D, followed by 2.66 D and 1.33 D peaks. Also, a pattern is shown with which almost no peak groups due to multi-order light are found. In this way, this is a profile comprising standard Fresnel zones, but because it is a profile derived via tuning using the adjustment of the present invention, it also realizes the effect of suppressing peaks due to multi-order light while generating four focal points.

We performed a simulation evaluation using the human eye optical system for a case of using the lens of this example which uses a diffractive structure for the profile as an intraocular lens. The simulation was performed using the same Light Trans GmbH. VirtualLab (product name) as was used with examples 6 and 7 noted above, and using the same conditions. Also, at each focal point position, a calculation of the point spread function of each focal point position was calculated to find and understand how a Landolt ring correlating to visual acuity of 1.2 is seen, and convolution calculation was performed between the point spread function and the image data of the Landolt ring of the size correlating to visual acuity of 1.2 on the retina, and this was used as the imaging data projected on the retina.

The results of the simulation are respectively shown in FIGS. 22C, 22D, 22E, and 22F. Each position of 0 D, 1.33 D, 2.66 D, and 4 D for the intensity distribution of FIG. 22B can be estimated as being at distances of infinity (actually distance of 4 to 5 m or greater), 90 cm, 50 cm, and 35 cm with the eye as the base point. At each position, though there are differences in contrast or in lightness and darkness of the background, the gap of Landolt ring is sufficiently perceivable, and we can see that this can be a lens for which sufficient vision is possible of objects at each respective position. Therefore, this lens is useful for far vision, but also for near distance reading and work, for work while viewing a personal computer, and also for work such as sweeping a floor or the like.

In this way, even with a standard Fresnel zone, it is possible to establish this as a diffractive multi-focal lens with a structure according to the present invention, specifically, even with a standard Fresnel zone, it is possible to generate at least three focal points whether with phase or amplitude adjustment based on the technical concept of the present invention, and possible to have imaging characteristics for which multi-order light is controlled.

Example 10

However, when we look at the phase form of the adjusted profile of example 9 noted above, the tilt of adjacent zones second and third, fifth and sixth, eighth and ninth, and eleventh and twelfth is almost the same, and the peak and valley positions are close. Therefore, it is possible to regard these mutually adjacent zones as essentially being one zone. Also, it is conceivable for multiple focal points to be generated in the new zone pitches for which the zones are integrated into essentially one zone. In light of that, design was performed for a diffractive lens for which it is possible to be a multi-focal lens with phase being readjusted with the new zone pitches for which these zones were integrated.

The details of the profile of the diffractive multi-focal lens as example 10 obtained as a result are shown in Table 15.

TABLE 15

| Zone No. i | Zone radius (mm) | | Phase constant h | Phase Shift τ | Adjusted profile(Example 10) | |
|---|---|---|---|---|---|---|
| | Outer radius $r_i$ | Inner radius $r_{i-1}$ | | | After adjustment $\phi_i'$ | After adjustment $\phi_{i-1}'$ |
| 1 | 0.5225 | 0 | 0.7 | −0.251 | −2.4504 | 1.9478 |
| 2 | 0.9050 | 0.5225 | 0.4 | 0.314 | −0.9425 | 1.5708 |
| 3 | 1.0450 | 0.9050 | 0.7 | −0.157 | −2.3562 | 2.0420 |
| 4 | 1.2798 | 1.0450 | 0.4 | 0.000 | −1.2566 | 1.2566 |
| 5 | 1.3824 | 1.2798 | 0.7 | −0.157 | −2.3562 | 2.0420 |
| 6 | 1.5675 | 1.3824 | 0.4 | 0.000 | −1.2566 | 1.2566 |
| 7 | 1.6523 | 1.5675 | 0.7 | −0.157 | −2.3562 | 2.0420 |
| 8 | 1.8100 | 1.6523 | 0.4 | 0.000 | −1.2566 | 1.2566 |

Figure 23A:
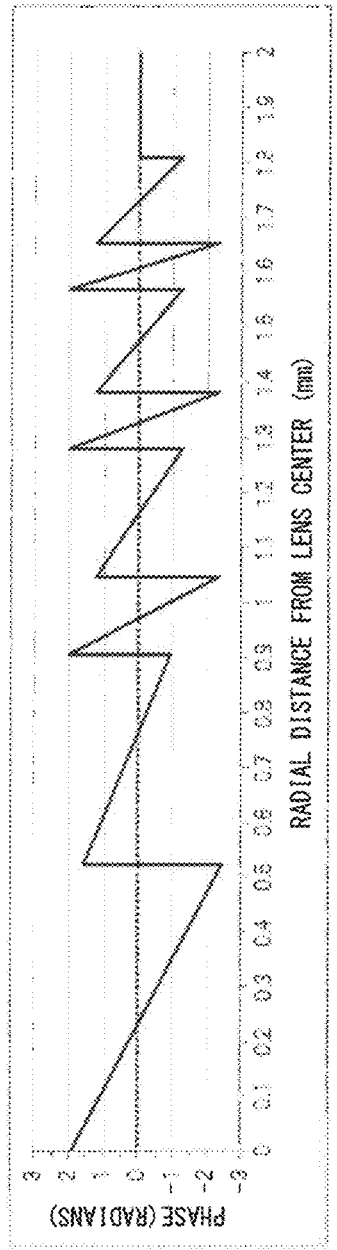
FIGS. 23A and 23B are drawings relating to the diffractive multi-focal lens of example 10 for which it is possible to realize four focal points with even more simplified zone pitches by performing phase adjustment on specific zones in relation to the diffractive multi-focal lens of example 9 having the standard Fresnel pitch, where
Figure 23B:
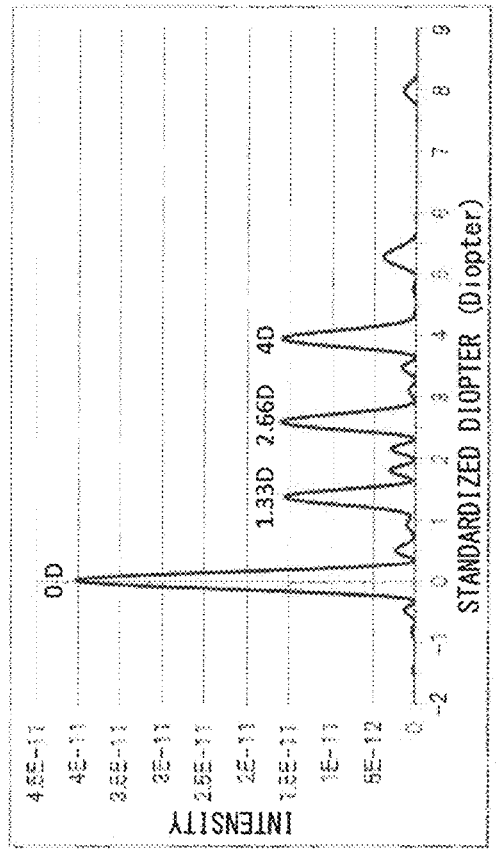

This profile is such that the (3n−1)th zone and the 3n-th zone (n is a natural number) of the standard Fresnel zone are integrated into one zone, so this is a zone pitch that cannot be determined with the standard Fresnel zone setting equation. Also, with the same aperture diameter, the constituent zone count is even smaller than with the standard Fresnel zone. A drawing of the adjusted profile of this example is shown in FIG. 23A. Also, the intensity distribution in the optical axis direction of this profile is shown in FIG. 23B.

From these drawings, with the diffractive multi-focal lens of this example, we can see that more than with the standard Fresnel zone, there is a simpler zone structure, and the multi-focal point generating function is maintained.

From the results shown with examples 9 and 10 described above, based on the technical concepts of the present invention, for the adjusted profile for which adjustment was implemented for each zone with the composite profile generated by overlapping a plurality of starting profiles as a base, we can understand that it is possible to realize a simplified zone structure for this adjusted profile. This means that, said another way, if the adjusted profile is the subject, by going through adjustment of the phase or amplitude for each zone, it is possible to restore the adjusted profile to the structure of the standard Fresnel zone or an even more simplified profile (specifically, simplification of the zone structure), and even with the simplified profile, it is possible to generate at least three focal points freely at any position, and to obtain a diffractive lens for which the generation of multi-order light is suppressed. Also, the profile with this simplified structure is included in the technical concept of the present invention, and in addition to being able to achieve the technical effects based on the present invention, aside from the effects relating particularly to imaging characteristics, because the structure is simple, this also links to things such as ease of manufacturing when actually creating a diffractive structure with the profile in a relief shape, making it possible to obtain further effects.

Example 11

Next, though the fact that it is possible to obtain an adjusted profile through the profile synthesized from starting profiles (1) and (2) in relation to the asynchronous structure for which none of the zone diameter match is as described previously, we will show a specific example hereafter to make this even easier to understand.

(i) Preparation of the Composite Profile

Both starting profiles (1) and (2) have the phase function as a blaze shaped function, where the same as with example 6, the addition power of starting profiles (1) and (2) are set as $P_1=4$ diopters and $P_2=2.666$ D. The first zone radius of starting profile (1) is set freely at $r_1=0.47$ mm, and the first zone radius of starting profile (2) is set at $r_1'=0.3872$ mm, so the zone pitch of each starting profile was determined based on the general setting equations Equation 8 and Equation 10. The phase constant of starting profiles (1) and (2) are respectively 0.4 and 0.35. With this example, the phase $\phi_0$ of the first zone was determined based on Equation 25 noted below. The composite profile was obtained by overlapping the starting profiles (1) and (2) on the same region and adding the phase.

$$\phi_0 = h \times \pi \times \left(\frac{P \times r_1^2}{\lambda} - 1\right) \quad \text{[Equation 25]}$$

$\phi_0$: Phase of inner diameter position of the first zone
h: Phase constant
P: Addition power
$r_1$: First zone radius
$\lambda$: Design wavelength The details of the starting profiles (1) and (2) and the composite profile are shown in Table 16 and FIGS. 24A and 24B.

TABLE 16

| Starting profile(1) Addition power $P_1 = 4$ D | | Starting profile(2) Addition power $P_2 = 2.666$ D | | Composite profile(Example 11) Zone radius (mm) | | | | |
|---|---|---|---|---|---|---|---|---|
| Zone | Zone radius (mm) | Phase constant | Zone | Zone radius (mm) | Phase constant | Zone | Outer radius | Inner radius | Phase (radians) |
| No. n | $r_n$ | h | No. m | $r_m$ | h | No. i | $r_i$ | $r_{i-1}$ | $\phi_i'$ | $\phi_{i-1}'$ |
| 1 | 0.47 | 0.4 | 1 | 0.3872 | 0.35 | 1 | 0.3872 | 0 | −1.9980 | 0.4827 |
| 2 | 0.7027 | 0.4 | 2 | 0.7479 | 0.35 | 2 | 0.47 | 0.3872 | −0.6616 | 0.2010 |
| 3 | 0.8757 | 0.4 | 3 | 0.9843 | 0.35 | 3 | 0.7027 | 0.47 | −2.0807 | 1.8516 |
| 4 | 1.0197 | 0.4 | 4 | 1.1740 | 0.35 | 4 | 0.7479 | 0.7027 | −0.4995 | 0.4325 |
| 5 | 1.1458 | 0.4 | 5 | 1.3371 | 0.35 | 5 | 0.8757 | 0.7479 | −1.3456 | 1.6995 |
| 6 | 1.2593 | 0.4 | 6 | 1.4823 | 0.35 | 6 | 0.9843 | 0.8757 | −1.7384 | 1.1676 |
| 7 | 1.3634 | 0.4 | 7 | 1.6146 | 0.35 | 7 | 1.0197 | 0.9843 | −0.5674 | 0.4606 |
| 8 | 1.4601 | 0.4 | 8 | 1.7367 | 0.35 | 8 | 1.1458 | 1.0197 | −2.0286 | 1.9458 |
| 9 | 1.5507 | 0.4 | | | | 9 | 1.1740 | 1.1458 | −0.4685 | 0.4845 |
| 10 | 1.6364 | 0.4 | | | | 10 | 1.2593 | 1.1740 | −1.3067 | 1.7305 |
| 11 | 1.7178 | 0.4 | | | | 11 | 1.3371 | 1.2593 | −1.7218 | 1.2065 |
| | | | | | | 12 | 1.3634 | 1.3371 | −0.5548 | 0.4772 |
| | | | | | | 13 | 1.4601 | 1.3634 | −2.0188 | 1.9583 |
| | | | | | | 14 | 1.4823 | 1.4601 | −0.4604 | 0.4943 |
| | | | | | | 15 | 1.5507 | 1.4823 | −1.2945 | 1.7387 |
| | | | | | | 16 | 1.6146 | 1.5507 | −1.7158 | 1.2186 |
| | | | | | | 17 | 1.6364 | 1.6146 | −0.5498 | 0.4832 |
| | | | | | | 18 | 1.7178 | 1.6364 | −2.0146 | 1.9634 |

Figure 24A:
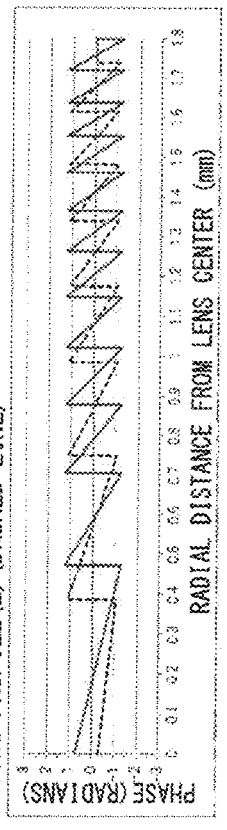
FIGS. 24A-24C are drawings relating to the composite profile of example 11 of the present invention, where
Figure 24B:
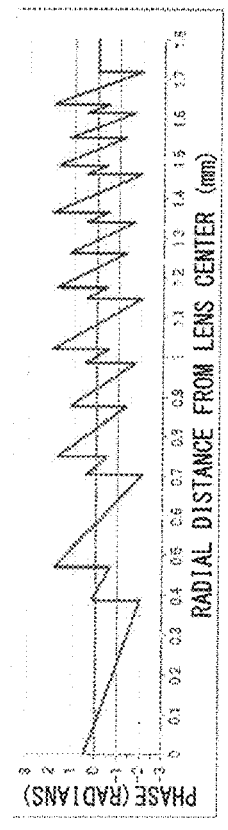
Figure 24C:
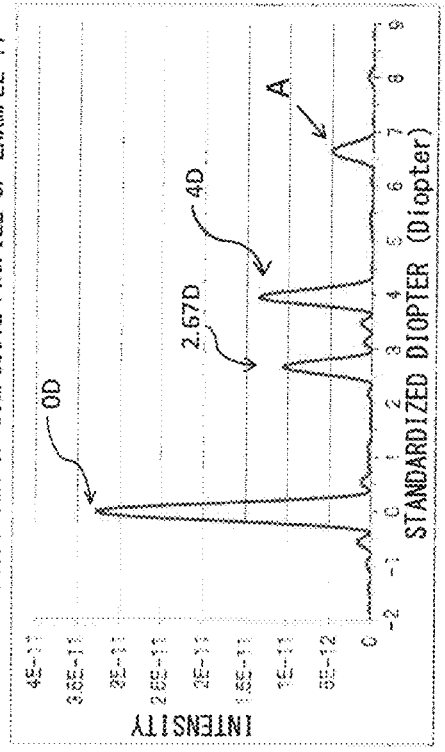

From FIG. 24A, we can see that the zone radii of starting profiles (1) and (2) are in an asynchronous relationship for which they do not match in any region. As shown in FIG. 24B, the composite profile obtained by synthesizing the starting profiles exhibits a structure for which similar phase units are repeated in zone units of the first to fifth, sixth to tenth, eleventh to fifteenth, and so on (or the second to sixth, seventh to eleventh, twelfth to sixteenth, and so on). The starting profiles of this example are in an asynchronous structure relationship, but we can see as shown in FIG. 24C that the composite profile has focal point peaks formed at positions at which the addition power set with the respective starting profiles are 4 D and approximately 2.67 D. Therefore, the diffractive lens based on the composite profile is useful as the same three focal point intraocular lens as that of example 6.

However, with the composite profile of this example, excess peaks due to multi-order light (arrow A in FIG. 24C) are generated at the point of approximately 6.7 D. Next, readjustment of the phase was performed with the composite profile, and a reduction of the multi-order light was performed.

(ii) Generation of the Adjusted Profile by Phase Adjustment

The composite profile of this example is made by repeating a similar phase structure with five continuous zone pitches, so considering that regularity, first, phase adjustment was performed for the first to fifth zones. The phase shift was increased in the minus direction for the second and fourth zones, and the phase constant was made a little smaller and the phase shift was increased in the plus direction for the fifth zone. The same phase adjustments were also implemented on the remaining zone units of the sixth to tenth, eleventh to fifteenth, and sixteenth to eighteenth. The details of the adjusted profile are shown in Table 17 and FIG. 25A.

TABLE 17

| | Zone radius (mm) | | Composite profile (Example 11) | | Adjusted profile(Example 11) | | | |
|---|---|---|---|---|---|---|---|---|
| Zone No. i | Outer radius $r_i$ | Inner radius $r_{i-1}$ | Phase constant h | Phase Shift τ | Phase constant h | Phase Shift τ | After adjustment $\phi_i'$ | After adjustment $\phi_{i-1}'$ |
| 1 | 0.3872 | 0 | 0.394 | −0.757 | 0.35 | −0.459 | −1.5585 | 0.6405 |
| 2 | 0.47 | 0.3872 | 0.137 | −0.230 | 0.1 | −0.593 | −0.9075 | −0.2792 |
| 3 | 0.7027 | 0.47 | 0.625 | −0.114 | 0.6 | −0.065 | 1.9504 | 1.8194 |
| 4 | 0.7479 | 0.7027 | 0.148 | −0.033 | 0.1 | −0.635 | −0.9492 | −0.3209 |
| 5 | 0.8757 | 0.7479 | 0.484 | 0.1769 | 0.35 | 0.413 | −0.6862 | 1.5128 |
| 6 | 0.9848 | 0.8757 | 0.462 | −0.285 | 0.45 | −0.030 | −1.4444 | 1.3830 |
| 7 | 1.0197 | 0.9843 | 0.163 | −0.053 | 0.15 | −0.436 | −0.9079 | 0.0345 |
| 8 | 1.1458 | 1.0197 | 0.632 | −0.041 | 0.6 | −0.023 | −1.9086 | 1.8612 |
| 9 | 1.1740 | 1.1458 | 0.151 | 0.008 | 0.1 | −0.597 | −0.9117 | −0.2834 |
| 10 | 1.2593 | 1.1740 | 0.483 | 0.211 | 0.35 | 0.443 | −0.6562 | 1.5428 |
| 11 | 1.3371 | 1.2593 | 0.466 | −0.257 | 0.45 | −0.011 | −1.4250 | 1.4024 |
| 12 | 1.3634 | 1.3371 | 0.164 | −0.038 | 0.15 | −0.424 | −0.8960 | 0.0464 |
| 13 | 1.4601 | 1.3634 | 0.633 | −0.030 | 0.6 | −0.017 | −1.9022 | 1.8676 |
| 14 | 1.4823 | 1.4601 | 0.151 | 0.016 | 0.1 | −0.589 | −0.9041 | −0.2757 |
| 15 | 1.5507 | 1.4823 | 0.482 | 0.222 | 0.35 | 0.452 | −0.6472 | 1.5518 |
| 16 | 1.6146 | 1.5507 | 0.467 | −0.248 | 0.45 | −0.004 | −1.4185 | 1.4088 |
| 17 | 1.6364 | 1.6146 | 0.164 | −0.033 | 0.15 | −0.420 | −0.8916 | 0.0508 |
| 18 | 1.7178 | 1.6364 | 0.633 | −0.025 | 0.6 | −0.014 | −1.8996 | 1.8703 |

Also, the intensity distribution on the optical axis with the adjusted profile is compared with the composite profile and shown in FIG. 25B (solid line is the adjusted profile, dotted line is the composite profile). We can see that by doing this phase adjustment, the multi-order light peaks shown by arrow A in the drawing are decreased. Also, we can see that the 0th order diffracted light peak intensity increases, and there is also in increase in that peak gain.

When the adjusted profile of this example is used for an intraocular lens, the multi-order light decreases, and when using the 0th order diffracted light for far vision, the gain of that diffracted light increases, so more so than in the case when using a lens from a composite profile, the generation of halo and glare are suppressed, and there is further qualitative improvement in far visual performance without losing visual performance for near vision and intermediate vision.

Also, from the investigation results described above regarding this example as well, even if there is an asynchronous structure relationship for which matching is not seen for any of the zone diameters with the starting profiles, it is possible to understand the present invention as operating effectively.

Example 12

This example is for making the present invention even easier to understand by showing an example for referencing a specific example when the addition power of the starting profile (1) is varied.

(i) Preparation of the Composite Profile

Figure 26A:
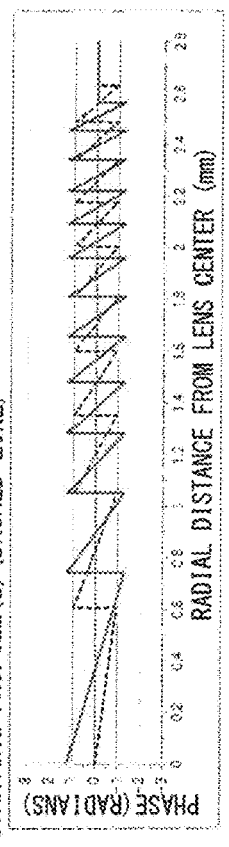
FIGS. 26A-26C are drawings relating to the composite profile of example 12 of the present invention, where
Figure 26B:
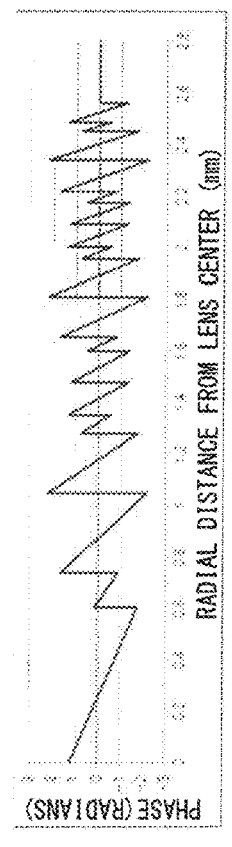

Both starting profiles (1) and (2) have the phase function as a blaze shaped function, where the starting profile (1) is set so that the addition power is $P_1=2$ diopters, and starting profile (2) is set so that the addition power $P_2$ is ¾ of $P_1$ with $P_2=1.5$ diopters. For the respective zone pitches, starting profile (1) was determined using the standard setting equation of Equation 13, and starting profile (2) was determined using the general setting equation of Equation 10, with the first zone radius set at $r_1'=0.6033$ mm. The phase constant of starting profiles (1) and (2) are respectively 0.4 and 0.3, and the phase $\phi_0$ of the first zone of starting profile (2) was determined based on Equation 25. The composite profile was obtained by starting profiles (1) and (2) being respectively overlapped on the same region, and the phase being added. The details of the starting profiles (1) and (2) and the composite profile are shown in Table 18 and FIGS. 26A and 26B.

TABLE 18

| Starting profile(1) Addition power $P_1 = 2\text{ D}$ | | Starting profile(2) Addition power $P_2 = 1.5\text{ D}$ | | Composite profile(Example 12) Zone radius (mm) | | | | | |
|---|---|---|---|---|---|---|---|---|---|
| Zone No. | Zone radius (mm) | Phase constant | Zone No. | Zone radius (mm) | Phase constant | Zone No. | Outer radius | Inner radius | Phase (radians) |
| n | $r_n$ | h | m | $r_m$ | h | i | $r_i$ | $r_{i-1}$ | $\phi_i'$ $\phi_{i-1}'$ |
| 1 | 0.7389 | 0.4 | 1 | 0.6033 | 0.3 | 1 | 0.6033 | 0 | −1.7379 1.2566 |
| 2 | 1.0449 | 0.4 | 2 | 1.0449 | 0.3 | 2 | 0.7389 | 0.6033 | −0.8928 0.1470 |
| 3 | 1.2798 | 0.4 | 3 | 1.3490 | 0.3 | 3 | 1.0449 | 0.7389 | −2.1991 1.6204 |
| 4 | 1.4778 | 0.4 | 4 | 1.5962 | 0.3 | 4 | 1.2798 | 1.0449 | −1.7699 2.1991 |
| 5 | 1.6522 | 0.4 | 5 | 1.8099 | 0.3 | 5 | 1.3490 | 1.2798 | −0.5646 0.7432 |
| 6 | 1.8099 | 0.4 | 6 | 2.0009 | 0.3 | 6 | 1.4778 | 1.3490 | −1.2961 1.3203 |
| 7 | 1.9549 | 0.4 | 7 | 2.1753 | 0.3 | 7 | 1.5962 | 1.4778 | −1.3918 1.2171 |
| 8 | 2.0899 | 0.4 | 8 | 2.3366 | 0.3 | 8 | 1.6522 | 1.5962 | −0.8082 0.4930 |
| 9 | 2.2167 | 0.4 | 9 | 2.4875 | 0.3 | 9 | 1.8099 | 1.6522 | −2.1991 1.7049 |
| 10 | 2.3366 | 0.4 | 10 | 2.6298 | 0.3 | 10 | 1.9549 | 1.8099 | −1.7451 2.1991 |
| 11 | 2.4507 | 0.4 | | | | 11 | 2.0009 | 1.9549 | −0.5424 0.7681 |
| 12 | 2.5596 | 0.4 | | | | 12 | 2.0899 | 2.0009 | −1.2762 1.3425 |
| | | | | | | 13 | 2.1753 | 2.0899 | −1.3776 1.2369 |
| | | | | | | 14 | 2.2167 | 1.1753 | −0.7982 0.5073 |
| | | | | | | 15 | 2.3366 | 2.2167 | −2.1991 1.7150 |
| | | | | | | 16 | 2.4507 | 2.3366 | −1.7387 2.1991 |
| | | | | | | 17 | 2.4875 | 2.4507 | −0.5358 0.7745 |
| | | | | | | 18 | 2.5596 | 2.4875 | −1.2697 1.3491 |

With this example, while the addition power of starting profile (2) is set to be a ¾ of $P_1$, the same as with example 1, the addition power of starting profile (1) is set to be smaller than that of the group of examples noted above at $P_1$=2 diopters. Also, from the second zone of starting profiles (1) and (2), the zone diameters match each other, and thereafter, there is a synchronous structure for which four continuous zone pitches of starting profile (1) and three continuous zone pitches of starting profile (2) match. The synchronous structure is formed at a different point than with example 1, but the repeated pattern of the composite profile phase is similar to that of example 1. In other words, the repeated structure is formed with six zones such as the first to sixth, seventh to twelfth, thirteenth to eighteenth and the like as the unit.

Figure 26C:
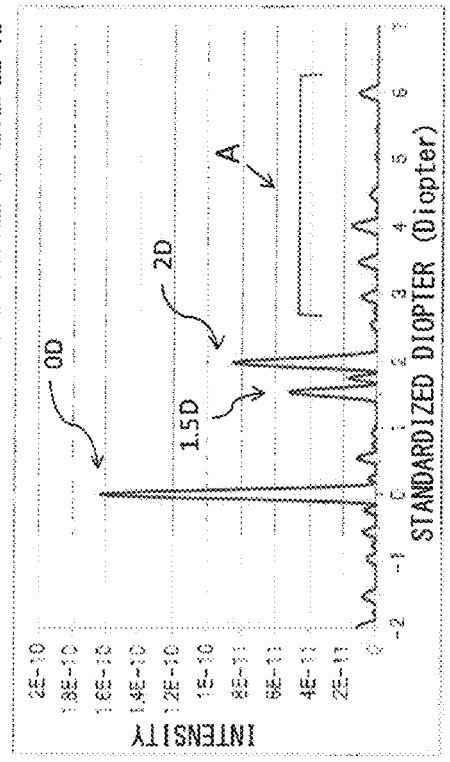

FIG. 26C shows the intensity distribution on the optical axis of this composite profile. With this composite profile, a peak is generated by the 0th order diffracted light, and peaks based on the +1 order diffracted light of starting profiles (1) and (2) are generated at the points of 2 D and 1.5 D.

Patients for which the intraocular lens is used, for example, cataract patients, lose their own power of accommodation, so the near vision focal point position for reading needs to be a 4 D equivalent with the intraocular lens alone. However, with the typical presbyopia patient who still has a small amount of his own power of accommodation remaining, a contact lens prescription is suitable, and with the contact lens, the focal point position with the lens alone that is required with use together with the patient's own power of accommodation is sufficient as a 2 D equivalent. Therefore, by allocating 2 D for near vision, 1.5 D for intermediate vision, and 0 D for far vision, this example useful as a three focal point contact lens for presbyopia patients who still have a small amount of their own power of accommodation remaining. With this prescription example as well, a focal point is set for intermediate vision, so visual acuity is broadly ensured of course for far vision but also from reading distance to the distance for seeing a personal computer monitor screen.

However, with the composite profile of this example, a plurality of multi-order light diffracted light is generated, so the problem of halo and glare occurs. In light of that, phase adjustment was performed on this composite profile to suppress multi-order light.

(ii) Generation of the Adjusted Profile by Phase Adjustment

The composite profile of this example is made by repeating a similar phase structure with six continuous zone pitches, so considering that regularity, first, phase adjustment was performed for the first to sixth zones. The second and fifth zone phase constant was h=0, and the phase shift was slightly increased in the minus direction. Zones other than these had the phase constant and phase shift kept at the fine adjustment level. Phase adjustment was implemented in the same way on the remaining zone units of the seventh to twelfth, and thirteenth to eighteenth. The details of the adjusted profile are shown in Table 19 and FIG. 27A. Also, the intensity distribution on the optical axis compared with the composite profile is shown in FIG. 27B (solid line is the adjusted profile, dotted line is the composite profile).

TABLE 19

| Zone No. i | Zone radius (mm) | | Composite profile (Example 12) | | Adjusted profile(Example 12) | | | |
|---|---|---|---|---|---|---|---|---|
| | Outer radius $r_i$ | Inner radius $r_{i-1}$ | Phase constant h | Phase Shift τ | Phase constant h | Phase Shift τ | After adjustment $\phi_i'$ | After adjustment $\phi_{i-1}'$ |
| 1 | 0.6033 | 0 | 0.476 | −0.240 | 0.4 | −0.083 | −1.3401 | 1.1730 |
| 2 | 0.7339 | 0.6033 | 0.165 | −0.372 | 0 | −0.628 | −0.6283 | −0.6283 |
| 3 | 1.0449 | 0.7389 | 0.607 | −0.289 | 0.6 | −0.192 | −2.0778 | 1.6920 |
| 4 | 1.2798 | 1.0449 | 0.631 | 0.214 | 0.5 | 0.286 | −1.2847 | 1.8568 |
| 5 | 1.3490 | 1.2798 | 0.208 | 0.089 | 0 | −0.314 | −0.3141 | −0.3141 |
| 6 | 1.4778 | 1.3490 | 0.416 | 0.012 | 0.4 | −0.138 | −1.3950 | 1.1182 |
| 7 | 1.5962 | 1.4778 | 0.415 | −0.087 | 0.4 | 0.076 | −1.1803 | 1.3329 |
| 8 | 1.6522 | 1.5962 | 0.207 | −0.157 | 0 | −0.628 | −0.6283 | −0.6283 |
| 9 | 1.8099 | 1.6522 | 0.621 | −0.247 | 0.6 | −0.329 | −2.2143 | 1.5555 |
| 10 | 1.9549 | 1.8099 | 0.627 | 0.226 | 0.5 | 0.302 | −1.2681 | 1.8734 |
| 11 | 2.0009 | 1.9549 | 0.208 | 0.112 | 0 | 0 | 0 | 0 |
| 12 | 2.0899 | 2.0009 | 0.416 | 0.083 | 0.4 | −0.120 | −1.3773 | 1.1359 |
| 13 | 2.1753 | 2.0899 | 0.416 | −0.070 | 0.4 | 0.090 | −1.1666 | 1.3466 |
| 14 | 2.2167 | 2.1753 | 0.207 | −0.145 | 0 | 0.510 | 0.5109 | 0.5109 |
| 15 | 2.3366 | 2.2167 | 0.622 | −0.242 | 0.5 | −0.322 | −1.8935 | 1.2480 |
| 16 | 2.4507 | 2.3866 | 0.626 | 0.230 | 0.6 | 0.153 | −1.7315 | 2.0384 |
| 17 | 2.4875 | 2.4507 | 0.208 | 0.119 | 0 | 0.314 | 0.3141 | 0.3141 |
| 18 | 2.5596 | 2.4875 | 0.416 | 0.039 | 0.4 | −0.115 | −1.3718 | 1.1414 |

As shown in FIG. 27B, we can see that by doing this phase adjustment, the multi-order light peaks shown by arrow A in FIG. 26C are decreased. Also, we can see that the 0th order diffracted light peak intensity increases, and there is also in increase in that peak gain. When the adjusted profile of this example is used for a contact lens, while maintaining the ability to form three focal points with the composite profile, the generation of halo and glare are suppressed, and there is further qualitative improvement in far visual performance along with an increase in gain of the 0th order diffracted light without losing visual performance for near vision and intermediate vision.

Above, we gave a detailed description of the embodiments of carrying out the present invention while showing a number of representative examples, but the present invention is not to be interpreted as being limited by those specific noted contents, and it is possible to add various changes, revisions, improvements or the like based on the knowledge of a person skilled in the art, and any such mode is included in the scope of the claims of the invention as long as it does not stray from the gist of the invention.

For example, the diffractive structure that realizes the zone profiles set with phase adjustment implemented can be set on either the front surface or back surface of the target optical lens. It is also possible to install it on the lens interior, and for example as noted in Japanese Unexamined Patent Publication No. JP-A-2001-042112, it is also possible to form the diffractive structure of the present invention on a laminated surface comprising two materials for which the refractive index is different.

Also, as the ophthalmic lens to which the present invention is applied, specific subjects can include contact lenses, glasses, intraocular lenses or the like, and subjects can also include a cornea insertion lens for correcting vision embedded substantially within the cornea, an artificial cornea or the like. Also, with contact lenses, it is possible to suitably use these for hard contact lenses that are hard and oxygen permeable, soft contact lenses that are hydrogel or non-hydrogel, soft contact lenses that are oxygen permeable hydrogel or non-hydrogel containing a silicon component, or the like. For intraocular lenses as well, it is possible to suitably use these for any intraocular lens such as a hard intraocular lens, a soft intraocular lens that can be bent and inserted in the eye, and the like.

Incidentally, an intraocular lens was described for examples 1 to 11, and a contact lens was described for example 12, but aside from the geometrical lens shape and dimensions, only the refractive power that is the optical base (refractive power of 0th order diffracted light) differs for the intraocular lens and contract lens, and there is no difference in optical characteristics including the focal point position, intensity distribution and the like relating to the addition power exhibited based on the diffractive structure. Also, for both the intraocular lens and contact lens, to begin with, the refractive power that is the base is not limited to being an item that is set appropriately to each individual it is applied to. Therefore, with the examples, in order to clarify more specifically, we presented examples specifying one or the other of the intraocular lens or contact lens, but with any of the examples, the simulation results can be understood to indicate the intraocular lens or contact lens without distinguishing between them. In other words, in that sense, each example discloses the same example for both an intraocular lens and a contact lens.

The invention claimed is:

1. A method for manufacturing a diffractive multi-focal ophthalmic lens capable of generating at least three focal points in an optical axis direction using a diffractive structure comprising a plurality of zones in a concentric circle form, the method comprising:
   generating a composite profile by overlapping at least two starting profiles comprising a plurality of zones in a concentric circle form;
   generating an adjusted profile by adjusting at least one of phase and amplitude with a zone of the composite profile as a subject in order to set an intensity distribution in the optical axis direction and determine optical characteristics; and
   manufacturing the diffractive multi-focal ophthalmic lens for which the adjusted profile is provided in at least a portion of the diffractive structure, wherein
   the at least two starting profiles all have a phase expressed as a blaze shaped function in relation to a lens radial distance in at least a portion of a region overlapped, and the phase of the composite profile is also expressed as a blaze shaped function, and the blaze shaped function of the composite profile is expressed by Equation 1

$$\phi(r) = \frac{\phi_i - \phi_{i-1}}{r_i - r_{i-1}} \times r + \frac{\phi_{i-1} \times r_i - \phi_i \times r_{i-1}}{r_i - r_{i-1}} + \tau \quad \text{[Equation 1]}$$

r: Radial distance from the lens center
$r_{i-1}$: Inner diameter of the ith zone (radius)
$r_i$: Outer diameter of the ith zone (radius)
$\phi_{i-1}$: Phase at the inner diameter (radius) position of the ith zone
$\phi_i$: Phase at the outer diameter (radius) position of the ith zone
$\tau$: Phase shift.

2. The method for manufacturing the diffractive multifocal ophthalmic lens according to claim 1, wherein
adjustment of the phase with the zone of the composite profile as the subject is performed by varying at least one of a phase constant h expressed by Equation 2 using $\phi_i$ and $\phi_{i-1}$ of Equation 1, and a phase shift $\tau$ of Equation 1

$$h = \frac{\phi_{i-1} - \phi_i}{2\pi}. \quad \text{[Equation 2]}$$

3. The method for manufacturing the diffractive multifocal ophthalmic lens according to claim 2, wherein
when adjusting the phase of the composite profile, the adjusted profile is set so as to include the zones for which the phase constant h changes periodically in a radial direction.

4. The method for manufacturing the diffractive multifocal ophthalmic lens according to claim 2, wherein
when adjusting the phase of the composite profile, the adjusted profile is set so as to include the zones for which the phase shift $\tau$ changes periodically in a radial direction.

5. The method for manufacturing the diffractive multifocal ophthalmic lens according to claim 1, wherein
adjustment of the amplitude of the composite profile is performed by adjusting a light transmittance in the zone of the composite profile.

6. The method for manufacturing the diffractive multifocal ophthalmic lens according to claim 5, wherein
when adjusting the amplitude of the composite profile, the adjusted profile is set so as to include the zones for which the light transmittance changes periodically in a radial direction.

7. The method for manufacturing the diffractive multifocal ophthalmic lens according to claim 1, wherein
by adjusting at least one of the phase and amplitude of the composite profile, at least two zones positioned continuously in a radial direction in the composite profile are integrated.

8. The method for manufacturing the diffractive multifocal ophthalmic lens according to claim 1, wherein
at least one of the starting profiles is a first starting profile having a zone pitch expressed by Equation 3 in at least a portion thereof $$r_n = \sqrt{r_1^2 + \frac{2\lambda(n-1)}{P_1}} \quad \text{[Equation 3]}$$

$r_n$: nth zone radius of the first starting profile
$r_1$: First zone radius of the first starting profile
$P_1$: Addition power of the first starting profile
n: Natural number
$\lambda$: Design wavelength.

9. The method for manufacturing the diffractive multifocal ophthalmic lens according to claim 8, wherein
a first zone radius $r_1$ of the first starting profile is expressed by Equation 4

$$r_1 = \sqrt{\frac{2\lambda}{P_1}}. \quad \text{[Equation 4]}$$

10. The method for manufacturing the diffractive multifocal ophthalmic lens according to claim 8, wherein
in addition to the first starting profile, a second starting profile having a zone pitch expressed by Equation 5 in at least a portion thereof is used as the starting profile $$r_m = \sqrt{r_1'^2 + \frac{2\lambda(m-1)}{P_2}} \quad \text{[Equation 5]}$$

$r_m$: mth zone radius of the second starting profile
$r_1'$: First zone radius of the second starting profile
$P_2$: Addition power of the second starting profile
m: Natural number
$\lambda$: Design wavelength.

11. The method for manufacturing the diffractive multifocal ophthalmic lens according to claim 10, wherein
a first zone radius $r_1'$ of the second starting profile is expressed by Equation 6

$$r_1' = \sqrt{\frac{2\lambda}{P_2}}. \quad \text{[Equation 6]}$$

12. The method for manufacturing the diffractive multifocal ophthalmic lens according to claim 10, wherein
an addition power $P_2$ given by the second starting profile is expressed by a relational expression of Equation 7 using an addition power $P_1$ given by the first starting profile,
a and b are mutually different natural numbers, and
quotients when a and b are divided by a mutual greatest common divisor thereof are both an integer other than 1

$$P_2 = \frac{a}{b} \times P_1. \quad \text{[Equation 7]}$$

13. The method for manufacturing the diffractive multifocal ophthalmic lens according to claim 12, wherein
a and b in Equation 7 are set to be a/b>1/2.

14. The method for manufacturing the diffractive multifocal ophthalmic lens according to claim 12, wherein in regards to a and b in Equation 7, a synchronous structure, for which a b-number of zone pitches that are continuous in the first starting profile and an a-number of zone pitches that are continuous in the second starting profile are mutually the same within the same region, is set for at least a portion of a region where the first starting profile and the second starting profile are overlapped.

15. The method for manufacturing the diffractive multi-focal ophthalmic lens according to claim 1, wherein
the composite profile includes the diffractive structure for which in addition to the first starting profile and the second starting profile, a third starting profile is further overlapped on the same region.

16. The method for manufacturing the diffractive multi-focal ophthalmic lens according to claim 15, wherein
at least a portion of the third starting profile has a zone pitch given by Equation 8, and an addition power $P_3$ given by the third starting profile is different from both of the addition powers given by the first and second starting profiles $$r_q = \sqrt{r_1''^2 + \frac{2\lambda(q-1)}{P_3}}$$ [Equation 8]

$r_q$: qth zone radius of the third starting profile
$r_1''$: First zone radius of the third starting profile
$P_3$: Addition power of the third starting profile
q: Natural number
λ: Design wavelength.

17. The method for manufacturing the diffractive multi-focal ophthalmic lens according to claim 16, wherein
a first zone radius $r_1''$ of the third starting profile is expressed by Equation 9

$$r_1'' = \sqrt{\frac{2\lambda}{P_3}}.$$ [Equation 9]

18. The method for manufacturing the diffractive multi-focal ophthalmic lens according to claim 15, wherein
at least a portion of the composite profile has a synchronous structure for which, with $c_1$, $c_2$ and $c_3$ all being mutually different natural numbers, a $c_3$-number of zone pitches continuous in the third starting profile is the same as either a $c_1$-number of zone pitches continuous in the first starting profile or a $c_2$-number of zone pitches continuous in the second starting profile.

19. The method for manufacturing the diffractive multi-focal ophthalmic lens according to claim 15, wherein
an addition power $P_2$ given by the second starting profile is expressed by a relational expression of Equation 10 using an addition power $P_1$ given by the first starting profile, while an addition power $P_3$ given by the third starting profile is determined by Equation 11 using the addition power $P_1$, and
with a greatest common divisor being z for three integers of (b×e), (a×e), and (b×d) expressed using a, b, d, and e in Equation 10 and Equation 11, at least a portion of the composite profile has a synchronous structure for which a (b×e)/z-number of continuous zone pitches in the first starting profile, an (a×e)/z-number of continuous zone pitches in the second starting profile, and a (b×d)/z-number of continuous zone pitches in the third starting profile are mutually the same $$P_2 = \frac{a}{b} \times P_1$$ [Equation 10]

(a, b: Mutually different natural numbers)
$P_2$: Addition power of the second starting profile
$P_1$: Addition power of the first starting profile $$P_3 = \frac{d}{e} \times P_1$$ [Equation 11]

(d, e: Mutually different natural numbers)
$P_3$: Addition power of the third starting profile
$P_1$: Addition power of the first starting profile.

20. The method for manufacturing the diffractive multi-focal ophthalmic lens according to claim 15, wherein
in addition to the first starting profile, the second starting profile, and the third starting profile, a fourth starting profile is also set, and the composite profile includes the diffractive structure which has the first, second, third, and fourth starting profiles overlapped on the same region.

21. The method for manufacturing the diffractive multi-focal ophthalmic lens according to claim 20, wherein
in addition to the first starting profile, the second starting profile, the third starting profile, and the fourth starting profile, a fifth starting profile is also set, and the composite profile includes the diffractive structure which has the first, second, third, fourth, and fifth starting profiles overlapped on the same region.

22. The method for manufacturing the diffractive multi-focal ophthalmic lens according to claim 1, wherein
the diffractive structure comprises a relief structure reflecting an optical path length correlating to the phase.

23. The method for manufacturing the diffractive multi-focal ophthalmic lens according to claim 1, wherein
one of the at least three focal points is used for far vision, another focal point is used for near vision, and yet another focal point is used for intermediate vision.

24. The method for manufacturing the diffractive multi-focal ophthalmic lens according to claim 1, wherein
settings are made such that the focal point for far vision is given by a 0th order diffracted light of the diffractive structure, and the focal point for near vision and the focal point for intermediate vision are respectively given by a +1 order diffracted light of the first starting profile and the second starting profile.

25. A diffractive multi-focal ophthalmic lens comprising
a diffractive structure comprising a plurality of zones in a concentric circle form, the diffractive structure being capable of generating at least three focal points in an optical axis direction, wherein:
the diffractive structure comprises a composite profile which includes a phase profile that is dividable into a plurality of starting profiles being overlapped each other, and for which radial direction positions of the respective zones are set according to the plurality of starting profiles,
an adjusted profile is set for which at least one of the zones of the composite profile is a zone having a different phase and/or amplitude from an overlapping of the plurality of starting profiles, at least a portion of the phase of the adjusted profile is expressed as a blaze shaped function in relation to a lens radial distance, in the plurality of starting profiles, at least a portion of each phase is expressed as a blaze shaped function in relation to a lens radial distance, and the blaze shaped function is expressed by Equation 12

$$\phi(r) = \frac{\phi_i - \phi_{i-1}}{r_i - r_{i-1}} \times r + \frac{\phi_{i-1} \times r_i - \phi_i \times r_{i-1}}{r_i - r_{i-1}} + \tau \quad \text{[Equation 12]}$$

r: Radial distance from the lens center
$r_{i-1}$: Inner diameter of the ith zone (radius)
$r_i$: Outer diameter of the ith zone (radius)
$\phi_{i-1}$: Phase at the inner diameter (radius) position of the ith zone
$\phi_i$: Phase at the outer diameter (radius) position of the ith zone
$\tau$: Phase shift.

26. The diffractive multi-focal ophthalmic lens according to claim 25, wherein by the adjusted profile being set for which at least one of the zones of the composite profile is the zone having the different phase and/or amplitude from the overlapping of the plurality of starting profiles, compared to the phase profile comprising the overlapping of the plurality of starting profiles, a level of multi-order light for a light intensity distribution in the optical axis direction is suppressed.

27. The diffractive multi-focal ophthalmic lens according to claim 25, wherein in at least one of the plurality of starting profiles, at least a portion thereof has a Fresnel pitch.

28. The diffractive multi-focal ophthalmic lens according to claim 25, wherein a radius of each zone that is a non-Fresnel pitch in a mode where the plurality of starting profiles are overlapped is substantially a Fresnel pitch in the adjusted profile by the plurality of zones being integrally consolidated.

29. A diffractive multi-focal ophthalmic lens set comprising a plurality of types of diffractive multi-focal ophthalmic lenses combined into a series, each of the diffractive multi-focal ophthalmic lenses capable of generating at least three focal points in an optical axis direction using a diffractive structure comprising a plurality of zones in a concentric circle form, the diffractive structure comprising a composite profile which includes a phase profile that is dividable into a plurality of starting profiles being overlapped each other, and for which radial direction positions of the respective zones are set according to the plurality of starting profiles, wherein adjusted profiles are set in the respective diffractive multi-focal ophthalmic lenses for which, for each adjusted profile, at least one of the zones of the composite profile is a zone having a different phase and/or amplitude from an overlapping of the plurality of starting profiles, light intensity distributions of the diffractive multi-focal ophthalmic lenses in the optical axis direction are made mutually different by settings of the adjusted profiles being mutually different, at least a portion of the phase of the adjusted profile is expressed as a blaze shaped function in relation to a lens radial distance, in the plurality of starting profiles, at least a portion of each phase is expressed as a blaze shaped function in relation to a lens radial distance, and the blaze shaped function is expressed by Equation 13

$$\phi(r) = \frac{\phi_i - \phi_{i-1}}{r_i - r_{i-1}} \times r + \frac{\phi_{i-1} \times r_i - \phi_i \times r_{i-1}}{r_i - r_{i-1}} + \tau \quad \text{[Equation 13]}$$

r: Radial distance from the lens center
$r_{i-1}$: Inner diameter of the ith zone (radius)
$r_i$: Outer diameter of the ith zone (radius)
$\phi_{i-1}$: Phase at the inner diameter (radius) position of the ith zone
$\phi_i$: Phase at the outer diameter (radius) position of the ith zone
$\tau$: Phase shift.

* * * * *